United States Patent [19]
Rowley et al.

[11] Patent Number: 6,121,419
[45] Date of Patent: Sep. 19, 2000

[54] COMPOSITIONS AND METHODS FOR DETECTING GENE REARRANGEMENTS AND TRANSLOCATIONS

[75] Inventors: Janet D. Rowley; Manuel O. Diaz, both of Chicago, Ill.

[73] Assignee: Arch Development Corp., Chicago, Ill.

[21] Appl. No.: 08/465,713

[22] Filed: Jun. 6, 1995

Related U.S. Application Data

[60] Division of application No. 08/080,255, Jun. 17, 1993, Pat. No. 5,487,970, which is a continuation-in-part of application No. 07/900,689, Jun. 17, 1992, abandoned.

[51] Int. Cl.[7] .......................... C07K 14/00; C07K 16/00; C07K 16/18
[52] U.S. Cl. .................. 530/350; 530/387.1; 530/388.1; 530/388.15
[58] Field of Search .................. 435/6, 7.1–7.9; 536/23.1; 530/388.1, 350, 387.1, 388.15

[56] References Cited

PUBLICATIONS

Mazo et al. PNAS 87:2112–2116, 1990.
Gu et al Cell 71:701–708, 1992.
Kobayashi et al., Heterogeneity of Breakpoints of 11q23 Rearrangements in Hematologic Malignancies Identified With Fluorescence In Situ Hybridization, *Blood*, 82(2):547–551, 1993.
Super et al., "Rearrangements of the MLL Gene in Therapy–Related Acute Myeloid Leukemia in Patients Previously Treated with Agents Targeting DNA–Topoisomerase II", *Blood*, 82(12):3705–3711, 1993.
Martinez–Climent et al., "Detection of 11q23/MLL Rearrangements in Infant Leukemias with Fluorescence In Situ Hybridization and Molecular Analysis", *Leukemia* 9:1299–1304, 1995.
Thirman et al., "Cloning of ELL, a Gene that Fuses to MLL in a t(11;19)(q23;p13.1)in Acute Myeloid Leukemia", *Proc. Natl. Acad. Sci, USA*, 91:12110–12114, 1994.
Thirman et al., "Rearrangement of the MLL Gene in Leukemia", *Proc. Natl. Acad. Sci, USA*, 329:909–914, 1993.
Zeleznik–Le et al., "11q23 Translocations Split the "AT–hook" cruciform DNA–binding Region and the Transcriptional Repression Domain from the Activation Domain of the Mixed–Lineage Leukemia (MLL) Gene", *Proc. Natl. Acad. Sci, USA*, 91:10610–10614, 1994.

*Primary Examiner*—Stephanie Zitomer
*Attorney, Agent, or Firm*—Fulbright & Jaworski, LLP

[57] ABSTRACT

Disclosed is a series of nucleic acid probes for use in diagnosing and monitoring certain types of leukemia using, e.g., Southern and Northern blot analyses and fluorescence in situ hybridization (FISH). These probes detect rearrangements, such as translocations involving chromosome band 11q23 with other chromosomes bands, including 4q21, 6q27, 9p22, 19p13.3, in both dividing leukemic cells and interphase nuclei. The breakpoints in all such translocations are clustered within an 8.3 kb BamHI genomic region of the MLL gene. A novel 0.7 kb BamH1 cDNA fragment derived from this gene detects rearrangements on Southern blot analysis with a single BamHI restriction digest in all patients with the common 11q23 translocations and in patients with other 11q23 anomalies. Northern blot analyses are presented demonstrating that the MLL gene has multiple transcripts and that transcript size differentiates leukemic cells from normal cells. Also disclosed are MLL fusion proteins, MLL protein domains and anti-MLL antibodies.

14 Claims, 10 Drawing Sheets

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 749 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
GATCCTGCCC CAAAGAAAAG CAGTAGTGAG CCTCCTCCAC GAAAGCCCGT CGAGGAAAAG      60

AGTGAAGAAG GGAATGTCTC GGCCCCTGGG CCTGAATCCA AACAGGCCAC CACTCCAGCT     120

TCCAGGAAGT CAAGCAAGCA GGTCTCCCAG CCAGCACTGG TCATCCCGCC TCAGCCACCT     180

ACTACAGGAC CGCCAAGAAA AGAAGTTCCC AAAACCACTC CTAGTGAGCC CAAGAAAAAG     240
```

```
CAGCCTCCAC CACCAGAATC AGGTCCAGAG CAGAGCAAAC AGAAAAAAGT GGCTCCCCGC      300

CCAAGTATCC CTGTAAAACA AAAACCAAAA GAAAAGGAAA AACCACCTCC GGTCAATAAG      360

CAGGAGAATG CAGGCACTTT GAACATCCTC AGCACTCTCT CCAATGGCAA TAGTTCTAAG      420

CAAAAAATTC CAGCAGATGG AGTCCACAGG ATCAGAGTGG ACTTTAAGTT TGTGTATTGC      480

CAAGTCTGTT GTGAGCCCTT CCACAAGTTT TGTTTAGAGG AGAACGAGCG CCCTCTGGAG      540

GACCAGCTGG AAAATTGGTG TTGTCGTCGT TGCAAATTCT GTCACGTTTG TGGAAGGCAA      600

CATCAGGCTA CAAAGCAGCT GCTGGAGTGT AATAAGTGCC GAAACAGCTA TCACCCTGAG      660

TGCCTGGGAC CAAACTACCC CACCAAACCC ACAAAGAAGA GAAAGTCTG GATCTGTACC       720

AAGTGTGTTC GCTGTAAGAG CTGTGGATC                                       749

(2) INFORMATION FOR SEQ ID NO:2:

(i) SEQUENCE CHARACTERISTICS:
        (A) LENGTH: 343 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

CACAACTCCA GGCAAAGGGT GGGATGCACA GTGGTCTCAT GATTTCTCAC TGTGTCATGA       60

TTGCGCCAAG CTCTTTGCTA AAGGAAACTT CTGCCCTCTC TGTGACAAAT GTTATGATGA      120

TGATGACTAT GAGAGTAAGA TGATGCAATG TGGAAAGTGT GATCGCTGGG TCCATTCCAA      180

ATGTGAGAAT CTTTCAGATG AGATGTATGA GATTCTATCT AATCTGCCAG AATGTGTGGC      240

CTACACTTGT GTGAACTGTA CTGAGCGGCA CCCTGCAGAG TGGCGACTGG CCCTTGAAAA      300

AGAGCTGCAG ATTTCTCTGA AGCAAGTTCT GACAGCTTTG TTG                       343

(2) INFORMATION FOR SEQ ID NO:3:

(i) SEQUENCE CHARACTERISTICS:
        (A) LENGTH: 1420 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

CTCGTTAAGC ATTTCTGTTA GTCCTCTTGC CACTAGTGCC TTAAACCCAA CTTTTACTTT       60

TCCTTCTCAT TCCCTGACTC AGTCTGGGGA ATCTGCAGAG AAAAATCAGA GACCAAGGAA      120

GCAGACTAGT GCTCCGGCAG AGCCATTTTC ATCAAGTAGT CCTACTCCTC TCTTCCCTTG      180

GTTTACCCCA GGCTCTCAGA CTGAAAGAGG GAGAAATAAA GACAAGGCCC CCGAGGAGCT      240

GTCCAAAGAT CGAGATGCTG ACAAGAGCGT GGAGAAGGAC AAGAGTAGAG AGAGAGACCG      300

GGAGAGAGAA AAGGAGAATA AGCGGGAGTC AAGGAAAGAG AAAAGGAAAA AGGGATCAGA      360

AATTCAGAGT AGTTCTGCTT TGTATCCTGT GGGTAGGGTT CCAAAGAGA AGGTTGTTGG       420

TGAAGATGTT GCCACTTCAT CTTCTGCCAA AAAAGCAACA GGGCGGAAGA AGTCTTCATC      480

ACATGATTCT GGGACTGATA TTACTTCTGT GACTCTTGGG GATACAACAG CTGTCAAAAC      540

CAAAATACTT ATAAAGAAAG GGAGAGGAAA TCTGGAAAAA ACCAACTTGG ACCTCGGCCC      600

AACTGCCCCA TCCCTGGAGA AGGAGAAAAC CCTCTGCCTT TCCACTCCTT CATCTAGCAC      660

TGTTAAACAT TCCACTTCCT CCATAGGCTC CATGTTGGCT CAGGCAGACA AGCTTCCAAT      720
```

-continued

```
GACTGACAAG AGGGTTGCCA GCCTCCTAAA AAAGGCCAAA GCTCAGCTCT GCAAGATTGA      780

GAAGAGTAAG AGTCTTAAAC AAACCGACCA GCCCAAAGCA CAGGGTCAAG AAAGTGACTC      840

ATCAGAGACC TCTGTGCGAG GACCCCGGAT TAAACATGTC TGCAGAAGAG CAGCTGTTGC      900

CCTTGGCCGA AAACGAGCTG TGTTTCCTGA TGACATGCCC ACCCTGAGTG CCTTACCATG      960

GGAAGAACGA GAAAAGATTT TGTCTTCCAT GGGGAATGAT GACAAGTCAT CAATTGCTGG     1020

CTCAGAAGAT GCTGAACCTC TTGCTCCACC CATCAAACCA ATTAAACCTG TCACTAGAAA     1080

CAAGGCACCC CAGGAACCTC CAGTAAAGAA AGGACGTCGA TCGAGGCGGT GTGGGCAGTG     1140

TCCCGGCTGC CAGGTGCCTG AGGACTGTGG TGTTTGTACT AATTGCTTAG ATAAGCCCAA     1200

GTTTGGTGGT CGCAATATAA AGAAGCAGTG CTGCAAGATG AGAAAATGTC AGAATCTACT     1260

ACAATGGATG CCTTCCAAAG CCTACCTGCA GAAGCAAGCT AAAGCTGTGA AAAAGAAAGA     1320

GAAAAAGTCT AAGACCAGTG AAAAGAAAGA CAGCAAAGAG AGCAGTGTTG TGAAGAACGT     1380

GGTGGACTCT AGTCAGAAAC CTACCCCATC AGCAAGAGAG                          1420
```

(2) INFORMATION FOR SEQ ID NO:4:

(i) SEQUENCE CHARACTERISTICS:
        (A) LENGTH: 4201 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

```
CTCGTTAAGC ATTTCTGTTA GTCCTCTTGC CACTAGTGCC TTAAACCCAA CTTTTACTTT       60

TCCTTCTCAT TCCCTGACTC AGTCTGGGGA ATCTGCAGAG AAAAATCAGA GACCAAGGAA      120

GCAGACTAGT GCTCCGGCAG AGCCATTTTC ATCAAGTAGT CCTACTCCTC TCTTCCCTTG      180

GTTTACCCCA GGCTCTCAGA CTGAAAGAGG GAGAAATAAA GACAAGGCCC CCGAGGAGCT      240

GTCCAAAGAT CGAGATGCTG ACAAGAGCGT GGAGAAGGAC AAGAGTAGAG AGAGAGACCG      300

GGAGAGAGAA AAGGAGAATA AGCGGGAGTC AAGGAAAGAG AAAAGGAAAA AGGGATCAGA      360

AATTCAGAGT AGTTCTGCTT TGTATCCTGT GGGTAGGGTT TCCAAAGAGA AGGTTGTTGG      420

TGAAGATGTT GCCACTTCAT CTTCTGCCAA AAAAGCAACA GGGCGGAAGA AGTCTTCATC      480

ACATGATTCT GGGACTGATA TTACTTCTGT GACTCTTGGG GATACAACAG CTGTCAAAAC      540

CAAAATACTT ATAAAGAAAG GGAGAGGAAA TCTGGAAAAA ACCAACTTGG ACCTCGGCCC      600

AACTGCCCCA TCCCTGGAGA AGGAGAAAAC CCTCTGCCTT TCCACTCCTT CATCTAGCAC      660

TGTTAAACAT TCCACTTCCT CCATAGGCTC CATGTTGGCT CAGGCAGACA AGCTTCCAAT      720

GACTGACAAG AGGGTTGCCA GCCTCCTAAA AAAGGCCAAA GCTCAGCTCT GCAAGATTGA      780

GAAGAGTAAG AGTCTTAAAC AAACCGACCA GCCCAAAGCA CAGGGTCAAG AAAGTGACTC      840

ATCAGAGACC TCTGTGCGAG GACCCCGGAT TAAACATGTC TGCAGAAGAG CAGCTGTTGC      900

CCTTGGCCGA AAACGAGCTG TGTTTCCTGA TGACATGCCC ACCCTGAGTG CCTTACCATG      960

GGAAGAACGA GAAAAGATTT TGTCTTCCAT GGGGAATGAT GACAAGTCAT CAATTGCTGG     1020

CTCAGAAGAT GCTGAACCTC TTGCTCCACC CATCAAACCA ATTAAACCTG TCACTAGAAA     1080

CAAGGCACCC CAGGAACCTC CAGTAAAGAA AGGACGTCGA TCGAGGCGGT GTGGGCAGTG     1140

TCCCGGCTGC CAGGTGCCTG AGGACTGTGG TGTTTGTACT AATTGCTTAG ATAAGCCCAA     1200

GTTTGGTGGT CGCAATATAA AGAAGCAGTG CTGCAAGATG AGAAAATGTC AGAATCTACT     1260
```

```
ACAATGGATG CCTTCCAAAG CCTACCTGCA GAAGCAAGCT AAAGCTGTGA AAAAGAAAGA    1320

GAAAAAGTCT AAGACCAGTG AAAAGAAAGA CAGCAAAGAG AGCAGTGTTG TGAAGAACGT    1380

GGTGGACTCT AGTCAGAAAC CTACCCCATC AGCAAGAGAG GATCCTGCCC CAAAGAAAAG    1440

CAGTAGTGAG CCTCCTCCAC GAAAGCCCGT CGAGGAAAAG AGTGAAGAAG GAATGTCTC     1500

GGCCCCTGGG CCTGAATCCA AACAGGCCAC CACTCCAGCT TCCAGGAAGT CAAGCAAGCA    1560

GGTCTCCCAG CCAGCACTGG TCATCCCGCC TCAGCCACCT ACTACAGGAC CGCCAAGAAA    1620

AGAAGTTCCC AAAACCACTC CTAGTGAGCC CAAGAAAAAG CAGCCTCCAC CACCAGAATC    1680

AGGTCCAGAG CAGAGCAAAC AGAAAAAAGT GGCTCCCCGC CCAAGTATCC CTGTAAAACA    1740

AAAACCAAAA GAAAAGGAAA AACCACCTCC GGTCAATAAG CAGGAGAATG CAGGCACTTT    1800

GAACATCCTC AGCACTCTCT CCAATGGCAA TAGTTCTAAG CAAAAAATTC AGCAGATGG     1860

AGTCCACAGG ATCAGAGTGG ACTTTAAGTT TGTGTATTGC CAAGTCTGTT GTGAGCCCTT    1920

CCACAAGTTT TGTTTAGAGG AGAACGAGCG CCCTCTGGAG GACCAGCTGG AAAATTGGTG    1980

TTGTCGTCGT TGCAAATTCT GTCACGTTTG TGGAAGGCAA CATCAGGCTA CAAAGCAGCT    2040

GCTGGAGTGT AATAAGTGCC GAAACAGCTA TCACCCTGAG TGCCTGGGAC CAAACTACCC    2100

CACCAAACCC ACAAAGAAGA AGAAAGTCTG GATCTGTACC AAGTGTGTTC GCTGTAAGAG    2160

CTGTGGATCC ACAACTCCAG GCAAAGGGTG GGATGCACAG TGGTCTCATG ATTTCTCACT    2220

GTGTCATGAT TGCGCCAAGC TCTTTGCTAA AGGAAACTTC TGCCCTCTCT GTGACAAATG    2280

TTATGATGAT GATGACTATG AGAGTAAGAT GATGCAATGT GGAAAGTGTG ATCGCTGGGT    2340

CCATTCCAAA TGTGAGAATC TTTCAGATGA GATGTATGAG ATTCTATCTA ATCTGCCAGA    2400

ATGTGTGGCC TACACTTGTG TGAACTGTAC TGAGCGGCAC CCTGCAGAGT GGCGACTGGC    2460

CCTTGAAAAA GAGCTGCAGA TTTCTCTGAA GCAAGTTCTG ACAGCTTTGT TGAATTCTCG    2520

GACTACCAGC CATTTGCTAC GCTACCGGCA GCTGCCAAGC TCCAGACTTA AATCCCGAGA    2580

CAGAGGAGAG TATACCTTCC CGCAGCTCCC CCGAAGACCT GATCCACCAG TTCTTACTGA    2640

GGTCAGCAAA CAGGATGATC AGCAGCCTTT AGATCTAGAA GGAGTCAAGA GGAAGATGGA    2700

CCAAGGGAAT TACACATCTG TGTTGGAGTT CAGTGATGAT ATTGTGAAGA TCATTCAAGC    2760

AGCCATTAAT TCAGATGGAG GACAGCCAGA AATTAAAAAA GCCAACAGCA TGGTCAAGTC    2820

CTTCTTCATT CGGCAAATGG AACGTGTTTT TCCATGGTTC AGTGTCAAAA AGTCCAGGTT    2880

TTGGGAGCCA AATAAAGTAT CAAGCAACAG TGGGATGTTA CCAAACGCAG TGCTTCCACC    2940

TTCACTTGAC CATAATTATG CTCAGTGGCA GGAGCGAGAG GAAAACAGCC ACACTGAGCA    3000

GCCTCCTTTA ATGAAGAAAA TCATTCCAGC TCCCAAACCC AAAGGTCCTG GAGAACCAGA    3060

CTCACCAACT CCTCTGCATC CTCCTACACC ACCAATTTTG AGTACTGATA GGAGTCGAGA    3120

AGACAGTCCA GAGCTGAACC CACCCCCAGG CATAGAAGAC AATAGACAGT GTGCGTTATG    3180

TTTGACTTAT GGTGATGACA GTGCTAATGA TGCTGGTCGT TTACTATATA TTGGCCAAAA    3240

TGAGTGGACA CATGTAAATT GTGCTTTGTG GTCAGCGGAA GTGTTTGAAG ATGATGACGG    3300

ATCACTAAAG AATGTGCATA TGGCTGTGAT CAGGGGCAAG CAGCTGAGAT GTGAATTCTG    3360

CCAAAAGCCA GGAGCCACCG TGGGTTGCTG TCTCACATCC TGCACCAGCA ACTATCACTT    3420

CATGTGTTCC CGAGCCAAGA ACTGTGTCTT TCTGGATGAT AAAAAAGTAT ATTGCCAACG    3480

ACATCGGGAT TTGATCAAAG GCGAAGTGGT TCCTGAGAAT GGATTTGAAG TTTTCAGAAG    3540

AGTGTTTGTG GACTTTGAAG GAATCAGCTT GAGAAGGAAG TTTCTCAATG GCTTGGAACC    3600
```

-continued

```
AGAAAATATC CACATGATGA TTGGGTCTAT GACAATCGAC TGCTTAGGAA TTCTAAATGA    3660

TCTCTCCGAC TGTGAAGATA AGCTCTTTCC TATTGGATAT CAGTGTTCCA GGGTATACTG    3720

GAGCACCACA GATGCTCGCA AGCGCTGTGT ATATACATGC AAGATAGTGG AGTGCCGTCC    3780

TCCAGTCGTA GAGCCGGATA TCAACAGCAC TGTTGAACAT GATGAAAACA GGACCATTGC    3840

CCATAGTCCA ACATCTTTTA CAGAAAGTTC ATCAAAAGAG AGTCAAAACA CAGCTGAAAT    3900

TATAAGTCCT CCATCACCAG ACCGACCTCC TCATTCACAA ACCTCTGGCT CCTGTTATTA    3960

TCATGTCATC TCAAAGGTCC CCAGGATTCG AACACCCAGT TATTCTCCAA CACAGAGATC    4020

CCCTGGCTGT CGACCGTTGC CTTCTGCAGG AAGTCCTACC CCAACCACTC ATGAAATAGT    4080

CACAGTAGGT GATCCTTTAC TCTCCTCTGG ACTTCGAAGC ATTGGCTCCA GGCGTCACAG    4140

TACCTCTTCC TTATCACCCC AGCGGTCCAA ACTCCGGATA ATGTCTCCAA TGAGAACTGG    4200

G                                                                    4201
```

(2) INFORMATION FOR SEQ ID NO:5:

(i) SEQUENCE CHARACTERISTICS:
        (A) LENGTH: 1321 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

```
CGAGGGCCAC AAAAATGAGC CAAAGATGGA TAACTGCCAT TCTGTAAGCA GAGTTAAAAC      60

ACAGGGACAA GATTCCTTGG AAGCTCAGCT CAGCTCATTG GAGTCAAGCC GCAGAGTCCA     120

CACAAGTACC CCCTCCGACA AAAATTTACT GGACACCTAT AATACTGAGC TCCTGAAATC     180

AGATTCAGAC AATAACAACA GTGATGACTG TGGGAATATC CTGCCTTCAG ACATTATGGA     240

CTTTGTACTA AAGAATACTC CATCCATGCA GGCTTTGGGT GAGAGCCCAG AGTCATCTTC     300

ATCAGAACTC CTGAATCTTG GTGAAGGATT GGGTCTTGAC AGTAATCGTG AAAAAGACAT     360

GGGTCTTTTT GAAGTATTTT CTCAGCAGCT GCCTACAACA GAACCTGTGG ATAGTAGTGT     420

CTCTTCCTCT ATCTCAGCAG AGGAACAGTT TGAGTTGCCT CTAGAGCTAC CATCTGATCT     480

GTCTGTCTTG ACCACCCGGA GTCCCACTGT CCCCAGCCAG AATCCCAGTA GACTAGCTGT     540

TATCTCAGAC TCAGGGGAGA AGAGAGTAAC CATCACAGAA AAATCTGTAG CCTCCTCTGA     600

AAGTGACCCA GCACTGCTGA GCCCAGGAGT AGATCCAACT CCTGAAGGCC ACATGACTCC     660

TGATCATTTT ATCCAAGGAC ACATGGATGC AGACCACATC TCTAGCCCTC CTTGTGGTTC     720

AGTAGAGCAA GGTCATGGCA ACAATCAGGA TTTAACTAGG AACAGTAGCA CCCCTGGCCT     780

TCAGGTACCT GTTTCCCCAA CTGTTCCCAT CCAGAACCAG AAGTATGTGC CCAATTCTAC     840

TGATAGTCCT GGCCCGTCTC AGATTTCCAA TGCAGCTGTC CAGACCACTC CACCCCACCT     900

GAAGCCAGCC ACTGAGAAAC TCATAGTTGT TAACCAGAAC ATGCAGCCAC TTTATGTTCT     960

CCAAACTCTT CCAAATGGAG TGACCCAAAA AATCCAATTG ACCTCTTCTG TTAGTTCTAC    1020

ACCCAGTGTG ATGGAGACAA ATACTTCAGT ATTGGACCC ATGGGAGGTG GTCTCACCCT    1080

TACCACAGGA CTAAATCCAA GCTTGCCAAC TTCTCAATCT TTGTTCCCTT CTGCTAGCAA    1140

AGGATTGCTA CCCATGTCTC ATCACCAGCA CTTACATTCC TTCCCTGCAG CTACTCAAAG    1200

TAGTTTCCCA CCAAACATCA GCAATCCTCC TTCAGGCCTG CTTATTGGGG TTCAGCCTCC    1260

TCCGGATCCC CAACTTTTGG TTTCAGAATC CAGCCAGAGG ACAGACCTCA GTACCACCTC    1320
```

G                                                                                    1321

(2) INFORMATION FOR SEQ ID NO:6:

(i) SEQUENCE CHARACTERISTICS:
        (A) LENGTH: 8392 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

```
GGATCCTGCC CCAAAGAAAA GCAGTAGTGA GCCTCCTCCA CGAAAGCCCG TCGAGGAAAA        60

GAGTGAAGAA GGGAATGTCT CGGCCCCTGG GCCTGAATCC AAACAGGCCA CCACTCCAGC       120

TTCCAGGAAG TCAAGCAAGC AGGTCTCCCA GCCAGCACTG GTCATCCCGC CTCAGCCACC       180

TACTACAGGA CCGCCAAGAA AAGAAGTTCC CAAAACCACT CCTAGTGAGC CAAGAAAAA        240

GCAGCCTCCA CCACCAGAAT CAGGTGAGTG AGGAGGGCAA GAAGGAATTG CTGAACCACA       300

AGTACTAACA AAAAAGCACT GATGTCTCAA ACAGCATTTG AAAGCAGGAA ATGTATGATT       360

TGAAGTCTTC AGTTCAAGAA AATCAGCTCT CTTTCTAACT ATTATGTTTA ATAATAAAGA       420

AACAGAAACA AAAAAAACAG TTAAATTGGA GGTATTGTTT TAATTTCCTG TTCGAAGCCT       480

AGAGTTTAAA TAGTTTTTTT TTTTTTTTC TAATGGCCCT TTCTTCACAG GTCAGTCAGT        540

ACTAAAGTAG TCGTTGCCAG CATCTGACTG CAATTTATTC TGAATTTTTT AGGTCCAGAG       600

CAGAGCAAAC AGAAAAAAGT GGCTCCCCGC CCAAGTATCC CTGTAAAACA AAACCAAAA        660

GAAAAGGTGA GGAGAGATTT GTTTCTCTGC CATTTCTCAG GGATGTATTC TATTTTGTAG       720

CTTTTCCACT CCTCTCTAAA CAAAGAGACG GTAAAGAGTC CCTACATAAG ATAAAACATC       780

GGAAAAGCCT TATCCTTGAC TTCTATGTAG ATGGCAGTGG AATTTCTTAA AATTAAGAAA       840

CTTCAAGTTT AGGCTTTTAG CTGGGCACGG TGGCTCACGC TGGTAATCCC AACACTTAGT       900

GAGGCTGAGG TGGGAGGATT GCTTGAGGCC AGCAGTTCAA GACCAGCCTG GGCAACATAG       960

CAAGACCCTG TCTTTATTTA AACAAAAAAA AAAAAAGAA GAAGAAGAAG TTAGCCAGGC       1020

ATGGTGGCAG TTGCGTGTAG TCCCAGGTAC TCAGGAGGCT GAGATAGAAG GATTGTCTTG      1080

AGCCCAGGAA TTCAAGGCTG TAGTGAGCTA TGATTGTACC ACTGCAGTCC AGCCTGGGTG      1140

ACAAAGCAAA ACACTGTCTC CAAAAAAAAT TTAGGCTTGG CAAGGCGCAC GGCTCACGCC      1200

TGTGATCCCA GCACTTTGGG AAGCCGAAGC AGGCAGATCA CTTGAGGTCA GGAGTTGGAG      1260

ACCAGCCTGG CCAACATGGT GAAACCCTGT CTCTACTGAA AATACAAAAA TTAGCCGGTT      1320

GTGGTAGTGG GTGCTTGTAA TCCTAGCTAC TTGGGAGGCT GAGGCAGGGG AATTGCCTGA      1380

ACCTGCGAGG CGGAGGCTGC AGTGAGCCGA GATTGCATCA TTGCACTCTA GCCTGGACAA      1440

CAGAGCTAGA CTCCATCCCA AAAAAAAAAA AAAAGTAGC CGGGCACGTG GCTCACGCCT       1500

GTAATCCCAG CACTTTGGGA GGCCGAGGCG GCGGATCAT GAGGGCAGGA GATCGAGACC       1560

ATCCTGGCTA ACACGGTGAA ACCCTGTCTC TACTAAAAAT ACAAAAAATT AGCCCGGCGA      1620

GGTGCGGGCG CCTGTAGTCC CAGCTACTCA GGAGAGTGAG GCAGGAGAAT GGCGTGAACC      1680

CGGGGGCGGA GCCTGCAGTG AGCCGAGATC GCGCCACTGC ACTCCAGCTT GGGTGACACC      1740

GAGACTCCGT CTCAAAAAAA AATAAAAAGT TTAGGCTTTA GCCTGTTTCT TTTTTGGTTT      1800

CTTCCTTGTT GCTTTTCCCT TCTTTGTGGC CCCACATGTT CTAGCCTAGG AATCTGCTTA      1860

TTCTAAAGGC CATTTGGCGT AATTATTTTT TGACCCCAAC ATCCTTTAGC AATTATTTGT     1920
```

-continued

```
CTGTAAAAAT CACCCTTCCC TGTATTCACT ATTTTTATTT ATTATGGATA AAGAGATAGT    1980

GTGGTGGCTC ACATCTATAA TCCCAGCACT TTGGGGGGCC AAGGCGGGAG GATCACTTGA    2040

GGGCAGGAGC TGGAGACCAG CCTGGGCAGC ACAGTGACAC ACAGTTGCTA TAAAAAATTT    2100

AAAAATCAAC TAGGCATGGT GGCATGCACC TGTAGTCCCA GCTACTCTTG AGAAGCTGAG    2160

GCAGGAGGAT CACGAGCCCA CAAGGTCTAG GCTGCAGTGA GCTGTGACTG TGCCACTGTA    2220

TTGCAGCCTA GGCAACAAAG CAAGACCCAG TCTCTTTTAA AAAAAATTC AAAGATTATT    2280

TGTTTATGTT GGAAACATGT TTTTTAGATC TATTAATAAA ATTTGTCATT TGCATTATTA    2340

TCTGTTGCAA ATGTGAAGGC AAATAGGGTG TGATTTGTT CTATATTCAT CTTTTGTCTC    2400

CTTAGGAAAA ACCACCTCCG GTCAATAAGC AGGAGAATGC AGGCACTTTG AACATCCTCA    2460

GCACTCTCTC CAATGGCAAT AGTTCTAAGC AAAAAATTCC AGCAGATGGA GTCCACAGGA    2520

TCAGAGTGGA CTTTAAGGTA AAGGTGTTCA GTGATCATAA AGTATATTGA GTGTCAAAGA    2580

CTTTAAATAA AGAAAATGCT ACTACCAAAG GTGTTGAAAG AGGAAATCAG CACCAACTGG    2640

GGGAATGAAT AAGAACTCCC ATTAGCAGGT GGGTTTAGCG CTGGGAGAGC TTTGGTCAGT    2700

GTTGTTAGGT CACTGTTTGT GAACTGACTG CAGAACATAC ATAATGAAAC ATTCCTATCC    2760

ATCCTGAGCA GTATCAGAGG AAGTAATTCC TTCACATGGA AAGTATCAAA CCATGATGAT    2820

TCCTTGAGTC AGCAAAACTG TAAGAGAAAT TCAATCCCAG TGTATTTTCG CAATATATTC    2880

AATATGAATT GAACAACTAG GTGAGCCTTT TAATAGTCCG TGTCTGAGAT TAAAACTTTT    2940

TAAAGCAGCA GTTATTTTTG GACTCATTGA AATGAAATAC TCTGACATTG TGATGTCACA    3000

CTAATTTTAT GCTTTTCATC CTTATTTTCC ATCCAAAGTT GTGTAATTGT AAAACTTTCC    3060

TAAGTGACCT TTCTCTCTCC ACAGGAGGAT TGTGAAGCAG AAAATGTGTG GGAGATGGGA    3120

GGCTTAGGAA TCTTGACTTC TGTTCCTATA ACACCCAGGG TGGTTTGCTT TCTCTGTGCC    3180

AGTAGTGGGA ATGTAGAGGT AAGGCATCCT GCTTCTTTGT ACCCCAGGAA GTACATAAAT    3240

TATTTTTCTG TGGATGAAAT TACTATAGTC TGTTTTGTTG GTATTTAGCA GGTACTATTC    3300

CCTGTTTAAA CCAGCTAAAG AAATGTTTTG AAGTATTTTA GAGATTTTAG GAAGGAATCT    3360

GCTATTAGAG TAGCAAAGTT ATTGAGAGTG AAAAGATCAA TCCTCCCATC TCTCTTAAAT    3420

TCAGTCTTTA TTAGAGTTCT GATCTTTCTG TTAGATGTCT AAATAAGAGA AAAAATTATA    3480

CAGTGGTCTA TTAAAAGGGA TGCTATTGAT GGTTATTTTA TATTGTATAT CAAAGCCTCT    3540

TCATCTATAA GGAGCTCTTA CCAATTAATA AGAAAAGGA ATGACATCCA GAAAAAAAAA    3600

TAGGCAAAAG ACAGAAATAG ATAATTCACA AAATTAGAAA TAAATACATG TTGGGTGGCA    3660

GGGGGAGGTG AAGGGAGGGT GTCTGTTTTT TAGCCCTCTA GTGACCAAAA ACTGGAAATT    3720

AAAGCATGAT AAAAAAAGAA TCCTGAATAA ATGGGGACTT TCTGTTGGTG GAAAGAAATA    3780

TAGATTAGTT ACAATCTTTC TTTCTGAGGG AATTATTTGG AAATATATAT CTATCTTTAA    3840

AATAGGTATA TCCTCTAACA TAGCAATTGC ACTTCAAACA CTTATGGATA TAATTAGATA    3900

AATTGGCAAA TCTGTAGATA TAAAGAAGTG TTCATTTCAA TATTGCTCAT AATAATAAAA    3960

AACTGGAAAC AACCCGAAAG TCCATCTATA GGGAGCATGG GTTAAAATAA GCATAGGGCA    4020

TATAGCTGGG CACGGTGGCT CACGCCTGTA ATCCCAGCAC TTTGGGAGGC CAAGGCAGGC    4080

GGATCACAAG GTCAGGAGAT CCAGACCATC CTGGCTAACA CAGTGAAACC CCGTCTCTAT    4140

TAAAAATACA AAAAAATTAG CCGGGTGTGG TGGCGGGCGC CTGTAGTCCC AGCTACTCGA    4200

GAGGCTGAGG CAGGAGAACG GCATGAACCC GGGAGGTGGA GCTTGCAGTG AGCCGAGATC    4260

GCCCCACTGC ACTCCCGCCT GGGCTACAGA GCAAGACTCC GTCTCAAAAA AAAATAAAAG    4320
```

```
TGTAGGGCAT ATATAATGGC AAATATGAAG TCCTAAAGAT AATATATATT AATATTATTA       4380

GGTTGGTGCA AAAGTAATTG CAGTAATAAC ATGGAAAGAT GTCCATGACA TATCACTGAG       4440

TGAAAAGAGC AGGTTACAAG ATAATATATA AAGCACAATC CCATCTTAGT TTGGAAAAGT       4500

GTTTTTAAAG TATATATCTA GAAAACAATC TGGAAGGATT CACACCAAAA TATTAAGAGT       4560

GTGGTTGGAT TATGGGTGAC CTTTATTTGT TTCTCTGGTT TTTTTTTTTT TAATCTTTCT       4620

GAGTTTTTTG CAGTATGTAC CACCTTTACA ATGAGGAAGG AAAAAGTAGC ACAATTTTAA       4680

ATAGGAAGCA GTAGTTTGTC ATTTATAAGG GACATATCCT ACATCCTTTA CAGTTCTTAA       4740

ATTCCTGGCA GATACCTCTT TGGCTTATTA CTTACCACAT AAGATATGTA TTCAAAGGTG       4800

GTAAAGAAAA TCCACGTCGG GTGCAGTGGC TCACGCCTGT AATCCCAGTA CTTTGGGAGG       4860

CTGACGCAGG AGGACCGCTT GAGCTCAGGA GTTCAAGACC AGCCTGAGCA CCATAGTGAG       4920

ACCTCATCTC TACTAAAAAA AAAATAAAAT ACCAGGCATG GTAGCATGTG CCTGTAGTCC       4980

CAGCTACTCT AGTCCCAGCT ACTTGGGAGG CTGAGGTGAG AGGATCACTT GAGCCCAGGA       5040

GATCGAGGCT GCAGTGAGCC ATTATCACGC CACTGCACTC CAGCCTGGGC AACTAAGCAA       5100

GACCCTGTCT CAAAAAAATT TTAAAAAATT TAAAAAATAA GAAAATCCAA GCTAGGTTGA       5160

AATCTGAATG TTGAGCAGTC AGTGAGACAC AAACTAGCTA AGAAAGTCAA CCCTGCCCAC       5220

TTGCCATTTG AAGTTATTAC TAGCAAAATT ACAAATTATT GCCTACTATT CATTTACTAA       5280

GCAAATATTC TCTTAGTCCC TATTACGAAC AACTTATTGT TCTAAGTGCA GAAGTTCAGA       5340

TATCATTGAG ACTGAGAATA TTCAGTCTAC AAGTGCCAGG GGTCTACTGT ATCCTCTTTT       5400

CCGTCTTAAT ACAGTGCTTT GCACCCATAT ATATGCCACC CACAGGAATA ACTTTTTTTA       5460

TAGCACCAGT CCTTCAACTT CTGGGATTAA ACAGATTTTT TTTCAGGGTA TAATTGTTCT       5520

GATCTAAATT CTTTATAGTT GTACATAGCA ATCTCACAGG GTTCCTAAAA TATAAATTAG       5580

AGAATAGCAT GCTGCCTGCA CTGCACTCCT AAAGCATGAC CAGTGCTTGA TAAACTCTCC       5640

TCCATGCGAA TTTTTTAAAC TTTTTATGTT GACATGATTT CAGACTTACA AAAAACTAT        5700

GAGTTGTACA GAGAATTCTA AGTACCCCTC ACCCAAATTC CCTAAGTGTT AATATGTTTC       5760

TCTGTGTGTA TATATTTTAC AAAATAACAA ATAAAATACA TATACACATT TTACCTGTAG       5820

ATACACATGT ATCTAAAAAT TTGAGAACAA GTTGCAGACA TAAACCATTT TACCTCTAAA       5880

TATTTTAGTG TATATTTTTA AAAATCAAGG ACGTTCTCGT ATTTAACCAT GGTATAATTA       5940

CCAAATCAGG AAATTAACAC ACTGGTACAT TACTATTATC TGATCTATAG GCCTTATTTA       6000

GGTTTGACCA ATTGTCCCAA TAATTCCTTT ATGGCAAAAG AAAATTCTGG ATTATCCTAG       6060

TTAGTATTTT TGAAAATCCT ATATCAATAT GAAAATAACT TATTTCTAAA ATTAGAAATG       6120

GAGGCTGGGC GTGGTGGCTC ACGCCTATAA TCCCAGCACT TTGGGAGGCC GAGGCAGGCA       6180

GATCACAAGG TCAGGAGATT GAGACCATCC TCGCTAACAC AGTGAAACCC CATCTCTACT       6240

AAAAATACAA AAAATTAGCC AGGTGTGGTG GCACGCGCCT GTGATCCCAG CTACTCAGGA       6300

GACTGAGGCT GGAGAATCGC TTGAACCCAG GAGGCGGAGG TTGCAGTGAG TCGAGATCGC       6360

ACCACTGCAC CCCAGCCTGG GCGACACGGA GACTCCGTCT CAAAAAAATA AATAAATAAA       6420

AATTAAAACA ATTAAAAAAA TAAAATTACA AATGGAAAGG ACAAACCAGA CCTTACAACT       6480

GTTTCGTATA TTACAGAAAA CGTTTAAACC CTCCCTATTT CCCCCACCCC ACTCCTTTAT       6540

ATTCCCATAG CTCTTTGTTT ATACCACTCT TAGGTCACTT AGCATGTTCT GTTAAATCTT       6600

GTATTATATT TATTTTGTTA CTTTCTATTT CCACTGGTAT TACCACTTTA GTACTCTGAA       6660
```

```
TCTCCCGCAA TGTCCAATAC TGTACTTTTT TACATAGTCA TTGCTTAATG AATATGTATT    6720

GAATTAAATA TATGCCAGTG GACTACTAAA ACCCAAAGTA TATAAGAAGG GTATGGTTGA    6780

TTATGTTTTT CTACATATTA TTTGACATAC TTCTATCTTC CCATGTTCTT ACTATAGTTT    6840

GTGTATTGCC AAGTCTGTTG TGAGCCCTTC CACAAGTTTT GTTTAGAGGA GAACGAGCGC    6900

CCTCTGGAGG ACCAGCTGGA AAATTGGTGT TGTCGTCGTT GCAAATTCTG TCACGTTTGT    6960

GGAAGGCAAC ATCAGGCTAC AAAGGTACAA AACTTGGTAA TAGAACTACA GCTGGGCCTC    7020

TGTATCAGTG GGTTCTGTAT CCCTGGACTC AACCAACCTT GGATTGAATG TATCTGGGAA    7080

AAAATGAGTA GTTGCCTCTG TACTCTATGT GAACAGACTT TTTCTTGTCA TTATTTCCTA    7140

AACAATACAG TATAACAACT ATTTACATTG TATTAGGTAT GATAAGTAAT CTAGAGATAA    7200

TTTAAAGTAT ATGGTGGGCG GATCACTTGA AGCCAGGAGT TCGAGACCAG CCTGAGCCAA    7260

CATGGTGAAA CCCCATCTCT ACTAAAAATA CAAAAAATTA GCCAGGTGTG GTGGTGGGCA    7320

CCTGTAGTCC CAGCTACTTG GGAGGCTGAG GGAGGAAAAT CGCTTGAACT TTGGAGGCAG    7380

AGGTTGCAGT GAGCCACTCC AGCCTGTGGT GCAGTCTGTC ACTCCAGCCT GGGTGACACA    7440

GTGAGACTCC ATCTCAAAAA AAAAAAAAA AAAAAAACTA TATGGGAGGA TGTGCATTTT    7500

GTTATATGCA AATGCTGCAC CATTTTGTCT AGGGACTTGG GCATCCATGG ACTTTGGTAT    7560

CCTCTGGGGG TCCTGGAACC AATCCCCCAT GGAAACCAAG GATGACTGTG CTTAGAGTAT    7620

TGCTTTCTTT CTTGATTTGT ATTTCTGTCT TCCAGTTAAG ATTTTGTATC TATATTATTT    7680

CTCTTTTTAC TTAGTCTGTC TTTAGCATTT AATTGGGTGT AATCAGTTGC CTATTTTGTG    7740

TTTTAATTTT GGGACTATAG CAGAAAACAT GATGTTGAAT AAAATTCCAA AAATAAGTCA    7800

AATCTACCTA ATATGAATAC TCATCACTGA GTGCCTTTGG CCAGGAAATA AATCTATCTC    7860

AATGCTTTAA TTGGGAGTAA ATAATGTATG AGGAAATTTA AACTCATAAT TGTGTGCTGT    7920

ACTTACTTGC CAGTAAATGT GAAATGGGGT ACTAAGTAAT AGGTGTTGGG TGAAGGTAAT    7980

ATGATGCTTA TCTTTTTGCC ATTATATTTT CTTACAGCAG CTGCTGGAGT GTAATAAGTG    8040

CCGAAACAGC TATCACCCTG AGTGCCTGGG ACCAAACTAC CCCACCAAAC CCACAAAGAA    8100

GAAGAAAGTC TGGGTGAGTT ATACACATGA TGCTCTTTTA TAGAGAACCA CCATGTGACT    8160

ATTGGACTTA TGTAACTTGT ATTACAATAT CTATGCTTGA GGATGTCAGT ATGACAATCT    8220

TTTTGCCTCA TTACTAGGAA ATCATCTCAG CAGAGAAATT AAATCTATAA ATGGATGCAT    8280

TTAAGATCTT TTTAGTTAAG TAAAGATATT AAAAACAAGA AATTCCTATT GAATTTCTTT    8340

TCTTCTTTTC TAGATCTGTA CCAAGTGTGT TCGCTGTAAG AGCTGTGGAT CC            8392

(2) INFORMATION FOR SEQ ID NO:7:

(i) SEQUENCE CHARACTERISTICS:
        (A) LENGTH: 1400 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

Ser Leu Ser Ile Ser Val Ser Pro Leu Ala Thr Ser Ala Leu Asn Pro
1               5                  10                  15

Thr Phe Thr Phe Pro Ser His Ser Leu Thr Gln Ser Gly Glu Ser Ala
                20                  25                  30

Glu Lys Asn Gln Arg Pro Arg Lys Gln Thr Ser Ala Pro Ala Glu Pro
        35                  40                  45
```

-continued

```
Phe Ser Ser Ser Ser Pro Thr Pro Leu Phe Pro Trp Phe Thr Pro Gly
    50                  55                  60

Ser Gln Thr Glu Arg Gly Arg Asn Lys Asp Lys Ala Pro Glu Glu Leu
65                  70                  75                  80

Ser Lys Asp Arg Asp Ala Asp Lys Ser Val Glu Lys Asp Lys Ser Arg
                85                  90                  95

Glu Arg Asp Arg Glu Arg Glu Lys Glu Asn Lys Arg Glu Ser Arg Lys
                100                 105                 110

Glu Lys Arg Lys Lys Gly Ser Glu Ile Gln Ser Ser Ser Ala Leu Tyr
            115                 120                 125

Pro Val Gly Arg Val Ser Lys Glu Lys Val Val Gly Glu Asp Val Ala
        130                 135                 140

Thr Ser Ser Ser Ala Lys Lys Ala Thr Gly Arg Lys Lys Ser Ser Ser
145                 150                 155                 160

His Asp Ser Gly Thr Asp Ile Thr Ser Val Thr Leu Gly Asp Thr Thr
                165                 170                 175

Ala Val Lys Thr Lys Ile Leu Ile Lys Lys Gly Arg Gly Asn Leu Glu
                180                 185                 190

Lys Thr Asn Leu Asp Leu Gly Pro Thr Ala Pro Ser Leu Glu Lys Glu
            195                 200                 205

Lys Thr Leu Cys Leu Ser Thr Pro Ser Ser Ser Thr Val Lys His Ser
        210                 215                 220

Thr Ser Ser Ile Gly Ser Met Leu Ala Gln Ala Asp Lys Leu Pro Met
225                 230                 235                 240

Thr Asp Lys Arg Val Ala Ser Leu Leu Lys Lys Ala Lys Ala Gln Leu
                245                 250                 255

Cys Lys Ile Glu Lys Ser Lys Ser Leu Lys Gln Thr Asp Gln Pro Lys
                260                 265                 270

Ala Gln Gly Gln Glu Ser Asp Ser Ser Glu Thr Ser Val Arg Gly Pro
            275                 280                 285

Arg Ile Lys His Val Cys Arg Arg Ala Ala Val Ala Leu Gly Arg Lys
        290                 295                 300

Arg Ala Val Phe Pro Asp Asp Met Pro Thr Leu Ser Ala Leu Pro Trp
305                 310                 315                 320

Glu Glu Arg Glu Lys Ile Leu Ser Ser Met Gly Asn Asp Asp Lys Ser
                325                 330                 335

Ser Ile Ala Gly Ser Glu Asp Ala Glu Pro Leu Ala Pro Pro Ile Lys
            340                 345                 350

Pro Ile Lys Pro Val Thr Arg Asn Lys Ala Pro Gln Glu Pro Pro Val
        355                 360                 365

Lys Lys Gly Arg Arg Ser Arg Arg Cys Gly Gln Cys Pro Gly Cys Gln
    370                 375                 380

Val Pro Glu Asp Cys Gly Val Cys Thr Asn Cys Leu Asp Lys Pro Lys
385                 390                 395                 400

Phe Gly Gly Arg Asn Ile Lys Lys Gln Cys Cys Lys Met Arg Lys Cys
                405                 410                 415

Gln Asn Leu Leu Gln Trp Met Pro Ser Lys Ala Tyr Leu Gln Lys Gln
            420                 425                 430

Ala Lys Ala Val Lys Lys Lys Glu Lys Lys Ser Lys Thr Ser Glu Lys
        435                 440                 445

Lys Asp Ser Lys Glu Ser Ser Val Val Lys Asn Val Val Asp Ser Ser
    450                 455                 460
```

-continued

```
Gln Lys Pro Thr Pro Ser Ala Arg Glu Asp Pro Ala Pro Lys Lys Ser
465                 470                 475                 480

Ser Ser Glu Pro Pro Pro Arg Lys Pro Val Glu Glu Lys Ser Glu Glu
                485                 490                 495

Gly Asn Val Ser Ala Pro Gly Pro Glu Ser Lys Gln Ala Thr Thr Pro
                500                 505                 510

Ala Ser Arg Lys Ser Ser Lys Gln Val Ser Gln Pro Ala Leu Val Ile
                515                 520                 525

Pro Pro Gln Pro Pro Thr Thr Gly Pro Pro Arg Lys Glu Val Pro Lys
530                 535                 540

Thr Thr Pro Ser Glu Pro Lys Lys Lys Gln Pro Pro Pro Glu Ser
545                 550                 555                 560

Gly Pro Glu Gln Ser Lys Gln Lys Lys Val Ala Pro Arg Pro Ser Ile
                565                 570                 575

Pro Val Lys Gln Lys Pro Lys Glu Lys Glu Lys Pro Pro Pro Val Asn
                580                 585                 590

Lys Gln Glu Asn Ala Gly Thr Leu Asn Ile Leu Ser Thr Leu Ser Asn
                595                 600                 605

Gly Asn Ser Ser Lys Gln Lys Ile Pro Ala Asp Gly Val His Arg Ile
                610                 615                 620

Arg Val Asp Phe Lys Phe Val Tyr Cys Gln Val Cys Cys Glu Pro Phe
625                 630                 635                 640

His Lys Phe Cys Leu Glu Glu Asn Glu Arg Pro Leu Glu Asp Gln Leu
                645                 650                 655

Glu Asn Trp Cys Cys Arg Arg Cys Lys Phe Cys His Val Cys Gly Arg
                660                 665                 670

Gln His Gln Ala Thr Lys Gln Leu Leu Glu Cys Asn Lys Cys Arg Asn
                675                 680                 685

Ser Tyr His Pro Glu Cys Leu Gly Pro Asn Tyr Pro Thr Lys Pro Thr
                690                 695                 700

Lys Lys Lys Lys Val Trp Ile Cys Thr Lys Cys Val Arg Cys Lys Ser
705                 710                 715                 720

Cys Gly Ser Thr Thr Pro Gly Lys Gly Trp Asp Ala Gln Trp Ser His
                725                 730                 735

Asp Phe Ser Leu Cys His Asp Cys Ala Lys Leu Phe Ala Lys Gly Asn
                740                 745                 750

Phe Cys Pro Leu Cys Asp Lys Cys Tyr Asp Asp Asp Tyr Glu Ser
                755                 760                 765

Lys Met Met Gln Cys Gly Lys Cys Asp Arg Trp Val His Ser Lys Cys
770                 775                 780

Glu Asn Leu Ser Asp Glu Met Tyr Glu Ile Leu Ser Asn Leu Pro Glu
785                 790                 795                 800

Cys Val Ala Tyr Thr Cys Val Asn Cys Thr Glu Arg His Pro Ala Glu
                805                 810                 815

Trp Arg Leu Ala Leu Glu Lys Glu Leu Gln Ile Ser Leu Lys Gln Val
                820                 825                 830

Leu Thr Ala Leu Leu Asn Ser Arg Thr Thr Ser His Leu Leu Arg Tyr
                835                 840                 845

Arg Gln Leu Pro Ser Ser Arg Leu Lys Ser Arg Asp Arg Gly Glu Tyr
                850                 855                 860

Thr Phe Pro Gln Leu Pro Arg Arg Pro Asp Pro Pro Val Leu Thr Glu
865                 870                 875                 880

Val Ser Lys Gln Asp Asp Gln Gln Pro Leu Asp Leu Glu Gly Val Lys
```

-continued

```
                    885                 890                 895
Arg Lys Met Asp Gln Gly Asn Tyr Thr Ser Val Leu Glu Phe Ser Asp
                900                 905                 910
Asp Ile Val Lys Ile Ile Gln Ala Ala Ile Asn Ser Asp Gly Gly Gln
            915                 920                 925
Pro Glu Ile Lys Lys Ala Asn Ser Met Val Lys Ser Phe Phe Ile Arg
        930                 935                 940
Gln Met Glu Arg Val Phe Pro Trp Phe Ser Val Lys Lys Ser Arg Phe
945                 950                 955                 960
Trp Glu Pro Asn Lys Val Ser Ser Asn Ser Gly Met Leu Pro Asn Ala
                965                 970                 975
Val Leu Pro Pro Ser Leu Asp His Asn Tyr Ala Gln Trp Gln Glu Arg
            980                 985                 990
Glu Glu Asn Ser His Thr Glu Gln Pro Pro Leu Met Lys Lys Ile Ile
        995                 1000                1005
Pro Ala Pro Lys Pro Lys Gly Pro Gly Glu Pro Asp Ser Pro Thr Pro
    1010                1015                1020
Leu His Pro Pro Thr Pro Pro Ile Leu Ser Thr Asp Arg Ser Arg Glu
1025                1030                1035                1040
Asp Ser Pro Glu Leu Asn Pro Pro Gly Ile Glu Asp Asn Arg Gln
                1045                1050                1055
Cys Ala Leu Cys Leu Thr Tyr Gly Asp Asp Ser Ala Asn Asp Ala Gly
            1060                1065                1070
Arg Leu Leu Tyr Ile Gly Gln Asn Glu Trp Thr His Val Asn Cys Ala
        1075                1080                1085
Leu Trp Ser Ala Glu Val Phe Asp Asp Gly Ser Leu Lys Asn
    1090                1095                1100
Val His Met Ala Val Ile Arg Gly Lys Gln Leu Arg Cys Glu Phe Cys
1105                1110                1115                1120
Gln Lys Pro Gly Ala Thr Val Gly Cys Cys Leu Thr Ser Cys Thr Ser
                1125                1130                1135
Asn Tyr His Phe Met Cys Ser Arg Ala Lys Asn Cys Val Phe Leu Asp
            1140                1145                1150
Asp Lys Lys Val Tyr Cys Gln Arg His Arg Asp Leu Ile Lys Gly Glu
        1155                1160                1165
Val Val Pro Glu Asn Gly Phe Glu Val Phe Arg Arg Val Phe Val Asp
    1170                1175                1180
Phe Glu Gly Ile Ser Leu Arg Arg Lys Phe Leu Asn Gly Leu Glu Pro
1185                1190                1195                1200
Glu Asn Ile His Met Met Ile Gly Ser Met Thr Ile Asp Cys Leu Gly
                1205                1210                1215
Ile Leu Asn Asp Leu Ser Asp Cys Glu Asp Lys Leu Phe Pro Ile Gly
            1220                1225                1230
Tyr Gln Cys Ser Arg Val Tyr Trp Ser Thr Thr Asp Ala Arg Lys Arg
        1235                1240                1245
Cys Val Tyr Thr Cys Lys Ile Val Glu Cys Arg Pro Pro Val Val Glu
    1250                1255                1260
Pro Asp Ile Asn Ser Thr Val Glu His Asp Glu Asn Arg Thr Ile Ala
1265                1270                1275                1280
His Ser Pro Thr Ser Phe Thr Glu Ser Ser Lys Glu Ser Gln Asn
                1285                1290                1295
Thr Ala Glu Ile Ile Ser Pro Pro Ser Pro Asp Arg Pro Pro His Ser
            1300                1305                1310
```

```
Gln Thr Ser Gly Ser Cys Tyr Tyr His Val Ile Ser Lys Val Pro Arg
    1315                1320                1325

Ile Arg Thr Pro Ser Tyr Ser Pro Thr Gln Arg Ser Pro Gly Cys Arg
    1330                1335                1340

Pro Leu Pro Ser Ala Gly Ser Pro Thr Pro Thr Thr His Glu Ile Val
1345                1350                1355                1360

Thr Val Gly Asp Pro Leu Leu Ser Ser Gly Leu Arg Ser Ile Gly Ser
                1365                1370                1375

Arg Arg His Ser Thr Ser Ser Leu Ser Pro Gln Arg Ser Lys Leu Arg
            1380                1385                1390

Ile Met Ser Pro Met Arg Thr Gly
        1395                1400

(2) INFORMATION FOR SEQ ID NO:8:

(i) SEQUENCE CHARACTERISTICS:
        (A) LENGTH: 436 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

Lys Asn Glu Pro Lys Met Asp Asn Cys His Ser Val Ser Arg Val Lys
    1               5                   10                  15

Thr Gln Gly Gln Asp Ser Leu Glu Ala Gln Leu Ser Ser Leu Glu Ser
                    20                  25                  30

Ser Arg Arg Val His Thr Ser Thr Pro Ser Asp Lys Asn Leu Leu Asp
                35                  40                  45

Thr Tyr Asn Thr Glu Leu Leu Lys Ser Asp Ser Asp Asn Asn Asn Ser
    50                  55                  60

Asp Asp Cys Gly Asn Ile Leu Pro Ser Asp Ile Met Asp Phe Val Leu
    65                  70                  75                  80

Lys Asn Thr Pro Ser Met Gln Ala Leu Gly Glu Ser Pro Glu Ser Ser
                    85                  90                  95

Ser Ser Glu Leu Leu Asn Leu Gly Glu Gly Leu Gly Leu Asp Ser Asn
                    100                 105                 110

Arg Glu Lys Asp Met Gly Leu Phe Glu Val Phe Ser Gln Gln Leu Pro
                115                 120                 125

Thr Thr Glu Pro Val Asp Ser Ser Val Ser Ser Ile Ser Ala Glu
        130                 135                 140

Glu Gln Phe Glu Leu Pro Leu Glu Leu Pro Ser Asp Leu Ser Val Leu
    145                 150                 155                 160

Thr Thr Arg Ser Pro Thr Val Pro Ser Gln Asn Pro Ser Arg Leu Ala
                    165                 170                 175

Val Ile Ser Asp Ser Gly Glu Lys Arg Val Thr Ile Thr Glu Lys Ser
                    180                 185                 190

Val Ala Ser Ser Glu Ser Asp Pro Ala Leu Leu Ser Pro Gly Val Asp
                195                 200                 205

Pro Thr Pro Glu Gly His Met Thr Pro Asp His Phe Ile Gln Gly His
                210                 215                 220

Met Asp Ala Asp His Ile Ser Ser Pro Cys Gly Ser Val Glu Gln
    225                 230                 235                 240

Gly His Gly Asn Asn Gln Asp Leu Thr Arg Asn Ser Ser Thr Pro Gly
                    245                 250                 255
```

-continued

```
Leu Gln Val Pro Val Ser Pro Thr Val Pro Ile Gln Asn Gln Lys Tyr
            260                 265                 270

Val Pro Asn Ser Thr Asp Ser Pro Gly Pro Ser Gln Ile Ser Asn Ala
        275                 280                 285

Ala Val Gln Thr Thr Pro Pro His Leu Lys Pro Ala Thr Glu Lys Leu
        290             295                 300

Ile Val Val Asn Gln Asn Met Gln Pro Leu Tyr Val Leu Gln Thr Leu
305                 310                 315                 320

Pro Asn Gly Val Thr Gln Lys Ile Gln Leu Thr Ser Ser Val Ser Ser
                325                 330                 335

Thr Pro Ser Val Met Glu Thr Asn Thr Ser Val Leu Gly Pro Met Gly
            340                 345                 350

Gly Gly Leu Thr Leu Thr Thr Gly Leu Asn Pro Ser Leu Pro Thr Ser
        355             360                 365

Gln Ser Leu Phe Pro Ser Ala Ser Lys Gly Leu Leu Pro Met Ser His
    370             375                 380

His Gln His Leu His Ser Phe Pro Ala Ala Thr Gln Ser Ser Phe Pro
385             390                 395                 400

Pro Asn Ile Ser Asn Pro Pro Ser Gly Leu Leu Ile Gly Val Gln Pro
                405             410                 415

Pro Pro Asp Pro Gln Leu Leu Val Ser Glu Ser Ser Gln Arg Thr Asp
            420                 425                 430

Leu Ser Thr Thr
            435
```

COMPOSITIONS AND METHODS FOR DETECTING GENE REARRANGEMENTS AND TRANSLOCATIONS

This application is a divisional of U.S. Ser. No. 08/080,255, filed Jun. 17, 1993, now issued as U.S. Pat. No. 5,487,970 which is a continuation-in-part of U.S. Ser. No. 07/900,689, filed Jun. 17, 1992, now abandoned. The entire text of each of the above-referenced disclosures is specifically incorporated by reference herein without disclaimer.

The government owns rights in the present invention pursuant to grants CA42557, CA40046, CA38725, CA34775, 5T32 CA09566 and 5T32 CA09273-12 from the National Institutes of Health and DE-FG02-86ER60408 from the Department of Energy.

BACKGROUND OF THE INVENTION

1. Field of the Invention

The present invention relates generally to the diagnosis of cancer. The invention concerns the creation of probes for use in diagnosing and monitoring certain genetic abnormalities, including those found in leukemia and lymphoid, using molecular biological hybridization techniques. In particular, it concerns the localization of the translocations breakpoints on the MLL gene, the identification of nucleic acid probes capable of detecting rearrangements in all patients with the common 11q23 translocations and the identification of MLL mRNA transcripts characteristic of leukemic cells. MLL fusion proteins and anti-MLL antibodies are also disclosed.

2. Description of the Related Art

The etiology of a substantial portion of human diseases lies, at least in part, with genetic factors. The identification and detection of genetic factors associated with particular diseases or malformations provides a means for diagnosis and for planning the most effective course of treatment. For some conditions, early detection may allow prevention or amelioration of the devastating courses of the particular disease.

The genetic material of an organism is located within one or more microscopically visible entities termed chromosomes. In higher organisms, such as man, chromosomes contain the genetic material DNA and also contain various proteins and RNA. The study of chromosomes, termed cytogenetics, is often an important aspect of disease diagnosis. One class of genetic factors which lead to various disease states are chromosomal aberrations, i.e., deviations in the expected number and/or structure of chromosomes for a particular species or for certain cell types within a species.

There are several classes of structural aberrations which may involve either the autosomal or sex chromosomes, or a combination of both. Such aberrations may be detected by noting changes in chromosome morphology, as evidenced by band patterns, in one or more chromosomes. Normal phenotypes may be associated with rearrangements if the amount of genetic material has not been altered, however, physical or mental anomalies result from chromosomal rearrangements where there has been a gain or loss of genetic material. Deletions, or deficiencies, refer to loss of part of a chromosome, whereas duplication refers to addition of material to chromosomes. Duplication and deficiency of genetic material can be produced by breakage of chromosomes, by errors during DNA synthesis, or as a consequence of segregation of other rearrangements into gametes.

Translocations are interchromosomal rearrangements effected by breakage and transfer of part of chromosomes to different locations. In reciprocal translocations, pieces of chromosomes are exchanged between two or more chromosomes. Generally, the exchanges of interest are between non-homologous chromosomes. If all the original genetic material appears to be preserved, this condition is referred to as balanced. Unbalanced forms have duplications or deficiencies of genetic material associated with the exchange; that is, some material has been gained or lost in the process.

One of the most interesting associations between chromosomal aberrations and human disease is that between chromosomal aberrations and cancer. Non-random translocations involving chromosome 11 band q23 occur frequently in both myeloid and lymphoblastic leukemias (Rowley, 1990b; Heim & Mitelman, 1987). The four most common reciprocal translocations are t(4;11) and t(11;19), which exhibit mainly lymphoblastic markers and sometimes monocytic markers, or both lymphoblastic and monoblastic markers; and t(61;11) and t(9;11), which are mainly found in monoblastic and/or myeloblastic leukemias (Mitelman et al., 1991). Other chromosomes which are involved in recurring translocations with this band in acute leukemias are chromosomes X, 1, 2, 10, and 17.

The present inventors have previously demonstrated, by fluorescence in situ hybridization (FISH), that a yeast artificial chromosome (YAC) containing the CD3D and CD3G genes was split in cells with the four most common translocations (Rowley et al., 1990). Further studies led the inventors to the identification of the gene located at the breakpoint, which was named MLL for mixed lineage leukemia or myeloid/lymphoid leukemia (Ziemin-van Der Poel et al., 1991). The MLL gene has also been independently termed ALL-1 (Cimino et al., 1991; Gu et al., 1992a; b), Htrx (Djabali et al., 1992) and HRX (Tkachuk et al., 1992). The present inventors differentiated the more centromeric MLL rearrangements from the more telomeric breakpoint translocations which involve the RCK locus (Akao et al., 1991b) or the p54 gene (Lu & Yunis, 1992).

From the same YAC clone as described by the present inventors (Rowley et al., 1990), a DNA fragment was obtained which allowed the detection of rearrangements in leukemic cells from certain patients (Cimino et al., 1991; 1992). This 0.7 kilobase DdeI fragment allowed detection of rearrangements in a 5.8 kilobase region in 6 of 7 patients with the t(41;11), 4 of 5 with t(9;11), and 3 of 4 with the t(11;19) translocations (Cimino et al., 1992). Combining these results with those from a subsequent series including an additional 14 patients, the DdeI fragment probe was found to detect rearrangements in 26 of 30 cases with t(41;11), t(91;11) and t(11;19) translocations (Cimino et al., 1991; 1992), which represents an overall detection rate of 87%. Despite this partial success, the failure of the DdeI probe to detect all rearrangements is a significant drawback to its use in clinical diagnosis.

Accordingly, prior to the present invention, there remained a particular need for the identification of nucleic acid fragments or probes capable of detecting leukemic cells from all patients with the common 11q23 translocations. The creation of such probes which may be used in both Southern blot analyses and in FISH with either dividing leukemic cells or interphase nuclei would be particularly important. The elucidation of further information regarding the MLL gene, such as further sequence data and information regarding transcription into mRNA, would also be advantageous, as would the identification of nucleic acid fragments capable of differentiating MLL mRNA transcripts from normal and leukemic cells.

SUMMARY OF THE INVENTION

The present invention seeks to overcome these and other drawbacks inherent in the prior art by providing improved compositions and methods for the diagnosis, and continued monitoring, of various types of leukemias, particularly myeloid and lymphoid leukemia, and lymphomas in humans. This invention particularly provides novel and improved probes for use in genetic analyses, for example, in Southern and Northern blotting and in fluorescence in situ hybridization (FISH) using either dividing leukemic cells or interphase nuclei.

The inventors first localized the translocations breakpoint on the MLL gene to within an estimated 9 kb BamHI genomic region of the MLL gene, and later sequenced this region and found it to be 8.3 kb in size. They have further identified short nucleic acid probes, as exemplified by a breakpoint-spanning 0.7 kb BamH1 cDNA fragment, which detect rearrangements on Southern blot analysis of singly-digested DNA in all patients with the common 11q23 translocations, namely t(41;11), t(6;11), t(91;11), and t(11;19), and also in certain patients with other rare 11q23 anomalies. The use of this novel nucleic acid probe represents a significant advantage over previously described probes which allowed the molecular diagnosis of leukemia only in certain cases of common 11q23 translocations, and not in all cases.

The invention also provides probe compositions for use in Northern blot analyses and methods for identifying leukemic cells from the pattern of MLL mRNA transcripts present, which are herein shown to be different in leukemic cells as opposed to normal cells.

The present invention generally concerns the breakpoint-spanning gene named MLL, and this term is used throughout the present text. MLL is the accepted designation for this gene adopted by the human genome nomenclature committee (Chromosome Co-ordinating Meeting, 1992), however, other terms are also in current use to describe the same gene. For example, the terms ALL-1 (Cimino et al., 1991, Gu et al., 1992a; b), Htrx (Djabali et al., 1992) and HRX (Tkachuk et al., 1992) are also currently employed as names for the MLL gene. As these terms in fact refer to the same gene, i.e., to the MLL gene, each of the foregoing ALL-1, Htrx and HRX 'genes' are encompassed by the present invention and are described herein, for simplicity, by the single term "MLL".

In certain embodiments, the invention concerns a method for detecting leukemic cells containing 11q23 chromosome translocations that involve MLL, which method comprises obtaining nucleic acids from cells suspected of containing a leukemia-associated chromosomal rearrangement at chromosome 11q23, and probing said nucleic acids with a probe capable of differentiating between the nucleic acids from normal cells and the nucleic acids from leukemic cells. To "differentiate between the nucleic acids from normal cells and the nucleic acids from leukemic cells" will generally require using a probe, such as those disclosed herein, which allows MLL DNA or RNA from normal cells to be identified and differentiated from MLL DNA or RNA from leukemic cells by criteria such as, e.g., number, pattern, size or location of the MLL nucleic acids.

The cells suspected of containing a chromosomal rearrangement at chromosome 11q23 may be cells from cell lines or otherwise transformed or cultured cells. Alternatively, they may be cells obtained from an individual suspected of having a leukemia associated with an 11q23 chromosome translocation, or cells from a patient known to be presently or previously suffering from such a disorder.

The nucleic acids obtained for analysis may be DNA, and preferably, genomic DNA, which may be digested with one or more restriction enzymes and probed with a nucleic acid probe capable of detecting DNA rearrangements from leukemic cells containing 11q23 chromosome translocations. Techniques such as these are based upon 'Southern blotting' and are well known in the art (for example, see Sambrook et al. (1989), incorporated herein by reference). A large battery of restriction enzymes are commercially available and the conditions for Southern blotting are described hereinbelow, suitable modifications of which will be known to those skilled in the art of molecular biology.

Preferred nucleic acid probes for use in Southern blotting to detect leukemic cells containing 11q23 chromosome translocations are those probes which include a sequence in accordance with the sequence of a 0.7 kb BamH1 fragment of the CDNA clone 14P-18B derived from the MLL gene, and more preferably, will be the probe MLL 0.7B (seq id no:1) itself. The use of this probe is particularly advantageous as this fragment encompasses the breakpoints clustered in the 8.3 kb BamH1 genomic region (seq id no:6) of the MLL gene and allows the detection of all the common 11q23 translocations. Moreover, using MLL 0.7B (also simply referred to as 0.7B) presents the added advantage that DNA may be digested with only a single restriction enzyme, namely BamH1. Probe MLL 0.7B (seq id no:1) is derived from a cDNA clone that lacks Exon 8 sequences, but this clearly has no adverse effects on breakpoint detection using this probe.

Patients' or cultured cells may also be analyzed for the presence of 11q23 chromosome translocations by obtaining RNA, and preferably, mRNA, from the cells and probing the RNA with a nucleic acid probe capable of differentiating between the MLL mRNA species in normal and leukemic cells. This differentiation will generally involve using a probe capable of identifying normal MLL gene transcripts and aberrant MLL gene transcripts, wherein a reduction in the amount of a normal MLL gene transcript, such as those estimated to be about 12.5 kb, 12.0 kb or 11.5 kb in length, or the presence of an aberrant MLL gene transcript, not detectable in normal cells, will be indicative of a cell containing a 11q23 chromosome translocation. Techniques of detecting and characterizing mRNA transcripts, based upon Northern blotting, are described herein and suitable modifications will be known to those of skill in the art (e.g., see Sambrook et al., 1989).

It is important to note that throughout this text the size of certain transcripts quoted are estimated measurements from Northern blot analyses. It is well known in the art that agarose gel resolution of RNA species of about 9 to 10 kb in size, or greater, leads to an approximate size determination, especially with sizes of greater than about 10 kb. Hence, size determinations made initially by this technique may later be found to be over- or under-estimates of the true size of a given transcript. For example, the MLL translocation breakpoint was first localized to an estimated 9 kb BamHI genomic region which the inventors later found, by sequencing, to be 8.3 kb in size. It is possible that the estimated sizes of the larger mRNA transcripts may differ as much as about 2 kb up to about 3 kb from their size determined by sequencing, and that the 12.5 kb to 11 kb size range may be more accurately represented by a 15 kb to 13 kb size range. This general phenomenon has been observed before in regard to the MLL gene itself (e.g., Cimino et al., 1991; 1992).

Using the probes of this invention, a reduction in the amount of MLL gene transcripts estimated to be of about 12.5 kb, 12.0 or 11.5 kb in length (or about 15–13 kb), as compared to the level of such transcripts in normal cells, is indicative of cells which contain a 11q23 chromosome translocation. The size of aberrant MLL transcripts will naturally vary between the individual cell lines and patients' cells examined, but will nevertheless always be distinguishable from the size and pattern of MLL transcripts identified by the same probe(s) in normal cells.

In RS4;11 cells, the specific rearranged mRNA transcripts identified as characteristic of leukemic cells are estimated to be of about 11.5 kb, 11.25 kb or 11.0 kb in length, and so an elevation in the levels of such transcripts is indicative of a cell containing an 11q23 chromosome translocation. In the Karpas 45 cell line (K45 t(X;11)(q13;q23)), the aberrant mRNA transcripts have estimated sizes of about 8 kb and about 6 kb, which are therefore another example of transcripts characteristic of leukemic cells. In any event, it will be clear that using the probes of the present invention one may differentiate between normal and leukemic cell transcripts, and thus identify leukemic cells in an assay or screening protocol, regardless of the actual size and pattern of the aberrant transcripts themselves.

Probes preferred for use in analyzing mRNA transcripts in order to identify cells with an 11q23 chromosome translocation, i.e., for use in Northern blotting detection, are contemplated to be those based upon the cDNA clones 14P-18B (seq id no:4) and 14-7 (seq id no:5). In such Northern blotting detection, the use of cDNA clone 14-7 itself (seq id no:5) and various fragments of clone 14P-18B (seq id no:4) is contemplated. The use of 14P-18B fragments in Northern blotting is generally preferred, with the nucleic acid fragments termed MLL 0.7B (0.7B, seq id no:1), MLL 0.3BE (0.3BE, seq id no:2) and MLL 1.5EB (1.5BE, seq id no:3) being particularly preferred.

The use of a combination of the probes described above may provide further advantages in certain cases as it may allow the differentiation of further distinct MLL gene transcripts. An example of this is presented herein in the case of the RS41;11 cell line. Here, it is demonstrated herein that normal cells contain an MLL gene transcript of estimated length 11.5 kb and that RS4;11 leukemic cells have a reduced amount of this normal transcript (in common with their reduced amount of the 12.5 kb and 12.0 kb normal transcripts). However, the inventors have also determined that the RS41;11 leukemic cells contain an aberrant mRNA transcript, also estimated to be about 11.5 kb in length, which is present in significant quantities and may even be termed over-expressed (a specific increase in the level of an mRNA transcript in comparison to the level in normal cells is indicative of "over-expression").

The probe termed 1.5EB (seq id no:3) is herein shown to detect the normal 11.5 kb transcript, and a weak signal in a Northern blot employing this probe is therefore indicative of a leukemic cell containing an 11q23 chromosome translocation. Each of the more telomeric probes, namely 0.7B, 0.3BE and 14-7, (seq id nos:1, 2, and 5, respectively) are shown to detect the over-expressed, aberrant, 11.5 kb transcript in RS4;11 cells, and a strong signal in a Northern blot employing any of these probes therefore characterizes a leukemic cell with an RS4;11-like translocation. A further advantage of the present invention is, therefore, that in using more than one probe, it provides methods by which to differentiate between normal and aberrant transcripts which may be similar in size, and thus increases the number of factors with which to differentiate between leukemic and normal cells.

The probes of the present invention may also be used to identify leukemic cells containing 11q23 chromosome translocations in situ, that is, without extraction of the genetic material. Fluorescent in situ hybridization (FISH), which allows cell nuclei to be analyzed directly, is one method which is considered to be particularly suitable for use in accordance with the present invention. Cells may be analyzed in metaphase, a stage in cell division wherein the chromosomes are individually distinguishable due to contraction. However, the methods and compositions of the present invention are particularly advantageous in that they are equally suitable for use with interphase cells, a stage wherein chromosomes are so elongated that they are entwined and cannot be individually distinguished.

Cloned DNA probes from both sides of the translocation breakpoint region can be used with FISH to detect the translocation in leukemic cells. In normal cells, these two probes would be together and they would appear as a single signal. In cells with a translocation, the centromeric probe would remain on the derivative 11 chromosome whereas the telomeric probe would be translated to the other derivative chromosome. This would result in two smaller signals, one on each translocation partner. As the inventors have shown that about 30% of patients have a deletion of the MLL gene immediately telomeric to the breakpoint, they have cloned a series of telomeric probes that can be used reliably to detect the translocation in virtually all patients.

Whether employing Southern, blotting, Northern blotting, FISH, or any other amenable techniques, the present invention provides improved methods for analyzing cells from patients suspected of having a leukemia associated with an 11q23 chromosome translocation. In that the probes disclosed herein are able to detect DNA rearrangements in all patients with the common 11q23 translocations, i.e., there are no false-negatives, their use represents a significant advance in the art.

This invention will be particularly useful in the analysis of individuals who have already had one malignant disease that has been treated with certain drugs that induce leukemia with 11q23 translocations in 10 to 25% of patients (Ratain & Rowley, 1992). Thus cells from these patients can be monitored with Southern blot analysis, PCR and FISH to detect cells with an 11q23 translocation and thus identify patients very early in the course of their disease. In addition, the probes described in this invention can be used to monitor the response to therapy of leukemia patients known to have an 11q23 translocation. These leukemic cells show a substantial decrease in frequency in response to therapy.

In further embodiments, the present invention concerns compositions comprising nucleic acid segments, and particularly DNA segments, isolated free from total genomic DNA, which have a sequence in accordance with, or complementary to, the sequence of cDNA clone 14P-18B (seq id no:4) or cDNA clone 14-7 (seq id no:5) derived from the MLL gene. Such DNA segments are exemplified by the clones 14P-18B (seq id no:4) and 14-7 (seq id no:5) themselves, and also by various fragments of such sequences. cDNA clones 14P-18B and 14-7 may be characterized as being derived from the MLL gene, as being about 4.1 kb and about 1.3 kb in length, respectively, and as having restriction patterns as indicated in FIG. 1 and FIG. 2.

The invention provides probes which span the MLL breakpoint, e.g., 0.7B; probes centromeric to the breakpoint, e.g., 1.5EB, and probes telomeric to the breakpoint, e.g., 0.3BE, 14-7, and even 0.8E. Particularly preferred DNA segments of the present invention are those DNA segments represented by the nucleic acid fragments, or probes, termed MLL 0.7B (0.7B, seq id no:1), MLL 0.3BE (0.3BE, seq id no:2) and MLL 1.5EB (1.5BE, seq id no:3).

The nucleic acid segments and probes of the present invention are contemplated for use in detecting cells, and particularly, cells from human subjects, which contain an 11q23 chromosome translocation. However, they are not limited to such uses and also have utility in a variety of other embodiments, for example, as probes or primers in nucleic acid hybridization embodiments. The ability of these nucleic acid segments to specifically hybridize to MLL gene-like sequences will enable them to be of use in various assays to detect complementary sequences, other than for diagnostic purposes. The use of such nucleic acid segments as primers for the cloning of further portions of genomic DNA, or for the preparation of mutant species primers, is particularly contemplated. The DNA segments of the invention may also be employed in recombinant expression. For example, as disclosed herein, they have be used in the production of peptides or proteins for further analysis or for antibody generation.

The present invention also embodies kits for use in the detection of leukemic cells containing 11q23 chromosome translocations. Kits for use in both Southern and Northern blotting and in FISH protocols are contemplated, and such kits will generally comprise a first container which includes one or more nucleic acid probes which include a sequence in accordance with the sequences of nucleic acid probes MLL 0.7B (seq id no:1), MLL 0.3BE (seq id no:2), MLL 1.5EB (seq id no:3) or 14-7 (seq id no:5), and a second container which comprises one or more unrelated nucleic acid probes for use as a control. In preferred embodiments, such kits will include one or more of the nucleic acid probes termed MLL 0.7B (seq id no:1), MLL 0.3BE (seq id no:2), MLL 1.5EB (seq id no:3) or 14-7 (seq id no:5) themselves, and kits for use in connection with FISH or Northern blotting will, most preferably, include all such nucleic acid probes or segments.

Kits for the detection of leukemic cells containing 11q23 chromosome translocations by Southern blotting may also include a third container which includes one or more restriction enzymes. Particularly preferred Southern blotting kits will be those which include the nucleic acid probe MLL 0.7B (seq id no:1) and the restriction enzyme BamH1. Naturally, kits for use in connection with FISH will contain one or more nucleic acid probes which are fluorescently labelled.

Further embodiments of the present invention concern MLL peptides, polypeptides, proteins, and fusions thereof and antibodies having binding affinity for such proteins, peptides and fusions. The invention therefore concerns proteins or peptides which include an MLL amino acid sequence, purified relative to their natural state. Such proteins or peptides may contain only MLL sequences themselves or may contain MLL sequences linked to other protein sequences, such as, e.g., 'natural' sequences derived from other chromosomes or portions of 'engineered' proteins such as glutathione-S-transferase (GST), ubiquitin, β-galactosidase and the like.

Proteins prepared in accordance with the invention may include MLL amino acid sequences which are either telomeric or centromeric to the breakpoint region, as exemplified by the amino acid sequences of seq id no:8 and amino acids 323–623 of seq id no:7, respectively. Other proteins which are contemplated to be particularly useful are those including a zinc finger region from seq id no:7, such as those generally located between amino acids 574–1184, and more particularly, those including amino acids 574 to about 810 and about 1057 to 1184 of seq id no:7. Antibodies prepared in accordance with the invention may be directed against any of the 'centromeric' or 'telomeric' proteins described herein, or portions thereof, with antibodies against the zinc finger regions of seq id no:7 being particularly contemplated.

Alignment of cDNA clones of the MLL gene with genomic sequences. The top thick solid line represents the genomic sequence in which not all the restriction sites are indicated. The sizes above the line 14 kb, 8.3 kb and ~20 kb refer to the BamH1 fragments. The two dashed lines located above the 14 kb BamHI genomic fragment indicate the 2.1 kb BamHI/SstI telomeric fragment (14BS), and the 0.8 kb PstI centromeric fragment (14P) used to screen the cDNA library. The solid line under each cDNA clone indicates the region of homology between clones. The predicted direction of transcription of MLL and the open reading frame of clone 14-7 is indicated by the arrow. Restriction enzymes used; B, BamHI; S, SstI; Sa, SalI; P, PstI; H, HindIII; X, XhoI; E, EcoRI; Bg, BglI.

FIG. 2.

A map of cDNA clones 14-7 and 14P-18B. Restriction enzymes are the same as in FIG. 1. The solid lines below the cDNA clones indicate the cDNA fragments used in the Southern and Northern hybridizations. All of clone 14-7, and three adjacent fragments of 0.3 kb BamH1/EcoR1 (MLL 0.3BE), 0.7 kb BamH1 (MLL 0.7B) and 1.5 kb EcoR1/BamH1 (MLL 1.5EB) from cDNA clone 14P-18B were used. Note that the EcoR1 site used to excise the 1.5 kb fragment was a cloning EcoR1 site. The breakpoint region within the 0.7 kb BamH1 fragment is also shown, as is the 0.8 kb EcoRI probe (MLL 0.8E) employed in analyzing the Karaps 45 cell line. It will be noted that the orientation of the probes represented in this figure is reversed to that in sequence 14P-18B (seq id no:4), where MLL 1.5EB is first, MLL 0.7B is next and MLL 0.3BE is last.

FIG. 3.

(scanned images) Southern blot of DNA from cell lines and patient leukemic cells with 11q23 translocations digested with BamHI and hybridized to MLL 0.7B. Lanes 1, 7, control DNA; lane 2, RS4;11 cell line; lanes 3–5, patients 1–3 (as detailed in Table 1), lane 6, Sup-T13 cell line showing weak hybridization to two rearranged bands of 7.0 kb and 1.4 kb, lane 8, RC-K8 cell line. DNA fragment sizes in kilobases are shown on the left.

FIG. 4.

Figure 4A:
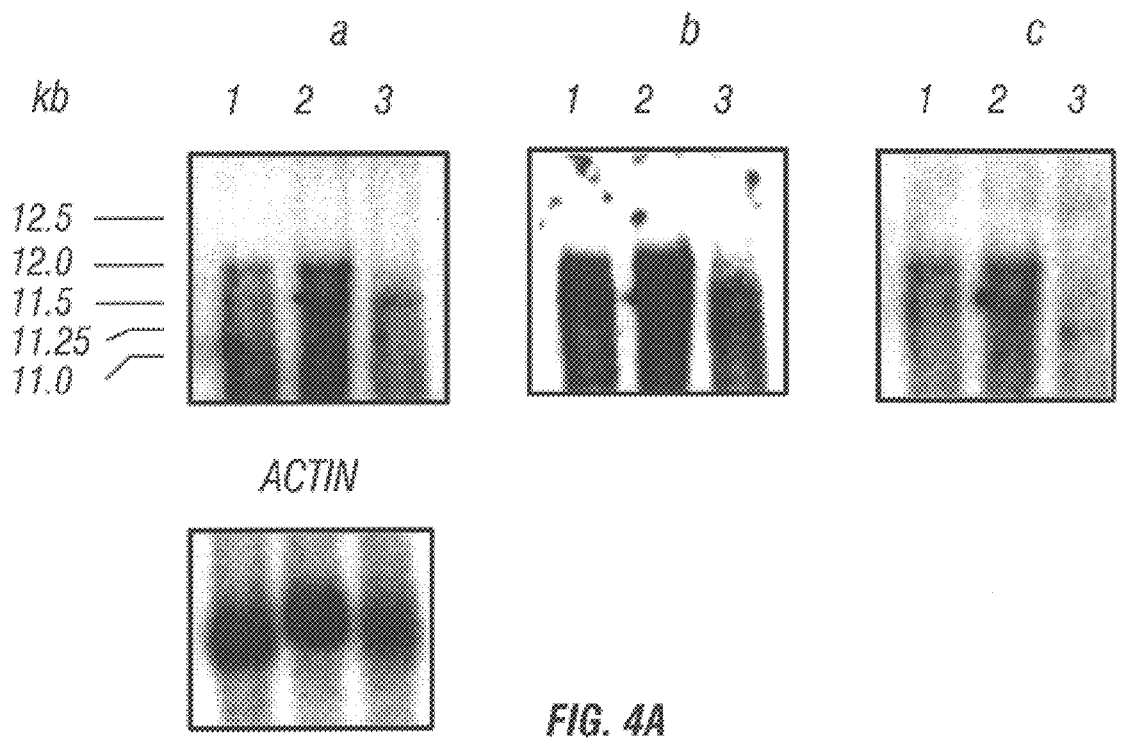
Figure 4B:
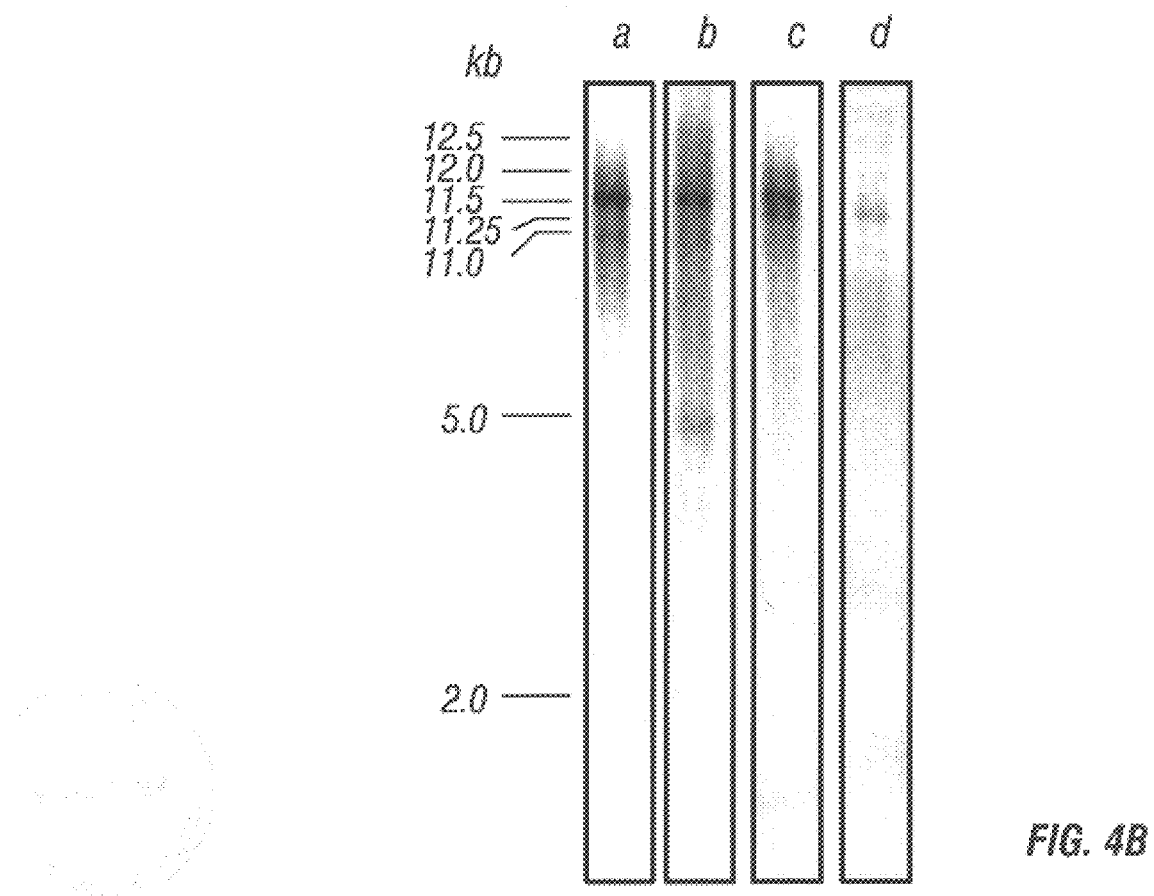

(scanned images) Northern blot analyses of poly(A)$^+$ RNA. Poly(A)$^+$ RNA was isolated from cell lines in logarithmic growth phase except where noted. RNA sizes are indicated on the left. FIG. 4 consists of FIG. 4A and FIG. 4B.

FIG. 4A. (scanned images) Each lane 1 is the RCH-ADD cell line; each lane 2 is the RC-K8 cell line and each lane 3 is the RS4;11 cell line in stationary growth phase. The Northern blots in this panel were hybridized sequentially to the 14-7 probe, (a); the MLL 0.7B probe, (b); and the MLL 1.5EB probe, (c). Hybridization to actin is also shown in this panel in (a).

FIG. 4B. (scanned images) RNA from the RS4;11 cell line. The Northern blots in this panel were hybridized in the same manner to the 14-7 probe, (a); the MLL 0.3BE probe, (b); the MLL 0.7B probe, (c); and the MLL 1.5EB probe, (d).

FIG. 5.

Schematic representation of the Northern blot results obtained from the sequential hybridization of probes (14-7, MLL 0.3BE, MLL 0.7B and MLL 1.5EB) to control (C) and RS41;11 cell line (41;11) RNA. Only the large size transcripts are shown. The solid lines indicate normal sized transcripts of normal mRNA with estimated sizes of 12.5, 12.0 and 11.5 kb which are detected in both control and RS4;11 cell lines. The dashed lines represent the aberrant sized transcripts with estimated sizes of 11.5, 11.25 and 11.0 kb detected in the RS41;11 cell line. In the RS4;11 cell line the normal and altered (estimated) 11.5 kb mRNA transcripts are indicated by an overlapping broken and solid line. The line thickness indicates the strength of the hybridization signal. The chromosomal origin of each transcript is depicted on the right.

FIG. 6.

(scanned images) Southern hybridization of patient DNA digested with BamHI and probed with the 0.7 kilobase BamHI cDNA fragment. Sizes are in kilobases. Lane 1: Normal peripheral white blood cell DNA, Lane 2: AML with t(1;11)(q21;q23), Lane 3: ALL with t(4;11)(q21;q23), Lane 4: ALL with t(4;11)(q21;q23), Lane 5: ALL with t(4;11)(q21;q23), Lane 6: ALL with t(4;11)(q21;q23), Lane 7: ALL with t(41;11)(q21;q23), Lane 8: AML with t(6;11)(q27;q23), Lane 9: AML with t(6;11)(q27;q23), Lane 10: AML with t(9;11)(p22;q23), Lane 11: AML with t(10;11) (p13;q21), Lane 12: Lymphoma with t(11;11)(p15;q22), Lane 13: AML with ins(10;11)(p11;q23q24), Lane 14: AML with ins(10;11)(p13;q21q24), Lane 15: ALL with t(11;19)(q23;p13.3), Lane 16, AML with t(11;19)(q23;p13.3), Lane 17: AML with t(11;22)(q23;q12). A single germline band was detected in normal DNA in lane 1 and in patient samples with non-11q23 breakpoints in lanes 11, 12, and 14. Rearrangements were detected in all other lanes. Lanes 2, 3, 4, 6, 7, 8, 10, 13, 16, 17 had two rearranged bands, and lanes 5, 9, and 15 had one rearranged band.

Figure 7A:
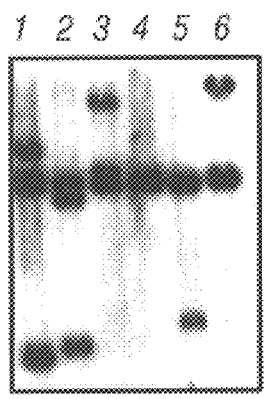
Figure 7B:
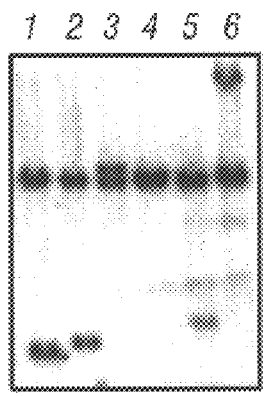
Figure 7C:
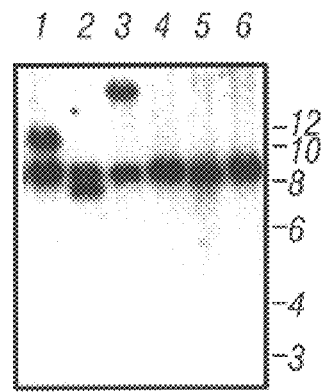

FIGS. 7A, 7B, and 7C (scanned images)

Southern hybridization of leukemic and normal DNA digested with BamHI and probed with the 0.7 kilobase BamHI cDNA fragment and with the centromeric and telomeric PCR-derived probes. Sizes are in kilobases. .

FIG. 7A. DNA probed with 0.7 kilobase cDNA probe. Lane 1: Biphenotypic leukemia with t(11;19)(q23;p13.3), lane 2: ALL with t(11;19)(q23;p13.3), lane 3: AML with t(11;19)(q23;p13.3), lane 4: normal DNA, lane 5: AML with t(6;11)(q27;q23), lane 6: Follicular lymphoma with t(6;11) (p12;q23). A single germline 8.3 kilobase band is identified in normal DNA in lane b and is also present in all other lanes. Two rearranged bands, corresponding to the two derivative chromosomes, are identified in lanes 1, 2, and 3. A single rearranged band is present in lanes 5 and 6.

FIG. 7B: The blot form panel A was stripped and rehybridized with the centromeric PCR probe. The germline 8.3 kilobase band is again present in all lanes. In lanes 1–3, one of the two rearranged bands is detected. In lane 3, the rearranged band is slightly larger than the germline band. In lanes 5 and 6, the single rearranged band is also identified.

FIG. 7C: The blot from panel A was stripped and then rehybridized with the telomeric PCR probe. The germline band is present in all lanes. In lanes 1–3, one of the two rearranged bands is identified. In lane 2, the rearranged band is slightly smaller than the germline band. However, the single rearranged band in lanes 5 and 6 is not detected.

Figure 8A:
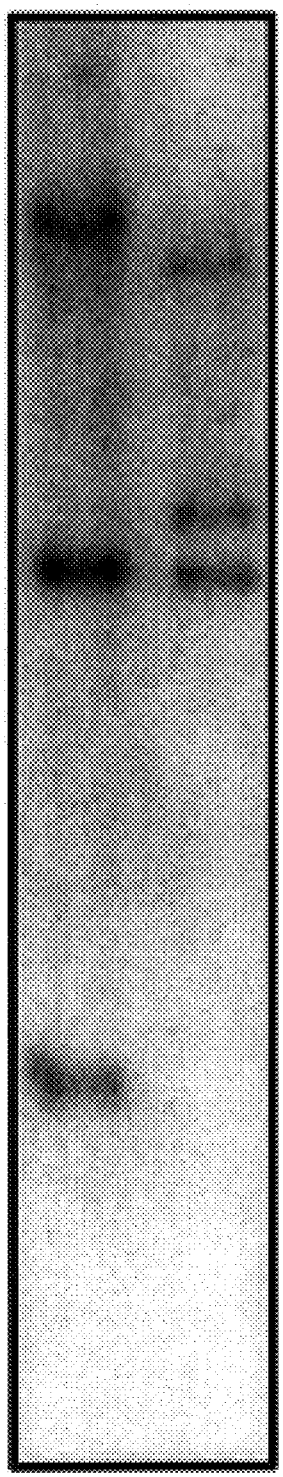
Figure 8B:
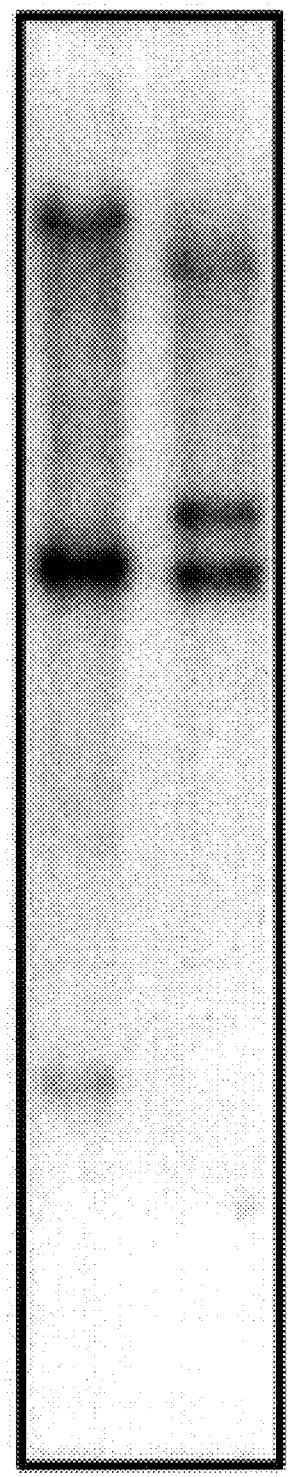
Figure 8C:
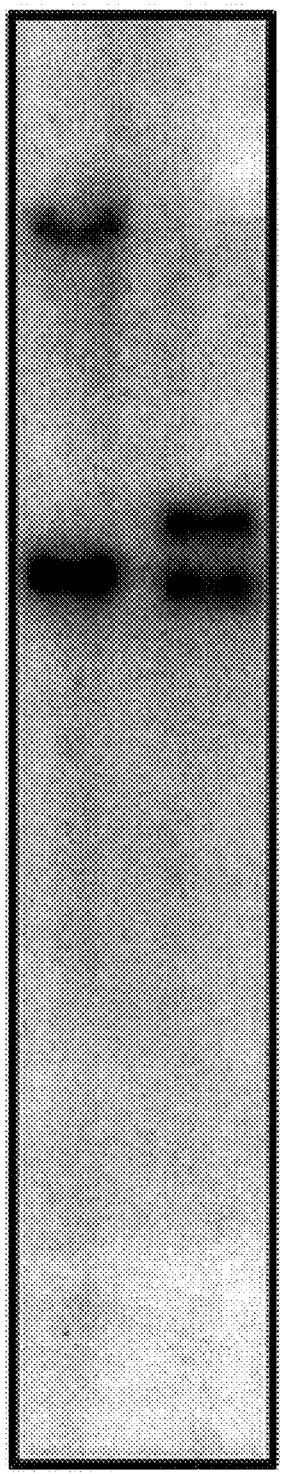

FIGS. 8A, 8B, and 8C (scanned images).

Southern hybridization of patient DNA digested with BamHI and probed with 0.7 kilobase BamHI cDNA fragment and with the centromeric and telomeric PCR-derived probes. Lane 1: AML with t(1;11)(q21;q23)—same patient as in lane 2 of FIG. 7. Lane 2: ALL with t(4;11)(q21;q23)—the same patient as shown in lane 6 of FIG. 7. FIG. 8 consists of FIG. 8A, FIG. 8B and FIG. 8C.

FIG. 8A. DNA probed with the 0.7 kilobase cDNA probe. The germline band and two rearranged bands are present in both lanes.

FIG. 8B. The blot from panel A was stripped and rehybridized with the centromeric PCR probe. The germline band and both rearranged bands are again detected.

FIG. 8C. The blot from panel A was stripped and then rehybridized with the telomeric PCR probe. The germline band and only one of the rearranged bands are detected.

Figure 9:
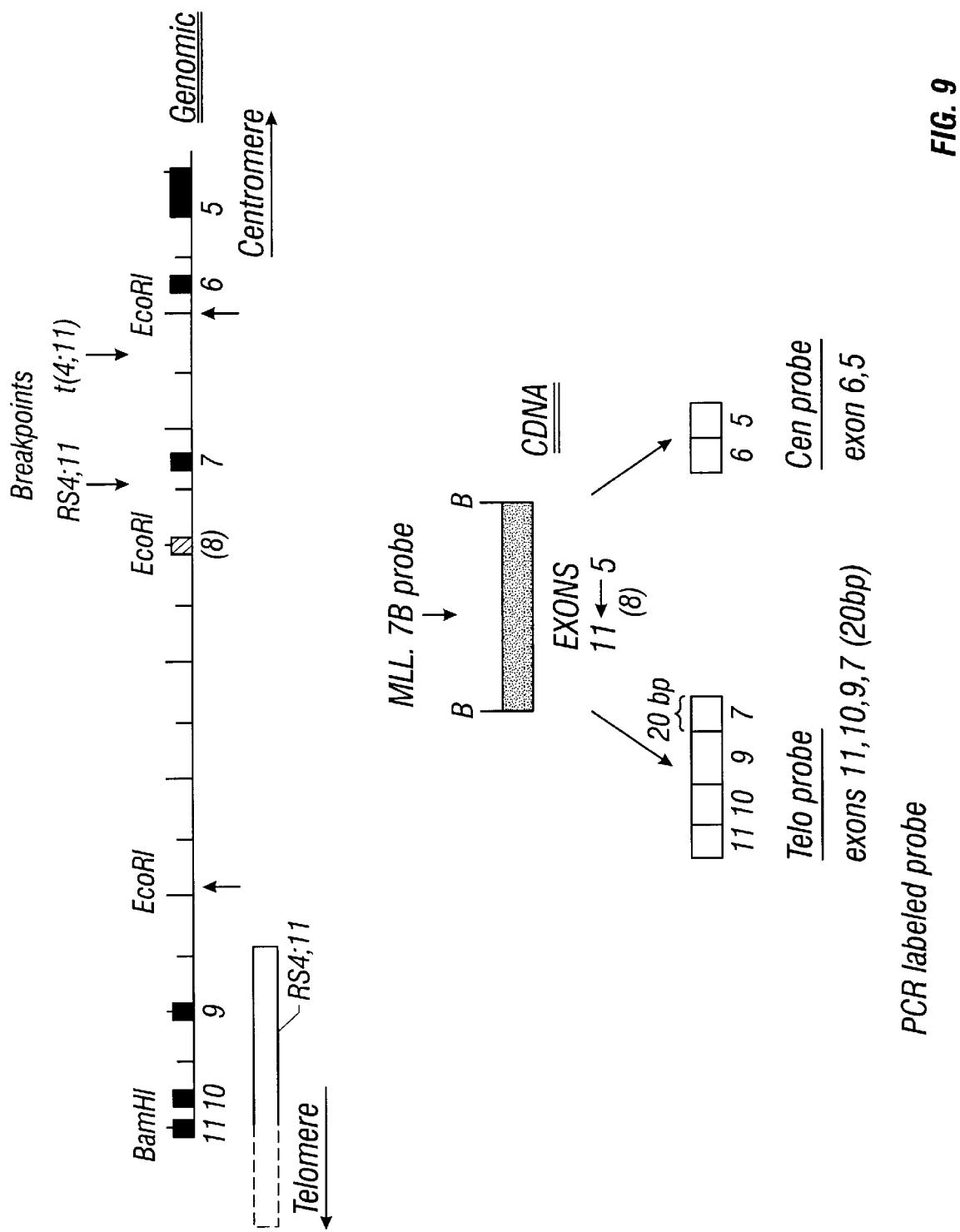

FIG. 9. Representation of the 8.3 kb BamH1 Genomic Section of the MLL gene and Various cDNA Probes.

Figures 10A, 10B:
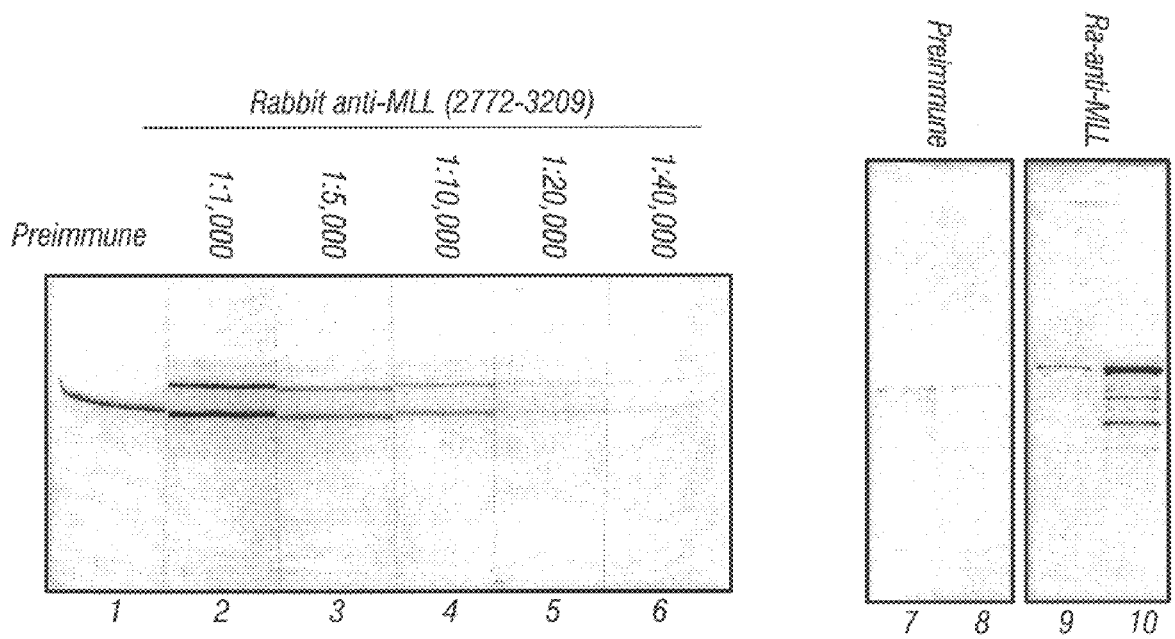

FIGS. 10A and 10B (scanned images). Reactivity of Specific anti-MLL Antisera Directed Against the MLL Amino Acids of Seq Id No:8. Western blots of pre-immune sera (lanes 1, 7 & 8) and high titer rabbit antisera (lanes 2–6, 9 & 19) specific for the MLL portion of the MLL-GST fusion protein. The creation of an expression vector for the production of an MLL amino acid-containing fusion protein containing MLL amino acids of seq id no:8 and GST is described in Example IV.

Figure 11:
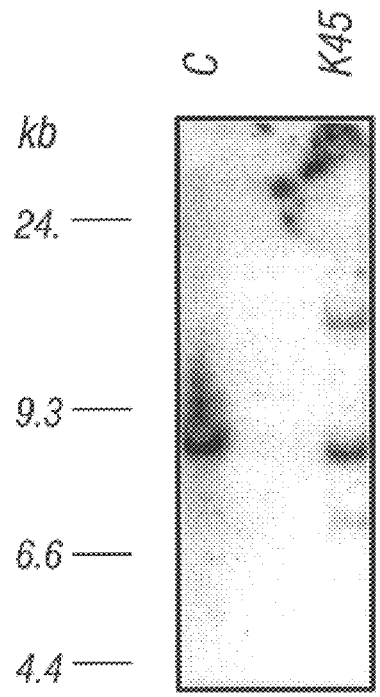

FIG. 11 (scanned images). Southern blot analysis of DNA from human placenta (C) and the Karpas 45 cell line (K45, t(X;11)(q13;q23)) digested with BamH1 and hybridized to the 0.7B cDNA fragment of MLL (seq id no:1). DNA size markers are shown on the left and the lines on the right denote the rearranged DNA bands detected in the Karpas 45 cell line.

Figure 12:
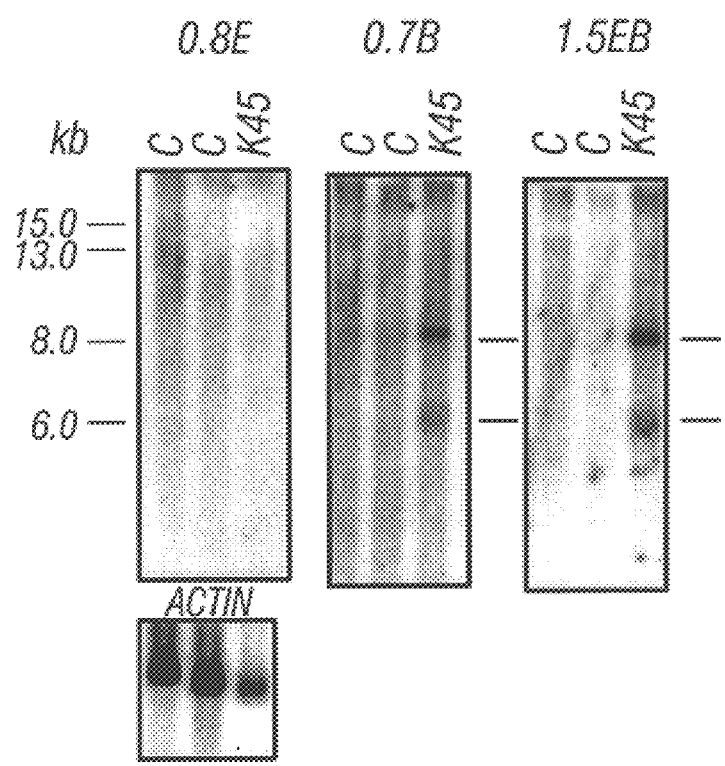

FIG. 12 (scanned images). Northern blot analysis of RNA isolated from two control cell lines RC-K8 (C) and RCH-ADD (C) and the Karpas 45 cell line (K45) with a t(X;11) (q13;q23) translocation. The blot was sequentially hybridized to the 0.8E, 0.7B and 1.5EB cDNA fragments of the MLL gene. Hybridization to actin is also shown. The markers on the right denote the size of the detected transcripts, and the lines to the right of the blots locate the altered MLL transcripts seen in the Karpas 45 cell line.

DETAILED DESCRIPTION OF THE PREFERRED EMBODIMENTS

Introduction

The molecular analysis of recurring structural chromosome abnormalities in human neoplasia has led to the identification of a number of genes involved in these rearrangements. These genetic alterations are implicated in the development of malignancies. For example, in chronic myelogenous leukemia, the proto-oncogene ABL is translocated from chromosome 9 to the BCR gene on chromosome 22 leading to the generation of a chimeric gene and a fusion protein (Rowley, 1990b). In lymphoid malignancies, translocations frequently involve the immunoglobulin or T-cell receptor genes which are juxtaposed to key oncogenes causing their abnormal expression (Rowley, 1990a).

Translocations involving chromosome band 11q23 have been identified as a frequent cytogenetic abnormality in lymphoid and myeloid leukemias and in lymphomas (Sandberg, 1990). In addition to leukemias that occur de novo, 11q23 translocations are also observed in therapy related leukemias. The t(4;11) has been reported in 2% to 7% of all cases of acute lymphoblastic leukemia (ALL) and in up to 60% of leukemias in children under the age of one year (Parkin et al., 1982; Pui et al., 1991; Kaneko et al., 1988). By French-American-British (FAB) Cooperative Group criteria, these leukemias are usually classified morphologically as L1. Typically, these patients express myeloid or monocytoid markers in addition to the B-cell lymphoid markers (Kaneko et al., 1988; Drexler et al., 1991). On flow cytometry, a characteristic phenotype, CD 10⁻, CD 15⁺, CD 19⁺, CD 24⁻/⁺, has been reported (Pui et al., 1991). These patients of ten present with hyperleukocytosis and early central nervous system involvement (Arthur et al., 1982).

The t(11;19) is more complex because two translocations involving different breakpoints in 19p with different phenotypic features have been identified. Approximately two-thirds have a t(11;19) (q23;p3.3) and include patients with ALL, biphenotypic leukemia, and infants or young children with AML. One-third have a t(11;19) (q23;p13.1) and are generally older children or adults with AML-M4 an d M5. The t(4;11) and the t(11;19) have been recognized as a cytogenetic subset in ALL with a poor prognosis (Gibbons et al., 1990).

Translocations involving 11q23 are frequent in acute myeloid leukemia (AML) and have also been found to occur preferentially in childhood (Fourth Int. Wksh. *Cancer Gent. Cytogenet.*, 1984). The t(91;11) and both t(11;19) are the most common, but other rearrangements, such as the t(6;11), an insertion (10;11), and deletions involving 11q23 have also been reported (Mitelman et al., 1991). Morphologically these cases are usually categorized as acute myelomonocytic leukemia (AML-M4) or acute monoblastic leukemia (AML-M5) by FAB criteria. Similar to ALL, these patients often present with high leukemic blast cell counts. 11q23 abnormalities have generally been considered to carry a poor prognosis in AML (Fourth Int. Wksh. *Cancer Genet. Cytogenet.*, 1984). However, the use of intensive chemotherapy in these patients has led to complete remission rates and remission durations that are similar to a group with favorable cytogenetic abnormalities (Samuels et al., 1988). Many cases of AML with 11q23 anomalies have been found, by flow cytometry, to express lymphoid markers (Cuneo et al., 1992).

Abnormalities of 11q23 have been found to be common in both the lymphoid and myeloid leukemias as well as in biphenotypic leukemias which have both lymphoid and myeloid features (Hudson et al., 1991). This has led to the hypothesis that rearrangements of a gene at 11q23 may affect a pluripotential progenitor cell capable of either myeloid or lymphoid differentiation. Alternatively, a mechanism for differentiation that is shared by both lymphoid and myelo-monocytic stem cells may be deregulated as a consequence of these translocations.

DNA Segments and Nucleic Acid Hybridization

As used herein, the term "DNA segment" in intended to refer to a DNA molecule which has been isolated free of total genomic DNA of a particular species. Therefore, DNA segments of the present invention will generally be MLL DNA segments which are isolated away from total human genomic DNA, although DNA segments isolated from other species, such as, e.g., Drosophila, may also be included in certain embodiments. Included within the term "DNA segment", are DNA segments which may be employed as probes, and those for use in the preparation of vectors, as well as the vectors themselves, including, for example, plasmids, cosmids, phage, viruses, and the like.

The techniques described in the following detailed examples re the generally preferred techniques for use in connection with certain preferred embodiments of the present invention. However, in that this invention concerns nucleic acid sequences and DNA segments, it will be apparent to those of skill in the art that this discovery may be used in a wide variety of molecular biological embodiments.

The DNA sequences disclosed herein will also find utility as probes or primers in modifications of the nucleic acid hybridization embodiments detailed in the following examples. As such, it is contemplated that oligonucleotide fragments corresponding to any of the cDNA or genomic sequences disclosed herein for stretches of between about 10 nucleotides to about 20 or to about 30 nucleotides will have utility, with even longer sequences, e.g., 40, 50 or 100 bases, 1 kb, 2 kb or 4 kb, 8.3 kb, 20 kb, 30 kb, 50 kb or even up to about 100 kb or more also having utility. The larger sized DNA segments in the order of about 20, 30, 50 or about 100 kb or even more, are contemplated to be useful in FISh embodiments.

The ability of such nucleic acid probes to specifically hybridize to MLL-encoding or other MLL genomic sequences will enable them to be of use in a variety of embodiments. For example, the probes can be used in a variety of assays for detecting the presence of complementary sequences in a given sample. However, other uses are envisioned, including the use of the sequence information for mapping the precise breakpoints in individual patients, and for the preparation of mutant species primers or primers for use in preparing other genetic constructions.

Nucleic acid molecules having stretches of 10, 20, 30, 50, 100, 200, 500 or 1000 or so nucleotides or even more, in accordance with or complementary to any of seq id no:1 through seq id no:6 will have utility as hybridization probes. These probes will be useful in a variety of hybridization embodiments, not only in Southern and Northern blotting in connection with analyzing patients' genes, but also in analyzing normal hematopoietic development and in charting the evolution of certain genes. The total size of fragment used, as well as the size of the complementary stretch(es), will ultimately depend on the intended use or application of the particular nucleic acid segment. Smaller fragments will generally find use in hybridization embodiments, wherein the length of the complementary region may be varied, such as between about 10 and about 100 nucleotides, up to 0.7 kb, 1.3 kb or 1.5 kb or even up to 8.3 kb or more, according to the complementary sequences one wishes to detect.

The use of a hybridization probe of about 10 nucleotides in length allows the formation of a duplex molecule that is both stable and selective. Molecules having complementary sequences over stretches greater than 10 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 20 nucleotides, or even longer where desired. Such fragments may be readily prepared by, for example, directly synthesizing the fragment by chemical means, by application of nucleic acid reproduction technology, such as the PCR technology of U.S. Pat. No. 4,603,102 (herein incorporated by reference) or by introducing selected sequences into recombinant vectors for recombinant production.

Accordingly, the nucleotide sequences of the invention may be used for their ability to selectively form duplex molecules with complementary stretches of MLL-like genes or cDNAs. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by 0.02M–0.15M NaCl at temperatures of 50° C. to 70° C. Such selective conditions tolerate little, if any, mismatch between the probe and the template or target strand, and would be particularly suitable for isolating MLL-like genes, for example, to gather information on the gene in different cell types or at different stages of the cell's cycle.

Of course, for some applications, for example, where one desires to prepare mutants employing a mutant primer strand hybridized to an underlying template or where one seeks to isolate MLL-encoding sequences from related species, functional equivalents, or the like, less stringent hybridization conditions will typically be needed in order to allow formation of the heteroduplex. In these circumstances, one may desire to employ conditions such as 0.15M–0.9M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results. Less stringent conditions would be suitable for identifying related genes, such as, for example, further drosophila or yeast genes, or genes from any organism known to be interesting from an evolutionary or developmentally stand point.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, colorimetric indicator substrates are known which can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by means of the label.

It is contemplated that longer DNA segments will find utility in the recombinant production of peptides or proteins. DNA segments which encode peptides of from about 15 to about 50 amino acids in length, or more preferably, from about 15 to about 30 amino acids in length are contemplated to be particularly useful in certain embodiments, e.g., in raising anti-peptide antibodies. DNA segments encoding larger polypeptides, domains, fusion proteins or the entire MLL protein will also be useful. DNA segments encoding peptides will generally have a minimum coding length in the order of about 45 to about 90 or 150 nucleotides, whereas DNA segments encoding larger MLL proteins, polypeptides, domains or fusion proteins may have coding segments encoding about 350, 430 or about 650 amino acids, and may be about 1.2 kb, 4.1 kb or even about 8.3 kb in length.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is contemplated that a nucleic acid fragment of almost any length may be employed, with the total length preferably being limited by the ease of preparation and use in the intended recombinant DNA protocol. For example, nucleic acid fragments may be prepared in accordance with the present invention which are up to 20,000 base pairs in length, as may segments of 10,000, 5,000 or about 3,000, or of about 1,000 base pairs in length or less.

It will be understood that this invention is not limited to the particular nucleic and amino acid sequences of seq id nos:1 through 6 and seq id nos:7 and 8, respectively. Therefore, DNA segments prepared in accordance with the present invention may also encode biologically functional equivalent proteins or peptides which have variant amino acids sequences. Such sequences may arise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged.

DNA segments encoding an MLL gene may be introduced into recombinant host cells and employed for expressing the encoded protein. Alternatively, through the application of genetic engineering techniques, subportions or derivatives of selected MLL genes may be employed. Equally, through the application of site-directed mutagenesis techniques, one may re-engineer DNA segments of the present invention to alter the coding sequence, e.g., to introduce improvements to the antigenicity of the protein or to test MLL protein mutants in order to examine the structure-function relationships at the molecular level. Where desired, one may also prepare fusion peptides, e.g., where the MLL coding regions are aligned within the same expression unit with other proteins or peptides having desired functions, such as for immuno-detection purposes (e.g., enzyme label coding regions), for stability purposes, for purification or purification and cleavage, or to impart any other desirable characteristic to an MLL-based fusion product.

MLL Protein Expression, Purification and Uses

In certain embodiments, DNA segments encoding MLL protein portions may be produced and employed to express the MLL proteins, domains or fusions thereof. Such DNA segments will generally encode proteins including MLL amino acid sequences of between about 100, 200, 250, 300 or about 650 amino acids, although longer sequences up to and including about 3800 or 3968 MLL amino acids are also contemplated. MLL protein regions which are both telomeric and centromeric to the breakpoint region may be produced, as exemplified herein by the generation of fusion proteins including MLL amino acids set forth in seq id no:8 and by amino acids 323–623 of seq id no:7. Other specific regions contemplated by the inventors to be particularly useful include, for example, the zinc finger regions represented by amino acids 574–1184, and more particularly, those including amino acids 574 to about 810 and about 1057 to 1184 of seq id no:7.

As a point of comparison with other nomenclature currently used in the art, the MLL amino acids of clone 14-7 (seq id no:8), telomeric to the breakpoint region, correspond to the HRX amino acids 2772–3209 in FIG. 4 of Tkachuk et al. (1992), and the MLL amino acids 323–623 of clone 14P-18B (seq id no:7), centromeric to the breakpoint region, correspond to the HRX amino acids 1101–1400 (Tkachuk et al., 1992). It should also be noted here that the cDNA clone 14P-18B (seq id no:4) differs from the published sequence of Tkachuk et al. (1992) in that clone 14P-18B lacks exon 8 sequences. This arose as a result of using a cDNA obtained subsequent to an alternative splicing reaction. Such alternative splicing is known to occur in other zinc finger proteins, such as the Wilms tumor protein. The zinc finger regions in the Tkachuk et al. sequence are represented generally by amino acids 1350–1700 and 1700–2000.

The expression and purification of MLL proteins is exemplified herein by the generation of MLL fusion proteins including glutathione S transferase, by their expression in *E. coli*, and by the use of glutathione-agarose affinity chromatography. However, it will be understood that there are many methods available for the recombinant expression of proteins and peptides, any or all of which will likely be suitable for use in accordance with the present invention. MLL proteins may be expressed in both eukaryotic and prokaryotic recombinant host cells, although it is believed that bacterial expression has advantages over eukaryotic expression in terms of ease of use and quantity of materials obtained thereby.

MLL proteins and peptides produced in accordance with the present invention may contain only MLL sequences themselves or may contain MLL sequences linked to other protein or peptide sequences. The MLL segments may be linked to other 'natural' sequences, such as those derived from other chromosomes, and also to 'engineered' protein or peptide sequences, such as glutathione-S-transferase (GST), ubiquitin, β-galactosidase, β-lactamase, antibody domains and, infact, virtually any protein or peptide sequence which one desires. The use of enzyme sensitive peptide sequences, such as , e.g., those found in the blood clotting cascade proteins, is also contemplated. One such application involves the use of a fusion protein domain for purification, e.g., using affinity chromatography, and then the subsequent cleavage of the fusion protein by a specific enzyme to release the MLL portion of the fusion protein.

As used herein, the term "engineered" or "recombinant" cell is intended to refer to a eukaryotic or prokaryotic cell into which a recombinant MLL DNA segment has been introduced. Therefore, engineered cells are distinguishable from naturally occurring cells which do not contain recombinantly introduced DNA, i.e., DNA introduced through the hand of man. Recombinantly introduced DNA segments will generally be in the form of cDNA (i.e., they will not contain introns), although the use of genomic MLL sequences is not excluded.

For protein expression, one would position the coding sequences adjacent to and under the control of a promoter. It is understood in the art that to bring a coding sequence under the control of a promoter, one positions the 5' end of the transcription initiation site of the transcriptional reading frame of the protein between about 1 and about 50 nucleotides "downstream" of (i.e., 3' of) the chosen promoter. Where eukaryotic expression is contemplated, one will also typically desire to incorporate into the transcriptional unit an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

The promoters used will generally be recombinant or heterologous promoters. As used herein, a recombinant or heterologous promoter is intended to refer to a promoter that is not normally associated with a the MLL gene in its natural environment. Such promoters may include virtually any promoter isolated from any bacterial or eukaryotic cell. Naturally, it will be important to employ a promoter that effectively directs the expression of the DNA segment in the cell type chosen for expression. The use of promoter and cell type combinations for protein expression is generally known to those of skill in the art of molecular biology, for example, see Sambrook et al. (1989). The promoters employed may be constitutive, or inducible, and can be used under the appropriate conditions to direct high level expression of the introduced DNA segment, such as is advantageous in the large-scale production of recombinant proteins or peptides.

Further aspects of the present invention concern the purification or substantial purification of MLL-based proteins. The term "purified" as used herein, is intended to refer to a composition which includes a protein incorporating an MLL amino acid sequence, wherein the protein is purified to any degree relative to its naturally-obtainable state. The "naturally-obtainable state" may be relative to the purity within a human cell or cell extract, e.g., for an MLL fusion protein produced in leukemic cells of a given patient, or may be relative to the purity within an engineered cell or cell extract, e.g., for a man-made MLL fusion protein.

Generally, "purified" will refer to an MLL protein or MLL peptide composition which has been subjected to fractionation to remove various non-MLL protein components such as other cell components. Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. A specific example presented herein is the purification of MLL:GST fusion proteins using glutathione-agarose affinity chromatography, followed by preparative SDS-polyacrylamide gel electrophoresis and electroelution.

The recombinant peptides or proteins produced from the DNA segments of the present invention will have uses in a variety of embodiments. For example, peptides, polypeptides and full-length proteins may be employed in the generation of antibodies directed against the MLL protein and antigenic sub-portions of the protein. Techniques for the production of polyclonal and monoclonal antibodies are described hereinbelow and are well known to those of skill in the art. The production of antibodies would be particularly useful as this would enable further detailed analyses of the location and function of the MLL protein, and MLL-related species, which clearly have an important role in mammalian cells and other cell types. The proteins may also be employed in various assays, such as DNA binding assays, and proteins and peptides may be employed to define the precise regions of the MLL protein which interact with targets, such as DNA, receptors, enzymes, substrates, and the like.

Recombinant Host Cells and Vectors

Prokaryotic hosts are generally preferred for expression of MLL proteins. Examples of useful prokaryotic hosts include *E. coli*, such as strain JM101 which is particularly useful, *Bacillus subtilis, Salmonella typhimurium, Serratia marcescens*, and various Pseudomonas species. In general, plasmid vectors containing replicon and control sequences which are derived from species compatible with the host cell should be used in connection with these hosts. Such vectors ordinarily carry a replication site and a compatible promoter as well as marking sequences which are capable of providing phenotypic selection in transformed cells, such as genes for ampicillin or tetracycline resistance. Those promoters most commonly used in recombinant DNA construction include the B-lactamase (penicillinase) and lactose promoter systems and the tryptophan (trp) promoter system.

In addition to prokaryotes, eukaryotic microbes, such as yeast cultures may also be used. *Saccharomyces cerevisiae* (common baker's yeast) is the most commonly used among eukaryotic microorganisms, although a number of other strains are commonly available. For expression in Saccharomyces, the plasmid YRp7, containing the trpl gene is commonly used. Suitable promoting sequences in yeast vectors include the promoters for 3-phosphoglycerate kinase or other glycolytic enzymes such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, an origin of replication, and termination sequences is suitable.

In addition to microorganisms, cultures of cells derived from multicellular (eukaryotic) organisms may also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years. Examples of such useful host cell lines are VERO and HeLa cells, Chinese hamster ovary (CHO) cell lines, and W138, BHK, COS-7, 293 and MDCK cell lines. Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication. Smaller or larger SV40 fragments may also be used, as may adenoviral vectors which are known to be particularly useful recombinant tools.

The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

Biological Functional Equivalents

As is known in the art, modification and changes may be made in protein structure and still obtain a molecule having like or otherwise desirable characteristics. For example, certain amino acids may be substituted for other amino acids in a protein structure without appreciable loss of interactive binding capacity with structures such as, for example, DNA, enzymes and substrate molecules. Since it is the interactive capacity and nature of a protein that defines that protein's biological functional activity, certain amino acid sequence substitutions can be made in a protein sequence (or, of course, its underlying DNA coding sequence) and nevertheless obtain a protein with like or even countervailing properties (e.g., antagonistic v. agonistic). The present invention thus encompasses MLL proteins and peptides including certain sequences changes.

In making conservative changes, the hydropathic index of amino acids may be considered. The importance of the hydropathic amino acid index in conferring interactive biologic function on a protein is generally understood in the art (Kyte & Doolittle, 1982) and it is known that certain amino acids may be substituted for other amino acids having a similar hydropathic index or score and still result in a protein with similar biological activity. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making changes, the substitution of amino acids whose hydropathic indices are within ±2 is preferred, those which are within ±1 are particularly preferred, and those within ±0.5 are even more particularly preferred.

Substitution of like amino acids can also be made on the basis of hydrophilicity, particularly where the biological functional equivalent protein or peptide thereby created is intended for use in immunological embodiments. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

While discussion has focused on functionally equivalent polypeptides arising from amino acid changes, it will be appreciated that these changes may be effected by alteration of the encoding DNA; taking into consideration also that the genetic code is degenerate and that two or more codons may code for the same amino acid.

Antibody Generation

As disclosed hereinbelow (see Example IV), now that the inventors have made possible the production of various MLL proteins, the generation of antibodies is a relatively straightforward matter. Antibody generation is generally known to those of skill in the art and many experimental animals are available for such purposes.

In addition to the polyclonal antisera described herein, the inventors also contemplate the production of specific monoclonal antibodies. Monoclonal antibodies (MAbs) specific for the MLL protein of the present invention may be prepared using conventional techniques. Initially, an MLL-containing composition would be used to immunize an experimental animal, such as a mouse, from which a population of spleen or lymph cells would be obtained. The spleen or lymph cells would then be fused with cell lines, such as human or mouse myeloma strains, to produce antibody-secreting hybridomas. These hybridomas may be isolated to obtain individual clones which can then be screened for production of antibody to the desired MLL protein.

For fusing spleen and myeloma or plasmacytoma cells to produce hybridomas secreting monoclonal antibodies against MLL, any of the standard fusion protocols may be employed, such as those described in, e.g., The Cold Spring Harbor Manual for Hybridoma Development, incorporated herein by reference. Hybridomas which produce monoclonal antibodies to the selected MLL antigen would then be identified using standard techniques, such as ELISA and western blot methods. Hybridoma clones can then be cultured in liquid media and the culture supernatants purified to provide MLL-specific monoclonal antibodies.

Epitopic Core Sequences

The present invention also makes possible the identification of epitopic core sequences from the MLL protein, as based on the deduced amino acid sequence encoded by the MLL gene. The identification of MLL epitopes directly from the primary sequence, and their epitopic equivalents, is a relatively straightforward matter known to those of skill in the art. In particular, it is contemplated that one would employ the methods of Hopp, as taught in U.S. Pat. No. 4,554,101, incorporated herein by reference, which teaches both the identification of epitopes from amino acid sequences on the basis of hydrophilicity, and the selection of biological functional equivalents of such sequences. The methods described in several other papers, and software programs based thereon, can also be used to identify epitopic core sequences, for example, the Jameson and Wolf computer programs and the Kyte analyses may also be employed (Jameson & Wolf, 1988; Wolf et al., 1988; Kyte & Doolittle, 1982).

The amino acid sequence of an "epitopic core sequence" thus identified may be readily incorporated into peptides, either through the application of peptide synthesis or recombinant technology. As mentioned above, preferred peptides for use in accordance with the present invention will generally be on the order of 15 to 50 amino acids in length, and more preferably about 15 to about 30 amino acids in length. It is proposed that shorter antigenic peptides which incorporate epitopes of the MLL protein will provide advantages in certain circumstances, for example, in the preparation of antibodies or in immunological detection assays. Exemplary advantages include the ease of preparation and purification, the relatively low cost and improved reproducibility of production, and advantageous biodistribution.

The MLL Gene

The present inventors recently identified a yeast artificial chromosome (YAC) that contains the breakpoint region in leukemias with the most common reciprocal translocations involving this chromosomal band, namely t(4;11), t(6;11), t(9;11), and t(11;19), (Rowley et al., 1990). They identified a gene termed MLL, for mixed lineage leukemia or myeloid/lymphoid leukemia, that spans the breakpoint on 11q23 (Ziemin-van Der Poel et al., 1991). This same gene is also referred to as ALL-1 (Cimino et al., 1991; Gu et al., 1992a;b), Htrx (Djabali et al., 1992) and HRX (Tkachuk et al., 1992) by other workers in the field, although MLL is the accepted designation for this gene adopted by the human genome nomenclature committee (Chromosome Co-ordinating Meeting, 1992).

Recent data indicate that the breakpoint in a cell line, RC-K8 with a t(11;14)(q23;q32), is approximately 110 kb telomeric to the breakpoint in other 11q23 translocations which involve the MLL gene (Akao et al., 1991b; Lu & Yunis, 1992; Radice & Tunnacliffe, 1992). The present inventors propose that there are at least two different regions of band q23 involved in chromosome 11q23 translocations; and distinguish these by using the term more centromeric to designate MLL rearrangements from those involving the more telomeric breakpoint—which has been described as the RCK locus (Akao et al., 1991b) or the p54 gene (Lu & Yunis, 1992).

Using pulse field gel electrophoresis analyses, the breakpoint region in MLL was mapped to a 92 kb NotI fragment approximately 100 kb telomeric to the CD3G gene. Non-repetitive sequences from three genomic clones isolated from this region detected transcripts in the estimated 11–12.5 kb size range (normal mRNA) in normal cells, and in the cell line, RS4;11 with a t(4;11), two highly expressed transcripts whose estimated size was 11.0 and 11.5 kb (rearranged mRNA) were detected (Ziemin-van Der Poel et al., 1991). It should be noted that the size of these transcripts has been estimated from measurements on Northern blots. In this size range, i.e., above about 10 kb, the resolution of agarose gels is known to be poorer, and hence size determinations made in this manner may be over- or under-estimates, and be found to vary about 2 or 3 kb or so, as has been reported by other groups for the MLL gene (Cimino et al., 1991; 1992).

Improved MLL Probes

Presented herein is evidence that the breakpoints in the t(4;11), t(6;11), t(9;11), and t(11;19) translocations are clustered within a 9 kb BamHI genomic region of the MLL gene, which has been more precisely defined, by sequencing, as being 8.3 kb in length. Using a 0.7 kb BamH1 cDNA fragment of the MLL gene called MLL 0.7B (seq id no:1), rearrangements on Southern analyses of DNA from cell lines and patient material with an 11q23 translocation were detected in this region. Probe MLL 0.7B (seq id no:1) is derived from a cDNA clone that lacks Exon 8 sequences, but this clearly has no adverse effects on breakpoint detection using this probe, which is still the most advantageous probe identified to date.

Northern blotting analyses of the MLL gene are also presented herein. These results demonstrate that the MLL gene has multiple transcripts, some of which appear to be lineage specific. In normal pre-B cells, four normal mRNA transcripts estimated to be of about 12.5, 12.0, 11.5 and 2.0 kb in size are detected. These transcripts are also present in monocytoid cell lines with additional hybridization to an estimated 5.0 kb normal mRNA transcript, indicating that expression of different sized MLL transcripts may be associated with normal hematopoietic lineage development.

In a cell line with a t(4;11), the expression of the large 12.5, 12.0 and 11.5 kb transcripts is reduced, and there is evidence of three other altered mRNA transcripts estimated to be of 11.5, 11.25 and 11.0 kb. In the Karpas 45 cell line (K45), with a t(X;11)(q13;q23) translocation, aberrant mRNA transcripts with estimated sizes of about 8 kb and about 6 kb, were detected. These translocations result in rearrangements of the MLL gene and may lead to altered function(s) of the MLL gene as well as that of other gene(s) involved in the translocation.

In further studies, unique sequences from the 0.7 kilobase BamHI fragment, corresponding to the centromeric and telomeric ends of the 8.3 kilobase germline fragment, were amplified by the polymerase chain reaction (PCR) and were used as probes to distinguish the chromosomal origin of rearranged bands on Southern blot analysis. Patient samples were selected on the basis of a karyotype containing an 11q23 abnormality and the availability of cryopreserved bone marrow or peripheral blood. 61 patients with acute leukemia and 11q23 aberrations, three cell lines derived from such patients, and 20 patients with non-Hodgkins lymphomas were analyzed.

It was found that the 0.7 kilobase cDNA fragment (seq id no:1) detected DNA rearrangements with a single BamHI digest in 58 leukemia patients and three cell lines with 11q23 abnormalities. This includes all cases (46 patients and two cell lines) with the common 11q23 translocations involving chromosomes 4, 6, 9, and 19. In addition, rearrangements were identified in 16 other cases with 11q23 anomalies, including translocations, insertions, and inversions. Rearrangements were not detected in three patients with leukemia and uncommon 11q23 translocations. Three of the 20 patients with lymphoma also had rearrangements. All of these breaks are first shown to occur within a 9 kilobase breakpoint cluster region, later identified as occurring within a region only 8.3 kb in length. Nineteen different chromosome breakpoints were associated with the MLL gene in these rearrangements, suggesting that MLL is juxtaposed to 19 different genes. In 70% of these cases, two rearranged bands, corresponding to the two derivative chromosomes, were detected and in 30%, only one rearranged band was present. In cases with only one rearranged band, it was always detected by only the centromeric probe. Thus, the sequences centromeric to the breakpoint are always preserved, whereas, telomeric sequences are deleted in 30% of cases.

It can be clearly seen that the 0.7 kilobase cDNA probe of the present invention detects rearrangements on Southern blot analysis with a single BamHI restriction digest in all patients with the common 11q23 translocations. The same breakpoint occurs in at least 14 other 11q23 anomalies. The breaks were all found to occur in a 9 kilobase breakpoint cluster region within the MLL gene later shown, by sequencing, to be an 8.3 kb region. The present inventors have, therefore, developed specific probes that can distinguish between the two derivative chromosomes. In cases with only one rearranged band, the exon sequences immediately distal to the breakpoint are deleted. This cDNA probe will be very useful clinically both in diagnosis of rearrangements of the MLL gene as well as in monitoring patients during the course of their disease.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE I

Cloning of cDNAs of the MLL Gene that Detect DNA Rearrangements and Altered RNA Transcripts in Human Leukemic Cells with 11q23 Translocations 1. Materials and Methods CELL LINES AND PATIENT MATERIAL. The characterization of the cell lines RS41;11, RCH-ADD (an EBV transformed cell line with a normal karyotype from a patient with leukemia and a t(1;19)), SUP-T13, U937 and RC-K8 have been described (Stong & Kersey, 1985; Jack et al., 1986; Smith et al., 1989; Kubonoshi et al., 1986; Sundstrom & Nilsson, 1976). The clinical and cytogenetic characteristics of the patient material and cell lines with 11q23 translocations are listed in Table 1.

TABLE 1

CLINICAL DIAGNOSIS AND KARYOTYPES OF CELL LINES AND PATIENTS

| Patient or Cell Line | Diagnosis | Karyotype |
| --- | --- | --- |
| RS4; 11 | B-Cell with Monocytoid Features | 46, XX, t (4; 11) (q21; q23), i (7q) |
| RC-K8 | Histiocytic Lymphoma | 46, X, t (Y; 7) (q21; q23), t (2; 2) (p25; q23), t (3; 4) (q29; q31), der (8) t (8, 8) (q22; q11), t (10; 15) (p11; p13), t (11; 14) (q23; q32), t (13; 20) (q12; q13), −14, +mar |
| SUP-T13 | T-LL | 46, XX, t (1; 8) (q32; q24), t (1; 5) (q41; p11) del (9) (q24 q34), t (11; 19) (q23; q13) |
| Patient 1 | ALL | 46, XY, t (4; 11) (q21; q23) (4%)/46, XY, t (2; 9) (p12; p23), t (4; 11) (q21; q23) (83%)/46, XY (13%) |
| Patient 2 | AML | 46, XY, t (9; 11) (q21; q23) (95%)/46, XY (5%) |
| Patient 3 | AML | 46, XX, t (11; 19) (q23; p13) (83%)/46, XX (17%) |

Figure 1:
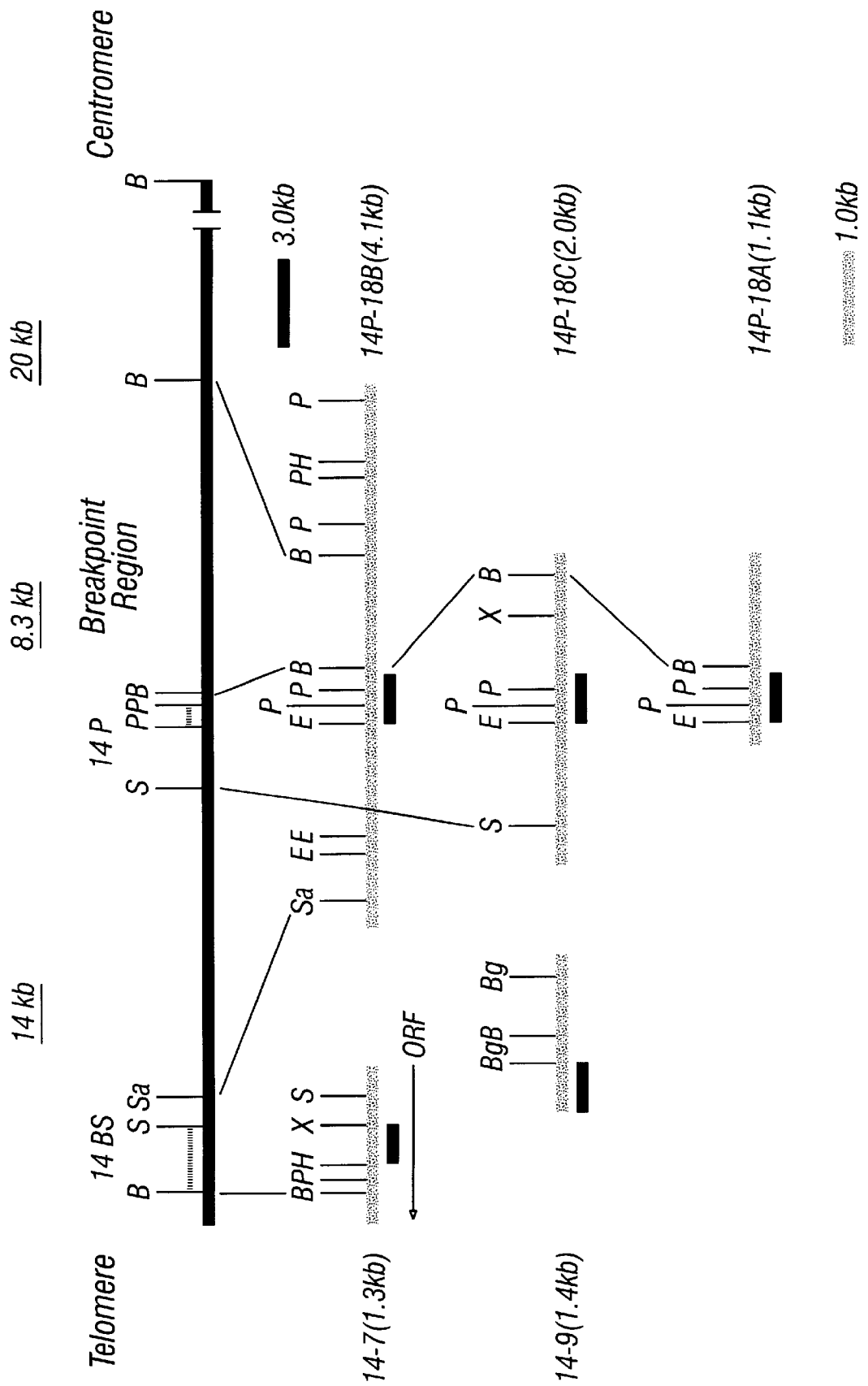
FIG. 1.

ALL = acute lymphoblastic leukemia
AML = acute myeloblastic leukemia
T-LL = T-cell lymphoblastic lymphoma PREPARATION AND SCREENING OF A cDNA LIBRARY. Poly(A)$^+$ RNA was isolated from a monocytic cell line (U937) using the Fast Track Isolation mRNA Kit (Invitrogen), and a custom random primed and oligo-d(T) primed cDNA library was made by Stratagene. A cDNA library with a titre of $1.4 \times 10^6$ pfu/ml cloned into the EcoRI site of Lambda Zap II was obtained. One half million plaques were plated and hybridized separately with two $^{32}$P labelled probes, a 2.1 kb BamHI/SstI fragment from the telomeric end of genomic clone 14 (Ziemin-van Der Poel et al., 1991) referred to as 14BS and a 0.8 kb PstI fragment from the centromeric end, 14P (FIG. 1). Labeling and hybridization protocols were as previously described (Shima et al., 1986). Positive clones were purified and subcloned into the Bluescript vector using the in vivo plasmid excision protocol (Stratagene). Clones were characterized by Southern blot hybridization and were subsequently mapped and sequenced using the Sequenase Kit (United States Biochemical).

NORTHERN AND SOUTHERN ANALYSES. DNA was extracted from both cell lines and from patient material. Ten micrograms of each sample was digested with restriction enzymes, separated on agarose gels and transferred to nylon membranes. Poly (A)+ RNA was extracted from $100 \times 10^6$ cells in logarithmic or stationary growth phase using the Fast Track Isolation Kit (Invitrogen). Five micrograms of formamide/formaldehyde denatured RNA was electrophoresed on a 0.8% agarose gel at 40 volts/cm for 16 or 20 hours and transferred to nylon membranes. Hybridization and labeling protocols were as described previously (Shima et al., 1986).

2. Results cDNA Clones

Using a non-repetitive sequence called 14BS (2.1 kb) (FIG. 1) from the telomeric end of genomic clone 14 (Ziemin-van Der Poel et al., 1991), the present inventors detected two cDNA clones 14-7 (1.3 kb) and 14-9 (1.4 kb). Mapping and sequencing of these two clones, revealed approximately 0.5 kb of homology, and clone 14-9 contained a long stretch of Alu repeats. Clone 14-7 had an open reading frame (ORF), that extended for the entire insert length with a predicted direction of transcription of MLL from centromere to telomere. Using a unique centromeric fragment, 14P (0.8 kb), of clone 14, three additional cDNA clones were obtained; namely 14P-18A (1.1 kb), 14P-18B (4.1 kb) and 14P-18C (2.0 kb). The relationship of all these clones is clearly set forth in FIG. 1. The organization of the genomic segment is shown in FIG. 9 and the entire 8.3 kb genomic region is represented by seq id no:6. cDNA clone 14P-18B (seq id no:4) differs from the published sequence of Tkachuk et al. (1992) in that clone 14P-18B lacks exon 8 sequences.

Sequence analyses indicated that the cDNA clone 14P-18A is completely contained in 14P-18B, while the region of homology of 14P-18B with 14P-18C is only 0.2 kb. As is the case with clone 14-9, 14P-18C also contains stretches of Alu repeats. All of the cDNA clones were hybridized to Southern blots with genomic DNA digested with a range of restriction enzymes and FIG. 1 shows the alignment of the BamH1 sites in the cDNA clones to approximately 50 kb of genomic sequence. The genomic BamH1 sites are the same as those reported by Cimino et al (1992) for this same gene which they term ALL-1. The Sal1 and Sst1 sites in the cDNA clones and the genomic sequence were related by hybridization to Southern blots of the BamHI1 14 kb genomic fragment. Aligning clone 14-7 with clone 14P-18B indicates that this is an almost continuous cDNA sequence of 5.4 kb of the MLL gene.

Southern Analyses

Figure 2:
Figure 2:
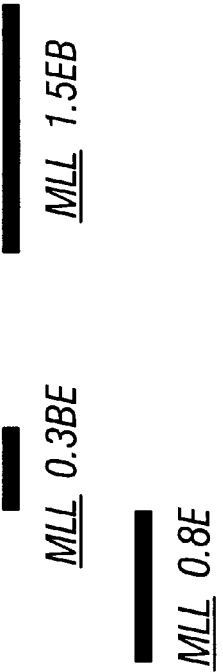
Figure 2:
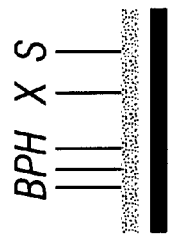
Figure 3:
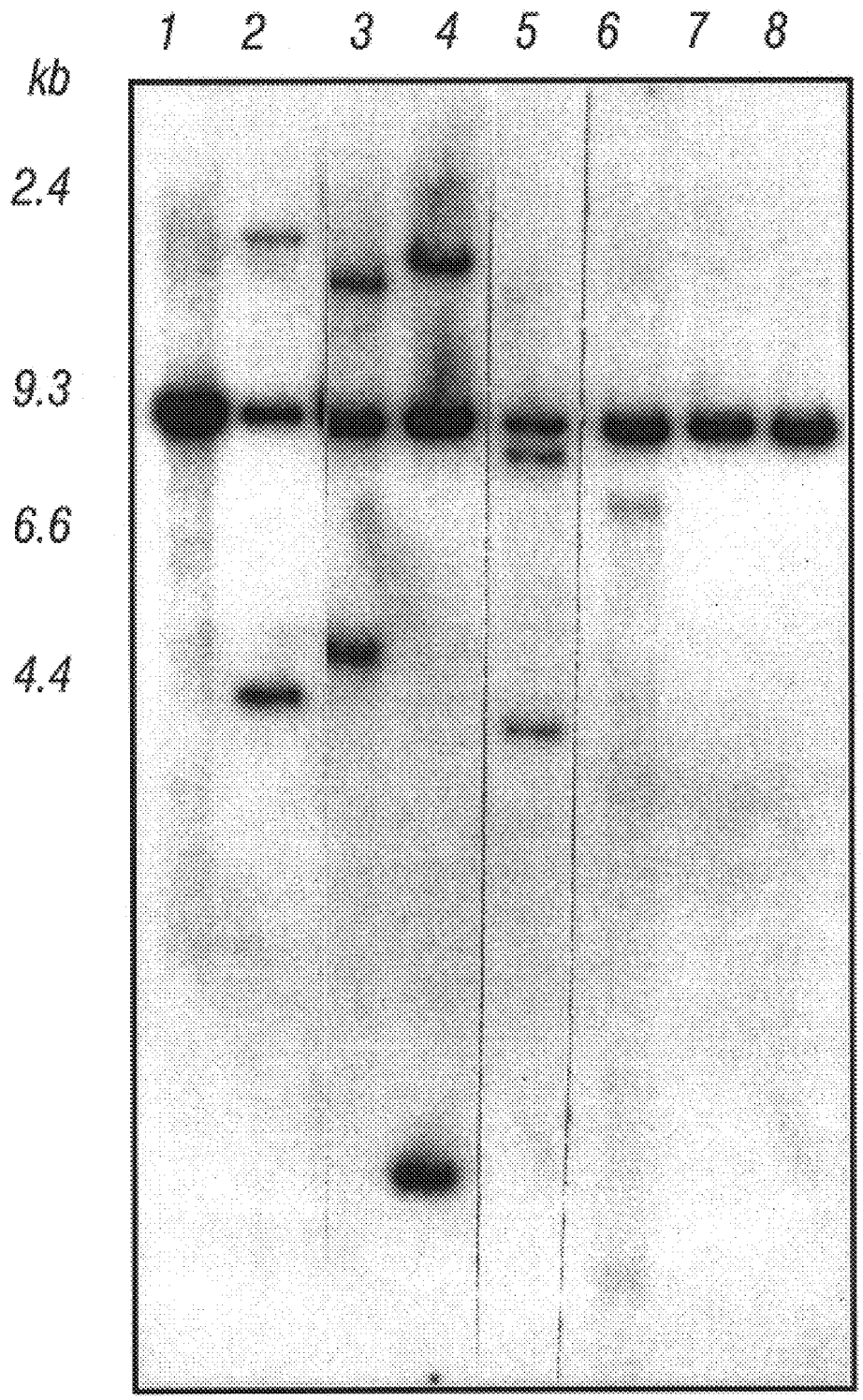

Southern blots of DNA from control samples, cell lines and patient material with 11q23 translocations were hybridized to an internal 0.7 kb BamHI fragment of 14P-18B termed MLL 0.7B, and subsequently referred to as 0.7B (FIG. 2). This probe detects a 9 kb BamHI germ line band, and also detects DNA rearrangements in samples with a t(4;11), t(6;11), t(9;11), and t(11;19) tested to date (FIG. 3 and Example II). In most of the samples tested, this probe detected two rearranged bands indicating hybridization to both derivative chromosomes. In the cell line SUP-T13 which has a t(11;19) this 0.7B probe hybridized very weakly to at least two rearranged bands suggesting a deletion which includes DNA sequences homologous to the probe (FIG. 3, lane 6). In the RC-K8 cell line with a t(11;14) (FIG. 3, lane 8), no rearrangement was detected.

Northern Analyses

To determine the nature of the transcripts detected by the cloned cDNAs, sequential hybridizations to the same Northern blots were performed. The cDNA clones used were 14-7, and three adjacent fragments of the cDNA clone 14P-18B, namely a 0.3 kb BamH1/EcoR1 fragment termed MLL 0.3BE (0.3BE), a 0.7 kb BamH1 fragment (MLL 0.7B, or 0.7B), and a 1.5 kb EcoR1/BamH1 fragment termed MLL 1.5EB or 1.5EB (FIG. 2). These fragments are cDNAs that are telomeric, span and are centromeric to the breakpoint junction, respectively. It should be noted that the EcoR1 site used to excise the 1.5 kb fragment was a cloning site.

The most telomeric cDNA clone 14-7, detected two large transcripts of 12.0 and 11.5 kb in normal cell lines (EBV immortalized B cells) and in the cell line RC-K8 (FIG. 4A panel a). However, in the RS4;11 cell line three transcripts of estimated sizes 12.0, 11.5 and 11.0 kb were evident (FIG. 4B panel a). There was only weak hybridization to the normal 12.0 and 11.0 kb message in the latter sample, while the 11.5 kb transcript was expressed in high abundance (FIG. 4a where actin is used as a control probe). The ratio of expression of the 11.5 and 11.0 kb transcripts in the RS4;11 cell line was dependent upon the state of cell growth when RNA was extracted, (compare FIGS. 4A panel a, and 4B panel a).

On separate hybridizations with all three of these fragments (0.3BE, 0.7B and 1.5EB) of clone 14P-18B, the estimated 12.0 and 11.5 kb transcripts were detected in normal cell lines (FIG. 4A, panel a–c). The 0.3BE probe also detected a normal 2.0 kb transcript which was expressed in all cell lines tested so far. In monocytoid cell lines the 0.3BE probe detected an additional transcript of 5.0 kb. In addition to hybridization to the estimated 12.0 and 11.5 kb transcripts in normal cell lines, the most centromeric 1.5EB probe detected the large 12.5 kb transcript, which the present inventors have described as a MLL transcript that spans the breakpoint (Ziemin-van Der Poel et al., 1991).

It is important to stress that the size determination of larger sized nucleic acids using Northern blotting is not always completely accurate. In the size range of about 9–10 kb, and above, it is known that the poorer resolution of agarose gels can lead to the over- or under-estimation of transcript size. Such determinations may even differ by up to about 2 kb or so. Therefore, it will be understood that all references to size determinations in the results and discussions which follow are the currently best available estimate of the transcript size, and may not precisely correlate with the size determined by other means, such as, for example, by direct sequencing.

Figure 5:
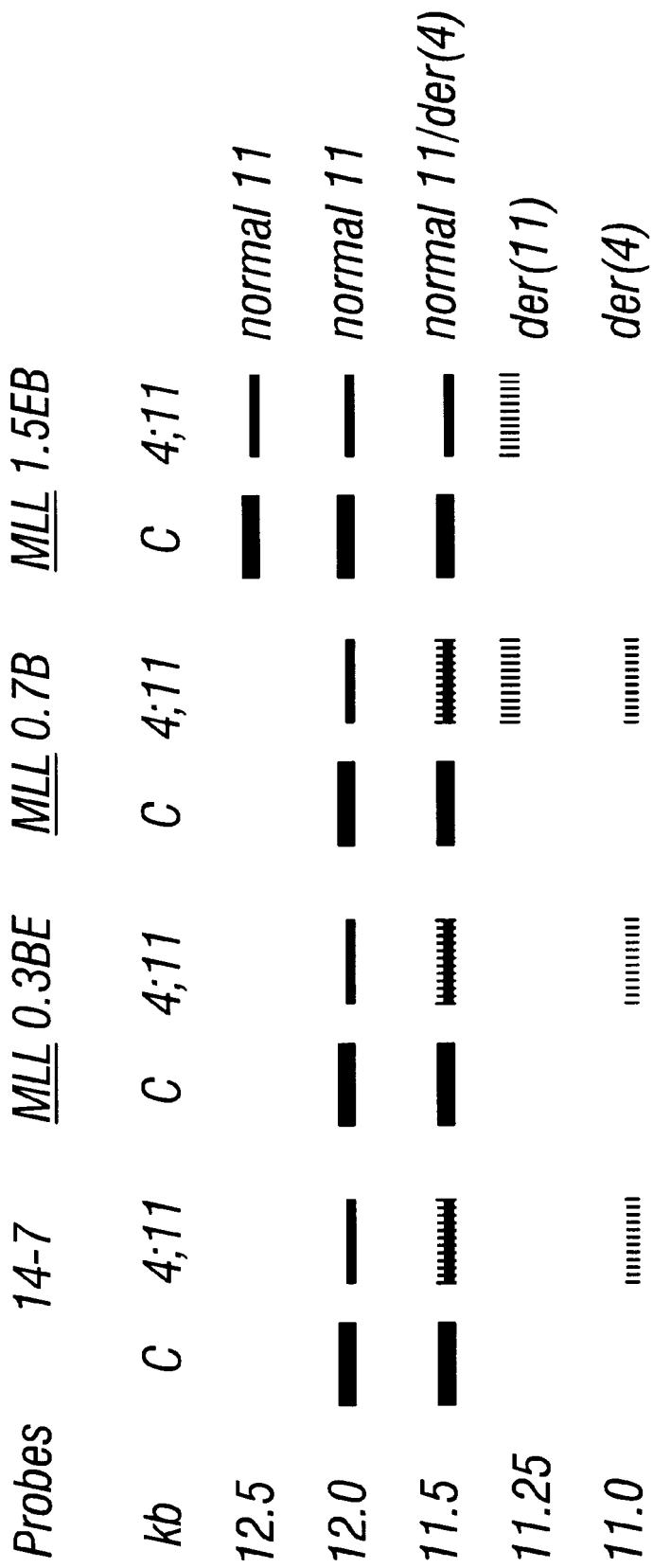

In the RS4;11 cell line, there was evidence of differential hybridization of these probes to transcripts. FIG. 4B shows a Northern blot with RNA from the RS4;11 cell line electrophoresed for 20 hours to obtain better resolution of the large size transcripts. The 0.3BE probe hybridized very strongly to the over-expressed rearranged 11.5 kb and the 11.0 kb transcripts with weak hybridization to a transcript of 12.0 kb. There was also hybridization to the two smaller normal transcripts of 5.0 and a 2.0 kb (FIG. 4B panel b). The adjacent 0.7B probe which detected DNA rearrangements in cells with 11q23 translocations, hybridized to the over-expressed 11.5 kb and 11.0 kb rearranged transcripts with weak hybridization to the normal 12.0 kb transcript as above. However, this 0.7B probe also detected a rearranged mRNA transcript estimated to be 11.25 kb (FIG. 4B panel c) in these cells with a t(4;11). Finally, the 1.5EB probe which is centromeric to the breakpoint junction also detected this rearranged 11.25 kb transcript with weak hybridization to the normal 12.5, 12.0 and 11.5 kb transcripts (FIG. 4B panel d). Of notable exception, this 1.5EB probe did not detect the over-expressed 11.5 kb transcript and the 11.0 kb transcript in the RS4;11 cell line. The detection of different mRNA transcripts by these probes is summarized in Table 2, and also represented graphically in FIG. 5.

MLL gene. Two other cDNAs, 14P-18C and 14-9, contain Alu repetitive sequences and share limited homology with 14P-18B and 14-7 respectively (FIG. 1). This indicates that these cDNAs are derived either from different transcripts or are derived from incompletely processed transcripts. It is now known that virtually all 12.5 to 15.0 kb of the MLL gene is an open reading frame and that there is homology between MLL and the zinc finger region of the *Drosophila trithorax* gene (Tkachuk et al., 11992; Gu et al., 1992a).

Use of fragments of the cDNA clones in Northern hybridizations provided evidence of a range of MLL transcript sizes in different hematopoietic lineages as well as of alternative exon splicing of the MLL gene transcripts. The normal transcripts, estimated to be 2.0, 11.5, 12.0 and 12.5 kb in length, are expressed in both hematopoietic and

TABLE 2

SIZE OF mRNA TRANSCRIPTS DETECTED BY PROBES IN NORMAL AND LEUKEMIC CELLS

| Probes | Normal Cells | | | | | Leukemic (RS4; 11) Cells | | | | |
|--------|------|------|-----|-----|---------|---------|-------|-------|------|-----|
| 14.7   | 12.0 | 11.5 |     |     | 12.0 (w)| 11.5*   | 11.0  |       |      |     |
| 0.3BE  | 12.0 | 11.5 | 5.0 | 2.0 | 12.5 (w)| 12.0 (w)| 11.5* | 11.0  | 5.0  | 2.0 |
| 0.7B   | 12.0 | 11.5 |     |     | 12.5 (w)| 12.0 (w)| 11.5* | 11.25 | 11.0 |     |
| 1.5EB  | 12.5 | 12.0 | 11.5|     | 12.5 (w)| 12.0 (w)| 11.5  | 11.25 |      |     |

(w) in the leukemic cells indicates the presence of a weaker signal than was detected in the normal (or control) cells.
14.7, seq id no: 5; 0.3BE, seq id no: 2; 0.7B, seq id no: 1; and 1.5EB, seq id no: 3.
*Indicates the detection of a weak signal from the normal 11.5 kb transcript in addition to the detection of a strong signal from an aberrant 11.5 kb transcript in the leukemic cells (note that probe 1.5EB does not detect an aberrant 11.5 kb transcript in leukemic RS4; 11 cells, but still indicates a lower level of the normal 11.5 kb transcript). Note that the situation in RS4; 11 cells is more complex than may be expected in most leukemic cells, due to the equivalent sizes of normal and aberranttranscripts (contrast, e.g., with Karpas 45 cells), but that a clear differentiation can still be made using these probes.

3. Discussion

The inventors have isolated several cDNA clones of the MLL gene of which the internal 0.7 kb BamH1 fragment of cDNA clone 14P-18B (0.7B) detected rearrangements in leukemic samples with the centromeric 11q23 translocation (FIG. 3 and Example II). The data presented herein indicate that the breakpoints in band 11q23 in the common translocations which involve chromosomes 4, 6, 9 and 19 are clustered within an 8.3 kb region of the MLL gene. In many of the samples, this probe detected two rearranged bands indicating hybridization to both derivative chromosomes. This implies that this 0.7B fragment contains DNA sequences from both ends of the 9 kb BamHI genomic fragment, see also Example II.

DNA rearrangements were not detected in the RC-K8 cell line which has a t(11;14)(q23;q32), which further confirms the existence of at least two distinct breakpoint regions in 11q23 (Rowley et al., 1990; Akao et al., 1991b; Lu & Yunis, 1992; Radice & Tunnacliffe, 1992). One is the more centromeric region and involves the MLL gene; whereas the other is at least 110 kb telomeric and includes the breakpoint seen in the RC-K8 cell line (Akao et al., 1991b; Lu & Yunis, 1992; Radice & Tunnacliffe, 1992). Furthermore Lu and Yunis have determined that the 5' non coding region of the p54 gene is split in this more telomeric 11q23 translocation, which indicates that the p54 gene is different from MLL.

FIG. 1 shows the alignment of the cDNAs to genomic sequences which span approximately 50 kb. The largest cDNA, 14P-18B is 4.1 kb, and it is located centromeric to clone 14-7 to give 5.4 kb of almost continuous cDNA sequence. The inventors have therefore cloned more than one third of the 11.0, 11.5, 12.0 and 12.5 kb transcripts of the non-hematopoietic tissues. The 5.0 kb transcript is detected in monocytic cell lines and in the T-cell line tested. The level of expression of the 5.0 kb transcript in the RS(4;11) cell line is approximately 50% of that expressed in the monocytic cell lines. This result may reflect the biphenotypic nature of this cell line which has both pre-B-cell and monocytoid features.

Northern blot analyses using the 14-7 probe (which is telomeric to the breakpoint region) detected the two large transcripts of 12.0 and 11.5 kb in control B cells and in the RC-K8 cell line. In the RS4;11 cell line, this probe detected a weak signal at 12.0 kb with strong hybridization to an 11.5 kb transcript. This probe also detected an additional smaller transcript of 11.0 kb in the RS41;11 cell line (FIG. 4B panel a). The 12.0 and 11.0 kb transcripts appear to be in low abundance while the 11.5 kb transcript is over-expressed. The relative ratio of hybridization of the estimated 11.5 and 11.0 kb rearranged mRNA transcripts varies with the growth phase of the RS4;11 cells prior to RNA extraction. In logarithmic growth phase, the ratio of the two signals is approximately 3:1, whereas in stationary phase, the 11.0 kb transcript is hardly discernible (FIGS. 4A and 4B, panel a).

To define more precisely the nature of the transcripts detected in control cell lines and in the cell line with the t(4;11), three adjacent fragments of clone 14P-18B (FIG. 2) were hybridized sequentially to the same Northern blots (FIG. 4A,4B). All of the probes detected the 12.0 and 11.5 kb transcripts in normal cells. The most centromeric 1.5EB probe also detected a 12.5 kb transcript on very long exposure of autoradiograms. These three transcripts are normal MLL transcripts which cross the 11q23 breakpoint region. The fact that the 1.5EB probe is the only fragment of the 4.1 kb 14P-18B cDNA clone that detects the large 12.5 kb transcript indicates the existence of alternative exon splicing. To date, the only other cDNA clones which detect this transcript are 14-9 and 14P-18C. These cDNA clones contain Alu repeats, which might indicate the presence of intron sequences in incompletely processed MLL transcripts.

On sequential hybridization of these three fragments to Northern blots of RNA from the RS4;11 cell line there was evidence of weak hybridization to the normal 12.5, 12.0 and 11.5 kb transcripts, all of which cross the breakpoint (FIGS. 4A, 4B). The present inventors now have evidence that the over-expressed 11.5 kb transcript in the RS4;11 cell line is not the same as the normal 11.5 kb transcript. The 1.5EB probe detects the normal 11.5 kb transcript in control cells, however there is only a weak hybridization signal to an 11.5 kb transcript in the RS4;11 cell line (FIG. 4A, panel c). This weak hybridization is proposed to be detection of the normal 11.5 kb transcript, and is a different transcript from the over-expressed 11.5 kb transcript which is detected with all the other more telomeric probes. These data indicate that the weakly hybridizing 11.5 kb transcript detected by the 1.5EB probe, is one of the three normal 12.5, 12.0 and 11.5 kb MLL transcripts that cross the breakpoint. The reduced expression of all these three transcripts in the RS4;11 cell line may be due to transcription from only the normal chromosome 11. Therefore, the over-expressed 11.5 kb transcript which was detected with the more telomeric probes is an altered MLL transcript derived from the der(4) chromosome (FIG. 4B panel a–c).

There was evidence of two other altered MLL transcripts of 11.25 and 11.0 kb in the RS4;11 cell line. The origin of these two transcripts was easier to define as there was no hybridization to transcripts of these sizes in RNA from normal cells. The 11.25 kb transcript was detected with the centromeric 1.5EB probe and the 0.7B probe that contains sequences that span the breakpoint, and thus suggests that it originates in the der(11) chromosome (FIG. 4B panel c,d). The 11.0 kb transcript was detected with the same three probes (14-7, 0.3BE and 0.7B) as the aberrant 11.5 kb transcript and is probably derived from the der(4) chromosome (FIG. 4B panel a–c) according to the scheme in FIG. 5. Thus the inventors have developed cDNA probes for the MLL gene which permit detection of three altered transcripts of MLL arising from both derivative chromosomes in a cell line with a t(41;11).

In recent reports by Croce and colleagues (Cimino et al. 1991; 1992; Gu et al. 1992a) a genomic clone which was 10 kb centromeric to the breakpoint region, detected a major transcript said to be about 12.5 kb and a minor 11.5 kb transcript with additional hybridization to an 11.0 kb species which was only found in cell lines with a t(4;11). This 11.0 kb transcript may be the same as the altered 11.25 kb MLL transcript detected in the RS4;11 cell line using the 0.7B and 1.5EB cDNA probes. The inventors propose that this transcript is from the der(11) chromosome. The discrepancy in size between the transcript detected in this study and that of Cimino et al may be due to poor resolution of transcripts of this large size. Using the centromeric genomic probe, Cimino et al. (1992) also reported hybridization to 0.4 and 5.0 kb transcripts in a variety of cell lines which were not found in the present study.

In summary the cDNA and Northern analyses indicate that the MLL gene is a large complex gene with numerous transcript sizes. In analyses of the transcripts in the RS4;11 cell line, the inventors found that there is reduced expression of the normal MLL transcripts of 12.5, 12.0 and 11.5 kb, and that (Heim & Mitelman, 1987) the over-expressed 11.5 kb transcript and the 11.0 kb transcript as well as the 11.25 kb transcript specific to the RS4;11 cell line are altered MLL transcripts arising from the translocation derivative 4 and derivative 11 chromosomes respectively. How, or if, these three altered transcripts of the MLL gene alter normal MLL protein expression and function and contribute to leukemogenesis is still unknown.

A major question in reciprocal translocations is which derivative chromosome contains the critical junction. Analysis of complex translocations indicate that, for these 11q23 translocations, it is the der(11) chromosome. The Southern blot analysis of patient data, as presented in Example II, supports this interpretation. Because the direction of transcription of MLL is from centromere to telomere, the juxtaposition of the 5' sequences and the 5' flanking regulatory regions of MLL remaining on the der(11) to various other genes on other chromosomes may play an important role in all of these leukemias. The fact that this translocation is associated with lymphoid and myeloid leukemias suggests that the regulated expression of the MLL gene may be important in normal hematopoietic lineage specificity, and that rearrangements of this gene play a critical role in the oncogenic process of these leukemias.

EXAMPLE II

A cDNA Probe Detects All Rearrangements of the MLL Gene in Leukemias with Common and Rare 11q23 Translocations This example concerns the identification of a restriction fragment from a cDNA clone which detects rearrangements in all cases of the t(4;11), t(6;11), t(9;11), and both types of t(11;19) examined as well as in many rare translocations with a breakpoint at band 11q23. A key feature of this fragment is that it contains exons that flank the breakpoints in all of these cases. The present inventors have thus delineated an 8.3 kilobase breakpoint cluster region in the common and rare translocations involving 11q23. In addition, through the use of probes amplified by the polymerase chain reaction (PCR) from the centromeric and telomeric portions of this cDNA fragment, the present invention provides methods and compositions for the use in distinguishing between the two derivative chromosomes. Moreover, this example provides further data to support the hypothesis that the derivative 11 chromosome contains the critical translocation junction.

1. Materials and Methods

PATIENTS AND CELLS LINES. Patient samples were obtained from the University of Chicago Medical Center, Saitama Cancer Center, Southwest Biomedical Research Institute, and Memorial Sloan-Kettering Cancer Center. The samples were selected on the basis of a karyotype containing an 11q23 abnormality and the availability of cryopreserved leukemic bone marrow or peripheral blood. The cell line RS4;11 was a gift from J. Kersey at the University of Minnesota; (Stong & Kersey, 1985) SUP-T13 was a gift from S. Smith at the University of Chicago, (Smith et al., 1989) and Karpas 45 was a gift from A. Karpas at Cambridge University (Karpas et al., 1977).

CYTOGENETIC ANALYSIS. Cytogenetic analysis was performed using a trypsin-Giemsa banding technique. Chromosomal abnormalities were described according to the International System for Human Cytogenetic Nomenclature (Harnden & Klinger, 1985).

cDNA LIBRARY. A cDNA library was prepared from a monocytic cell line as described above in Example I. The library was screened with probes from the centromeric and telomeric ends of a 14 kilobase genomic BamHI fragment (clone 14) and several cDNA clones were obtained and mapped with restriction endonucleases. A 0.7 kilobase fragment called MLL 0.7B was isolated from a cDNA clone named 14P18C and used as described below.

MOLECULAR ANALYSIS. DNA was extracted from cryopreserved cells and digested with restriction enzymes, electrophoresed on 0.7% agarose gels, transferred to nylon membranes, and hybridized with radiolabeled cDNA probes at 42° C. All DNA blots were washed to a final stringency of 1×SSC and 1% SDS at 65° C. prior to autoradiography.

SEQUENCE ANALYSIS. Nucleotide sequences were obtained by the dideoxy chain termination method with a double stranded DNA sequencing strategy using the Sequenase kit (United States Biochemical, Cleveland, Ohio).

POLYMERASE CHAIN REACTION (PCR). Amplification of unique sequences from the 0.7 kilobase BamHI fragment, corresponding to exons at the centromeric and telomeric ends of the 9 kilobase germline fragment, was performed using standard methods. 10 ng of cDNA were amplified in 50 µl of reaction mix containing 1.5 mM MgCl$_2$, 1.25 mM dNTPs, and 2.5 U of Taq polymerase. Reactions were performed in an automated thermal cycler (Perkin-Elmer/Cetus, Norwalk, Conn.) with denaturation at 92° C. for 50 seconds, annealing at 50° C. for 50 seconds, and extension at 72° C. for one minute.

2. Results

Figure 6:
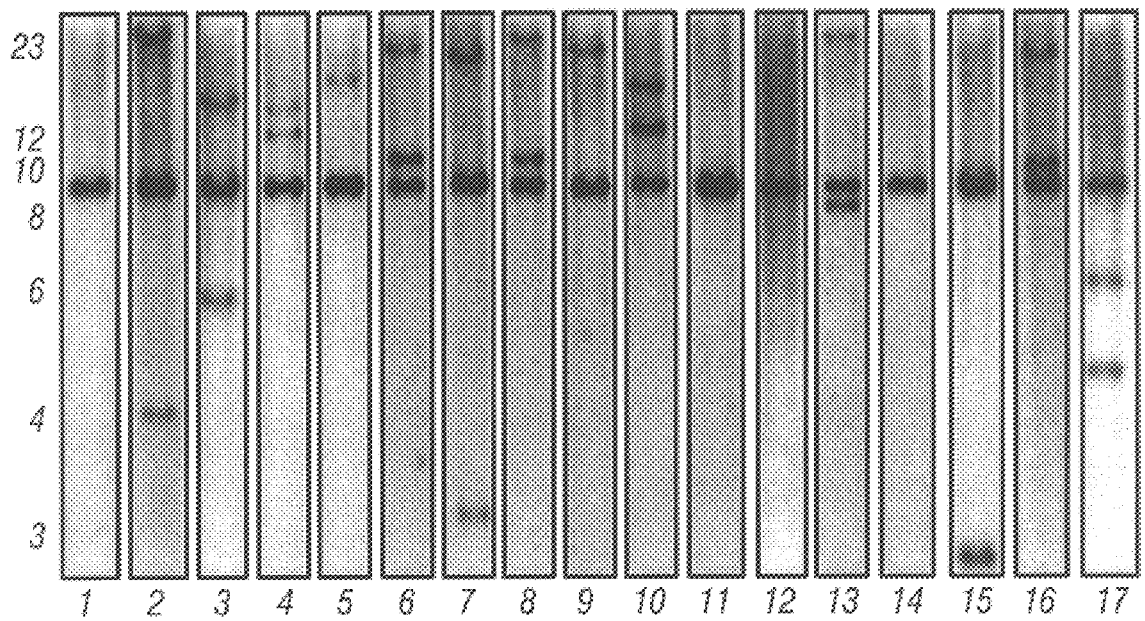

The inventors isolated a 0.7 kilobase BamHI cDNA fragment which is composed of exons flanking the centromeric and telomeric ends of an 8.3 kilobase genomic BamHI fragment of the MLL gene (Example I, FIGS. 1 and 2). On Southern blot analysis, this 0.7 kilobase cDNA fragment, 0.7B, detected rearrangements of the MLL gene in 61 patients (58 with leukemia and three with lymphoma) and three cell lines (FIG. 6). This included all 48 cases (46 patients and two cell lines) with the common translocations involving 11q23 including the t(41;11)(q21;q23), t(61;11)(q27;q23), t(91;11)(p22;q23), t(11;19)(q23;p13.1) and t(11;19)(q23;p13.3) (Table 3).

TABLE 4

DNA REARRANGEMENTS IN UNCOMMON 11q23 TRANSLOCATIONS DETECTED WITH THE 0.7 KILOBASE cDNA PROBE

| DIAGNOSIS | PARTIAL KARYOTYPE | NUMBER OF REARRANGED BANDS |
|---|---|---|
| AML-M4 | t (1; 11) (p32; q23) | 2 |
| ALL | t (1; 11) (p21; q23) | 1 |
| ALL | t (2; 11) (p21; q23) | 1 |
| Follicular, small-cleaved lymphoma | t (14; 18) (q32; q21) and t (6; 11) (p12; q23) | 1 |
| AML-M4 | t (10; 11) (p11; q23) | 2 |
| AML-M5 | t (10; 11) (q22; q23) | 2 |
| AML-M5 | insertion (10; 11) (p11; q23 q24) | 2 |
| AML-M5 | insertion (10; 11) (p11; q23 q13) | 2 |
| AML-M5 | insertion (10; 11) (p13; q23 q24) | 1 |
| AML-M1 | t (11; 15) (q23; q15) | 1 |
| AML-M5 | t (11; 17) (q23; q21) | 1 |
| AML-M2 | t (11; 17) (q23; q25) | 2 |
| Diffuse mixed-cell lymphoma | t (11; 18) (q23; q21) | 1 |
| AML-M5 | t (11; 22) (q23; q12) | 2 |
| Karpas 45 cell line | t (X; 11) (q23; q13) | 2 |
| Burkitt's lymphoma | t (8; 14) (q24; q32) and inversion (11) (q14 q23) | 1 |

Also identified by the 0.7B probe were similar MLL gene rearrangements in DNA from 8 patients and one cell line with several less common 11q23 translocations listed in Human Genome Mapping 11 (Table 3) (Mitelman et al., 1991). These include translocations involving 1p32, 1q21, 2p21, 17q21, 17q25, Xq13, and three cases with insertion 10;11. In addition, 7 other 11q23 anomalies which have not

TABLE 3

DNA REARRANGEMENTS IN LEUKEMIAS WITH COMMON 11q23 TRANSLOCATIONS DETECTED WITH THE 0.7 KILOBASE cDNA PROBE*

|  | t (4; 11) (q21; p23) | t (6; 11) (q27; q23) | t (9; 11) (p22; q23) | t (11; 19) (q23; p13.1) | t (11; 19) (q23; p13.3) |
|---|---|---|---|---|---|
| Patients examined | 21 | 7 | 11 | 2 | 5 |
| Patients with rearrangements | 21 | 7 | 11 | 2 | 5 |
| Two rearranged bands | 17 | 3 | 8 | 2 | 4 |
| One rearranged band | 4 | 4 | 3 | 0 | 1 |
| ALL | 21 | 1 | 1 | 0 | 3 |
| AML | 0 | 6 | 10 | 2 | 2 |
| Children | 8 | 3 | 5 | 0 | 3 |
| Adults | 13 | 4 | 6 | 2 | 2 |

*The two cell lines, RS4; 11 and SUP-T13, are not included.

been reported as recurring abnormalities, including translocations involving 6p12, 10p11, 10q22, 15q15, 18q21, and 22q12, and one case with inv(11) (q14q23), showed MLL rearrangements (Table 4). The rearrangements detected in cell lines included RS4;11 with a t(4;11), SUPT13 with a t(11;19), and Karpas 45 with a t(X;11) (q13;q23).

The 0.7B MLL probe did not detect rearrangements in remission samples from patients who had rearrangements in the DNA from their leukemia cells. In addition, rearrangements were not identified in a few cases with uncommon 11q23 translocations. These included AML patients with a t(4;11) (q23;q23), and a t(5;11) (q13;q23), and an ALL with a t(10;11)(p13;q23). However, and importantly, no patients were identified with the common 11q23 translocations who failed to show rearrangements with the 0.7 kilobase cDNA fragment termed 0.7B.

The age distribution of the leukemia patients in this series was broad; 11 patients were one year or less, 16 were between the ages of two and 16, and 31 were 17 years or older. There were 27 females and 31 males. The phenotype of the leukemias in these patients showed 28 with ALL and 30 with AML. The cases with ALL and AML were indistinguishable by Southern blot analysis. In 70% of cases, two rearranged bands, corresponding to the two derivative chromosomes, were detected. Only a single rearranged band was detected in the remaining 30% of cases (FIG. 7). To determine whether there were any potential correlations with the presence of one versus two rearranged bands, the patients were analyzed by karyotypic abnormalities, phenotype of the leukemic cells, and by age. No significant associations between the number of rearranged bands and any of these subgroups were found.

In addition to these acute lymphoid and myeloid leukemias, 20 cases of non-Hodgkin's lymphomas were also examined. Rearrangements were detected in three of these patients. This included one patient with a follicular small cleaved-cell lymphoma who had a karyotype which showed both a t(14;18)(q32;q21) and a t(6;11)(p12;q23), a patient with Burkitt's lymphoma whose karyotype included a t(8;14)(q24;q32) and an inv(11)(q14q23), and a patient with a diffuse mixed small cleaved cell and large cell lymphoma whose karyotype also included a trisomy 21. The other 17 lymphomas with 11q23 abnormalities, primarily deletions and duplications, did not show rearrangements.

To distinguish which derivative chromosome is represented by each of the rearranged bands on Southern blot analysis, sequences from the centromeric and telomeric portions of the 0.7 kilobase cDNA fragment, 0.7B, were amplified by PCR to create distinct DNA probes. The centromeric PCR fragment detected the germline band and only one of the rearranged bands on Southern blot analysis. Thus, the rearranged band detected with this probe corresponds to the derivative 11 [der(11)] chromosome. The fragment amplified by PCR from the portion of the 0.7 kilobase cDNA fragment telomeric to the breakpoint was also hybridized to the same blots. The telomeric probe identified the germline band as well as the derivative chromosome of the other translocation partner. Clearly in cases with two rearranged bands, both derivative chromosomes are present. However, in the cases in which only one rearranged band is detected, it consistently is identified only by the centromeric probe. Therefore, the sequences immediately centromeric to the breakpoint are always preserved but the sequences distal to the breakpoint appear to be deleted in 30% of cases.

In two of the patients (both Japanese) analyzed, a different pattern of hybridization was noted with the three probes employed. In one patient with a t(1;11) and another with a t(41;11), the 0.7 kilobase cDNA probe and the centromeric PCR probe both identified the same two rearranged bands (FIG. 8). In all other cases, the centromeric PCR probe recognized only one of the two rearranged bands. In these two patients as in all other cases, the telomeric PCR probe detected only one of the two rearranged bands. Presumably, these breaks differed from the remainder of cases that were examined. Clearly, a portion of the exon sequences in these two patients, which in all other cases remains on the der(11), is translocated to the other derivative chromosome. The breaks may occur either within one or more exons on the centromeric side of the 8.3 kilobase genomic fragment or alternatively, if more than one exon is present, the breaks may occur within an intron separating these exons. Further analysis of the exon/intron boundaries within the 8.3 kilobase genomic BamHI fragment will allow the determination of the precise localization of these breakpoints.

3. Discussion

The present inventors have identified DNA rearrangements in 61 patients and three cell lines with 11q23 abnormalities that affect the MLL gene and have delineated an 8.3 kilobase breakpoint cluster region within this gene using a 0.7 kilobase BamHI cDNA fragment (seq id no:1) as a probe. Rearrangements have been detected in all 48 cases examined with the t(4;11), t(6;11), t(9;11), and both types of t(11:19) as well as in 12 rare translocations, three insertions, and one inversion involving 11q23. Rearrangements were also detected in three patients with non-Hodgkins lymphoma. These are the first cases of lymphoma that have been found to share the same breakpoint as the leukemias with 11q23 translocations. While rearrangements are detectable with multiple restriction enzymes, digestion with only a single enzyme, BamHI, was sufficient to identify each case with a rearrangement. In 70% of these cases, two rearranged bands, corresponding to the two derivative chromosomes, were identified and in 30%, only one band was present which we showed was derived from the der(11) chromosome.

The present study using the novel probes described above, particularly the 0.7 kb BamHI fragment, gave significantly improved results over all previously reported studies. For example, Cimino et al. described the identification of a 0.7 kb DdeI genomic fragment that detected rearrangements in a 5.8 kilobase region in 6 of 7 patients with the t(4;11), 4 of 5 with t(9;11), and 3 of 4 with the t(11;19) (Cimino et al., 1991). In three of these 16 patients, two rearranged bands were detected and in the remainder, only one rearranged band was identified. Subsequently, they reported on an additional 14 patients with this probe (Cimino et al., 1992). In their combined series, this probe detected rearrangements in 26 of 30 cases (87%) with the t(4;11), t(9;11), and t(11;19). They hypothesize that the breaks in the 4 cases that were not identified with their probe occur either at another site within this gene or at other loci in 11q23. Assuming that the true incidence of rearrangements within the breakpoint cluster region in patients with the 5 common 11q23 translocations is 87%, then the likelihood, calculated by binomial probabilities, of identifying rearrangements in 48 of 48 consecutive cases is 0.0014. Thus, the failure to detect rearrangements in those 4 cases by Cimino and colleagues is likely due to the separation of these breaks from the genomic DdeI probe by a DdeI restriction site.

Importantly, whereas the breakpoint in many cases with 11q23 translocations may be contained within a 5.8 kilobase genomic fragment, the breakpoint cluster region of the present invention encompasses a larger region of 8.3 kilobases and contains the breakpoints in all leukemia cases with the common translocations, as well as in all except three of the rare translocations examined.

Pulsed field gel electrophoresis (PFGE) and fluorescence in situ hybridization (FISH) both have been used to map the region containing the 11q23 breakpoints in leukemias (Savage et al., 1988;1991; Yunis et al., 1989; Tunnacliffe & McGuire, 1990). With FISH, the breakpoint lies telomeric to the CD3G gene and centromeric to the PBGD gene (Rowley et al., 1990). With (PFGE), the distance between the CD3G gene and the breakpoint in the t(4;11) has been narrowed to 100–200 kilobases (Das et al., 1991). Chen et al. (1991) have shown by PFGE that there is a clustering of breakpoints in eight cases with the t(4;11) and in two other patient samples with 11q23 translocations but the size and location of this region could not be determined precisely.

Whereas the data presented herein and that of Cimino et al. (1991; 1992) indicate a clustering of breakpoints, several studies have suggested that the breakpoints on 11q23 may be heterogeneous. Using cosmid probes and FISH, Cherif et al. (1992) found that one of their probes was proximal to the breakpoint in the t(11;19) and distal to those in the t(4;11), t(6;11), and t(9;11). Cotter et al. (1991) using PCR amplification of microdissected material from 11q23 reported that the breaks in two t(6;11) cases were proximal to the CD3D gene and that the breakpoints in the t(4;11) and t(9;11) were distal to this gene.

Molecular studies have confirmed that the breakpoints in translocations involving the antigen receptor loci on chromosome 14 differ from the 11q23 translocations just discussed. Studies on the RCK8 B-cell lymphoma line which has a t(11;14)(q23;q32) showed that the immunoglobulin heavy chain constant region gene and a gene called RCK were involved in the translocation (Akao et al., 1990;1991a). Mapping data indicate that RCK is over 100 kilobases telomeric to MLL (Radice & Tunnacliffe, 1992). In addition, the present inventors cloned a t(11;14)(q23;q11) from a patient with a null-cell ALL and identified rearrangements of the T cell receptor alpha/delta locus. DNA probes from this 11q23 breakpoint failed to show rearrangements in leukemias with the common 11q23 translocations. Mapping data indicate that this breakpoint is approximately 700 kilobases telomeric to MLL. Therefore, band 11q23 contains breakpoints for at least three different cancer-related translocations. However, the data presented herein establish a tight clustering of breakpoints in the MLL gene which is centromeric to RCK and the other t(11;14) breakpoints previously described by the inventors.

In reciprocal translocations, the identification of the derivative chromosome containing the critical junction is essential. Based on data from Southern blot analysis, FISH, and cytogenetic analysis of complex translocations, the inventors propose that the der(11) contains the critical junction. At the molecular level, the Southern blot analyses show a consistent pattern that indicates that the 5' portion of the exon sequences centromeric to the breakpoint on the der(11) are always conserved. In those cases in which the 0.7 kilobase cDNA fragment identifies one rearranged band, it is always detected by only the centromeric PCR probe. Thus, exon sequences from the centromeric portion of the 8.3 kilobase BamHI genomic fragment are always preserved on the der(11) but the exon sequences from the telomeric portion of this genomic fragment can be deleted in the formation of the translocation.

Previously, the inventors identified a patient with a t(9;11) who was found to have a deletion by FISH of a series of probes spanning several hundred kilobases telomeric to the breakpoint on 11q23 (Rowley et al., 1990). On Southern blot analysis of this patient's DNA, only one rearranged band was identified and thus the exon telomeric to the breakpoint was deleted. Recently, using FISH, the present inventors also found that a phage clone containing a large portion of the 14 kilobase genomic BamHI fragment immediately telomeric to the 8.3 kilobase breakpoint cluster region was also deleted in this patient. This 14 kilobase genomic BamHI fragment contains an open reading frame of MLL. Presumably, all of the coding sequences distal to the breakpoint are deleted in this patient. In addition, another patient with a t(6;11) was also found to have one rearranged band on Southern analysis and a deletion of this same phage clone by FISH. Thus in several patients, deletions begin within the breakpoint cluster region and extend distally to include the region containing coding sequences of the gene.

The molecular and FISH data indicating that the der(11) chromosome contains the critical junction are supported by an analysis of complex translocations that involve three chromosomes. For example, in a t(4;11;17)(q21;q23;q11), the movement of the 4q to 11q {the der(11)} is conserved whereas the 11q is translocated to the derivative 17 chromosome. An analogous pattern has been identified in 13 cases of complex translocations. Based on the data of the present invention, the following model is proposed. As a result of the translocation, sequences on the der(11) are joined to a large number of other chromosomal breakpoint regions, 19 detected in the inventors' laboratories alone. Presumably, the 5' sequences of the MLL gene are thus juxtaposed to 3' sequences from genes located on the other translocation partners. The present invention provides the molecular tools to allow the functional consequences of these translocations to be determined.

The present inventors have delineated a breakpoint cluster region in the MLL gene and have identified rearrangements in a total of 19 different translocations, insertions, and inversions involving 11q23. The 0.7 kilobase cDNA probe of the present invention, and its derivative centromeric and telomeric PCR probes, are proposed to be broadly applicable to clinical diagnosis, particularly as they detect all of the rearrangements in DNA digested with a single enzyme (BamH1). This is envisioned to be useful in the rapid detection of leukemia in both children and adults and will be especially important in leukemic infants under one year of age in whom the single most common chromosomal abnormality is a translocation involving 11q23. In addition, it is contemplated that this probe will be effective for monitoring response to chemotherapy and for evaluation of minimal residual disease following treatment. These probes will be essential in cloning the breakpoints of leukemias which involve the MLL locus and in further molecular analysis of these translocations.

EXAMPLE III

Sequencing of the 8.3 kilobase Genomic BamH1 Fragment that Contains All of the Common MLL Translocation Breakpoints.

The inventors have recently obtained the DNA sequence for the 8.3 kb genomic BamH1 fragment which contains all of the common translocation breakpoints. This sequence is provided in the present application as seq id no:6.

The inventors envision using this new sequence information to map the intron-exon boundaries within this region and to identify the specific nucleotides involved in the breakpoint junctions in various patients.

EXAMPLE IV

Expression of MLL-Derived Proteins and Anti-MLL Antibodies

1. Production of Antisera to a Region of MLL Telomeric to the Breakpoint Region (MLL Amino Acids of Seq Id No:8)

To express MLL amino acids of seq id no:8 (corresponding to MLL amino acids 2772–3209 of Tkachuk et al., 1992), plasmid 14-7 was digested with EcoR1 and the insert was ligated into plasmid pGEX-KG digested with EcoR1, resulting in the 1.3 kb MLL fragment inserted in frame into the expression vector. This construct produces an MLL amino acid-containing fusion protein with GST (glutathione-S-transferase). This DNA was transformed into JM101 bacteria. To produce large quantities of the MLL protein corresponding to seq id no:8 for production of rabbit antisera, the plasmid-transformed bacteria were grown in LB medium and induced to express the fusion protein with IPTG.

This fusion protein was purified using glutathione-agarose affinity chromatography, followed by preparative SDS-polyacrylamide gel electrophoresis. The fusion protein was then electroeluted from the gel and used to immunize rabbits in order to generate specific antisera (performed by Josman Laboratories, Napa, Calif.). The rabbit antisera produced against the MLL protein corresponding to seq id no:8 has a very high titer by western blotting and reacts specifically with the MLL portion of the fusion protein (FIG. 10).

2. Production of Antisera to a Region of MLL Centromeric to the Breakpoint Region (MLL Amino Acids 323–623 from Seq Id No:7)

Specific MLL oligonucleotides with SmaI restriction enzyme sites were used as PCR primers to amplify MLL amino acids 323–623 from seq id no:7 using the plasmid 14P18B as template. This amplified DNA was digested with SmaI and ligated into plasmid pGEX-KT (an improved version of plasmid pGEX-KG used above) that had been digested with SmaI. This results in MLL amino acids 323–623 (representing MLL amino acids 1101–1400 of Tkachuk et al., 1992), corresponding to the proline-rich region, being inserted in-frame into the expression vector. This DNA was transformed into BL21 bacteria. Large amounts of this fusion protein can be produced using this methodology and employed in the production of specific antisera, for example, using rabbits.

Such antibodies may be employed as part of the ongoing studies directed to the MLL protein. For example, they may employed to determine the MLL protein localization within the cell, or to determine whether this protein binds to DNA. The generation of monoclonal antibodies has also been made possible by the present invention.

EXAMPLE V

Expression of Various MLL Domains

The MLL zinc finger regions (corresponding to amino acids 1350–1700, 1700–2000, and 1350–2000 of Tkachuk et al., 1992) have been cloned into the pGEX-KT expression vector as described above. In addition, the inventors propose to clone various of the MLL protein coding regions into the expression vector pSg24 in pieces ranging from 300–650 amino acids to allow the functional definition of the MLL protein.

EXAMPLE VI

Detection of MLL Gene Rearrangements in Karpas 45 Leukemic Cells with a t(X;11)(q13;q23) Translocation This example concerns the detection and characterization of aberrant MLL transcripts in Karpas 45 leukemic cells with a t(X;11)(q13;q23) translocation and provides further evidence of the utility of the present probes in detecting leukemic cells with different breakpoints.

In this analysis of the Karpas 45 cell line (Karpas et al., 1977), known to have a t(X;11) (q13;q23) translocation (Kearney et al., 1992), the inventors show the MLL gene to be rearranged and demonstrate the presence of two altered MLL transcripts which come from the der(11) chromosome. MLL was also found to be rearranged using Southern blot analyses of DNA from Karpas 45.

1. Materials and Methods

The T-cell line Karpas 45, established from a patient with a T-cell ALL, was obtained from A. Karpas (University of Cambridge, England, Karpas et al., 1977). Karpas 45 has been shown, by fluorescence in situ hybridization, to have a t(X,11 (q13;q23), which involves rearrangement of the MLL gene. The cell lines RC-K8 and RCH-ADD, which do not have chromosomal translocations that involve MLL have been described previously (Ziemin-van Der Poel et al., 1991) and were used as controls.

The cDNA probe 14P-18B has been described herein in the previous examples. The cDNA clone was digested with EcoR1 and BamH1 to give three fragments for use in Northern and Southern blot hybridizations. The 0.7B probe, which spans the breakpoint, and the 1.5EB probe, centromeric to the breakpoint, have been described hereinabove. A further 0.8 kb EcoR1 fragment, which is telomeric to the breakpoint was obtained and used in this study, this probe is termed 0.8E. It should be noted that the EcoR1 site used to excise the 1.5EB fragment was a cloning site.

DNA was extracted from the Karpas 45 cell line and normal human placenta, digested with the restriction enzyme BamH1 and electrophoresed on a 1% agarose gel. Poly A$^+$ RNA was isolated from the cell lines Karpas 45, RC-K8 and RCH-ADD using the Fast Track Isolation Kit (Invitrogen) and 5 $\mu$g were electrophoresed on a 0.8% formaldehyde gel as described hereinabove. Radioactive labeling of cDNA fragments, hybridization and washing conditions were as described in the previous examples.

2. Results and Discussion

To determine if MLL was rearranged in the Karpas 45 cell, known to have an 11q23 translocation, a Southern blot with BamHI digested DNA was hybridized to the 0.7B probe. FIG. 11 shows that the MLL gene was rearranged in this 11q23 translocation and that two rearranged fragments are evident, indicating the detection of sequences from both derivative chromosomes X and 11.

To determine the nature of the MLL transcripts in this cell line, a Northern blot was hybridized sequentially to three different fragments of the 14P-18B cDNA clone. The fragments used were 0.8E (telomeric to the breakpoint), a 0.7B fragment (which spans the breakpoint) and finally a 1.5EB fragment (which is centromeric to the breakpoint), as shown in FIG. 2. All three fragments were found to show weak hybridization to the two normal sized MLL transcripts in all the cell lines (FIG. 12).

The 0.7B and the 1.5EB fragments detected two additional transcripts, an abundant 8.0 kb transcript and a diffuse band around 6.0 kb in the Karpas 45 cell line, which were not present in the control cell lines (FIG. 12). Furthermore, these two transcripts were not detected by the more telomeric 0.8E fragment (FIG. 12). Hybridization to actin indicated that there was approximately 50% less RNA in the Karpas 45 cell line Lane compared to RNA in the control cell line (FIG. 12).

It should be noted here that the two normal sized MLL transcripts, listed as being of about 15 and 13 kilobases, are the same transcripts previously referred to as about 12 and about 11.5 kb throughout the earlier examples. This illustrates the fact that the studies shown in FIG. 12 were conducted at a later date and that, as mentioned before, the earlier Northern blot size determinations were generally approximations, as is well known to result from using this method to determine sizes of greater than about 9 or 10 kb. However, this study of the Karpas cell line further exemplifies the utility of the probes in differentiating between normal and leukemic cells.

The present study further supports the inventors' findings that the breakpoint cluster region in the MLL gene occurs within a 9.0 kilobase BamH1 genomic fragment. On Northern analysis all three of the cDNA fragments detected the normal-sized MLL transcripts in the control cell lines, and to a lesser extent in the Karpas 45 cell line. However, the 0.7B and the 1.5EB fragments, which span and are centromeric to the breakpoint junction respectively, detected two additional altered transcripts of the MLL gene in the Karpas 45 cell line. As the more telomeric 0.8E fragment did not hybridize to these two novel transcripts, it may concluded that these transcripts are altered MLL transcripts coming from the derivative 11 chromosome.

Evidence of any altered MLL transcripts derived from the reciprocal chromosome X was not found in the Karpas 45 cell line. This is in keeping with the inventors' proposition that the derivative 11 chromosome contains the critical junction in two and three way reciprocal translocations involving chromosome band 11q23 and the associated rearrangement of the MLL gene.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. All claimed matter and methods can be made and executed without undue experimentation.

REFERENCES

The following references, to the extent that they provide exemplary procedural or other details supplementary to those set forth herein, are specifically incorporated herein by reference.

Akao Y, Tsujimoto Y, Finan J, et al. Molecular characterization of a t(11;14)(q23:q32) chromosome translocation in a B-cell lymphoma. Cancer Res 1990;50:4856–59.

Akao Y, Seto M, Takahashi T, et al. Molecular cloning of the chromosomal breakpoint of a B-cell lymphoma with the t(11;14)(q23;q32) translocation. Cancer Res (1991a) 51:1574–76.

Akao, Y., Seto, M., Toshitada, T. et al. Cancer Res. (1991b) 51, 6708–6711.

Arthur D C, Bloomfield C D, Lindquist L L, Nesbit M E, Jr. Translocation 4;11 in acute lymphoblastic leukemia: Clinical characteristics and prognostic significance. Blood 1982;59:1:96–99.

Chen C-S, Medberry P S, Arthur D C, Kersey J H. Breakpoint clustering in t(4;11)(q21;q23) acute leukemia. Blood 1991;78:2498–504.

Cherif D, Der-Sarkissian H, Derre J, et al. The 11q23 breakpoint in acute leukemia with t(11;19)(q23;p13) is distal to those of t(4;11), t(6;11) and t(9;11). Genes Chrom Cancer 1992;4:107–12.

Chromosome Co-ordinating Meeting 1992; Eds. Cuticchia, A. J, Pearson, P. L., and Klinger, H. P.; Genome Priority Reports, Vol. I, 1993.

Cimino G, Moir D T, Canaani O, et al. Cloning of ALL-1, the locus involved in leukemias with the t(4;11)(q21;q23), t(9;11)(p22;q23), and t(11;19)(q23;p13) chromosome translocations. Cancer Res (1991) 51:6712–14.

Cimino G, Nakamura T, Gu Y, et al. An altered 11-kilobase transcript in leukemic cell lines with the t(4;11)(q21;q23) Chromosome Translocation. Cancer Res (1992) 52:3811–13.

Cotter F E, Lillington D, Hampton G, et al. Gene mapping by microdissection and enzymatic amplification: Heterogeneity in leukaemia associated breakpoints on chromosome 11. Genes Chrom Cancer 1991;3:8–15.

Cuneo A, Michaux J L, Ferrant A, et al. Correlation of cytogenetic patterns and clinicobiological features in adult acute myeloid leukemia expressing lymphoid markers. Blood 1992;79:720–727.

Das S, Cotter F E, Gibbons B, Dhut S, Young B D. CD3G is within 200 kb of the leukemic t(4;11) translocation breakpoint. Genes Chrom Cancer 1991;3:44–47.

Djabali M, Selleri L, Parry P, Bower M, Young B D, Evans G A. A trithorax-like gene is interrupted by chromosome 11q23 translocations in acute leukaemias. Nature Genetics 1992;2:113–118.

Drexler H G, Thiel E, Ludwig W-D. Review of the incidence and clinical relevance of myeloid antigen-positive acute lymphoblastic leukemia. Leukemia 1991;5:637–45.

Fourth International Workshop on Chromosomes in Leukemia, 1982: Clinical significance of chromosomal abnormalities in acute nonlymphoblastic leukemia. Cancer Genet Cytogenet 1984;1:332–350.

Gibbons B, Katz E, Ganly P, Chesells J M. Infant acute lymphoblastic leukaemia with t(11;19). Br J Haematol 1990;74:264–269.

Gu Y, Nakamura T, Alder H, Prasad R, Canaani O, Cimino G, Croce C M, Canaani E. The t(4;11) chromosome translocation of human acute leukemias fuses the ALL-1 gene, related to drosophila trithorax, to the AF-4 gene, Cell, 1992;71:701–708.

Gu Y, Cimino G, Alder H, Nakamura T, Prasad R, Canaani O, Moir D T, Jones C, Nowell P C, Croce C M, Canaani E. The (4;11)(q21;q23) chromosome translocations in acute leukemias involve the VDJ recombinase. PNAS, 1992;89:10464–10468.

Harnden D G, Klinger H P (eds): ISCN, An International System for Human Cytogenetic Nomenclature; published in collaboration with Cytogenet Cell Genet, Karger, Basel, 1985; also in Birth Defects: Original Article Series, Vol 21, No 1, March of Dimes Birth Defects Foundation, New York, N.Y., 1985.

Heim, S., & Mitelman, F. (1987) Cancer Cytogenetics. N.Y. Alan R. Liss, Inc.

Hudson M M, Raimondi S C, Behm F G, Pui C-H. Childhood acute leukemia with t(11;19)(q23;p13). Leukemia 1991;5:1064–68.

Jack, I., Seshadri, R., Garson, M. M., Michael, P., Callen, D., Zola, H. & Morley, A. (1986) Cancer Genet. Cytogenet. 19, 261–269.

Jameson & Wolf. "The Antigenic Index: A Novel Algorithm for Predicting Antigenic Determinants," Comput. Appl. Biosci., 4(1):181–186, 1988.

Kaneko, Y, Shikano T, Maseki N, et al. Clinical characteristics of infant acute leukemia with or without 11q23 translocations. Leukemia 1988;2:672–76.

Karpas A, Hayhoe F G J, Greenberger J S, et al. Haemic cell lines: Evidence for heterogeneity. Leukemia Research 1977;1:35–49.

Kearney et al., (1992), Chromosome 11q23 translocations in both infant and adult acute leukemias are detected by in situ hybridization with a yeast artificial chromosome, Blood, 80:1659–1665.

Kubonoshi, I., Niiya, K., Yashita, M., et al. (1986) Cancer 58, 1453–1460.

Kyte, J. and Doolittle, R. F. A simple method for displaying the hydropathic character of a protein. J. Mol. Biol., 157(1):105–132, 1982.

Lu, D. & Yunis, J. J. (1992) Nucl. Acids Res. 20, 1967–1972.

Mitelman F, Kaneko Y, Trent J M. Human gene mapping 11: Report of the committee on chromosome changes in neoplasia. Cytogenet Cell Genet 1991;58:1053–79.

Parkin J L, Arthur D C, Abramson C S, et al. Acute leukemia associated with the t(4;11) chromosome rearrangement: ultrastructural and immunologic characteristics. Blood 1982;60:1321–31.

Pui C-H, Frankel L S, Carroll A J, et al. Clinical characteristics and treatment outcome of childhood acute lymphoblastic leukemia with the t(4;11)(q21;q23): A collaborative study of 40 cases. Blood 1991;77:440–47.

Radice, P. & Tunnacliffe. (1992) Genes Chromosomes Cancer 5, 50–56.

Ratain & Rowley. (1992) Annals of Oncology, 3, 107–111.

Rowley J D. Recurring chromosome abnormalities in leukemia and lymphoma. Semin Oncol (1990a) 27:122–36.

Rowley J D. Molecular cytogenetics: Rosetta Stone for understanding cancer-twenty-ninth G.H.A. Clowes Memorial Award Lecture. Cancer Res (1990b) 50:3816–25.

Rowley J D, Diaz M O, Espinosa R III, et al. Mapping chromosome band 11q23 acute leukemia with biotinylated probes: Identification of 11q23 translocation breakpoints with a yeast artificial chromosome. Proc Natl Acad Sci 1990;87:9358–9362.

Sambrook J. et al. (1989), Molecular Cloning: A Laboratory Manual, Cold Spring Harbor Laboratory, N.Y.

Samuels B L, Larson R A, Le Beau M M, et al. Specific chromosomal abnormalities in acute nonlymphocytic leukemia correlate with drug susceptibility in vivo. Leukemia 1988;2:79–83.

Sandberg A A. The chromosomes in human cancer and leukemia. 2nd ed. New York: Elsevier, 1990.

Savage P D, Jones C, Silver J, et al. Mapping studies and expression of genes located on human chromosome 11, band q23. Cytogenet Cell Genet 1988;49:289–92.

Savage P D, Shapiro M, Langdon W Y, et al. Relationship of the human protooncogenes CBL2 on 11q23 to the t(4;11), t(11;22), and t(11;14) breakpoints. Cytogenet Cell Genet 1991;56:112–15.

Shima, E. A., Le Beau, M. M., McKeithan, T. W. et al. (1986) Proc. Natl. Acad. Sci. USA 83, 3439–3443.

Smith S D, McFall P, Morgan R, et al. Long term growth of malignant thymocytes in vitro. Blood 1989;73:2182–87.

Stong R C, Kersey J H. In vitro culture of leukemic cells in t(4;11) acute leukemia. Blood 1985;66:439–43.

Sundstrom, C., & Nilsson, K. (1976) Int. J. Cancer 17, 565–577.

Tkachuk D C, Kohler S, Cleary M L. Involvement of a homolog of drosophila trithorax by 11q23 chromosomal translocations in acute leukemias. Cell 1992;71;691–700.

Tunnacliffe A, McGuire R S. A physical linkage group in human chromosome band 11q23 covering a region implicated in leukocyte neoplasia. Genomics 1990;8:447–53.

Wolf et al., "An Integrated Family of Amino Acid Sequence Analysis Programs," Comput. Appl. Biosci., 4(1):187–191, 1988.

Yunis J J, Jones C, Madden M T, Lu D, Mayer M G. Gene order, amplification, and rearrangement of chromosome band 11q23 in hematologic malignancies. Genomics 1989;5:84–90.

Ziemin-van der Poel S, McCabe N R, Gill H J, et al. Identification of a gene, MLL, that spans the breakpoint in 11q23 translocations associated with human leukemias. Proc. Natl. Acad. Sci. USA 1991;88:10735–739. Correction Proc Natl. Acad. Sci. USA 1992;9:4220.

What is claimed is:

1. An isolated protein comprising the amino acid sequence of SEQ ID NO:7.

2. An isolated protein comprising a sequence of at least 300 continuous amino acids from SEQ ID NO:7.

3. An isolated protein comprising the amino acid sequence of SEQ ID NO:8.

4. The protein of claim 2, wherein the protein comprises amino acids 323–623 of SEQ ID NO:7.

5. The protein of claim 2, wherein the protein includes a zinc finger region.

6. An antibody that specifically binds with the protein of claim 1.

7. An antibody that specifically binds with the protein of claim 6.

8. The protein of claim 2 wherein the protein comprises amino acids 574 to 1184 of SEQ ID NO:7.

9. An isolated protein comprising a sequence of at least 128 contiguous amino acids from SEQ ID NO:7.

10. The protein of claim 9 wherein the protein comprises amino acids 574 to 810 of SEQ ID NO:7.

11. The protein of claim 9 wherein the protein comprises amino acids 1057 to 1184 of SEQ ID NO:7.

12. An antibody that specifically binds with the protein of claim 8.

13. An antibody that specifically binds with the protein of claim 10.

14. An antibody that specifically binds with the protein of claim 11.

* * * * *

UNITED STATES PATENT AND TRADEMARK OFFICE
CERTIFICATE OF CORRECTION

PATENT NO.     : 6,121,419
DATED          : September 19, 2000
INVENTOR(S)    : Rowley et al.

It is certified that error appears in the above-identified patent and that said Letters Patent is hereby corrected as shown below:

On the title page, in Related U.S. Application Data, item [60], after "Pat. No. 5,487,970," please insert -- which is a continuation-in-part of application No. 07/991,224, Dec. 16, 1992, abandoned, -- therefor.

In claim 2, column 65, line 39, pleases delete "continuous" and insert --contiguous -- therefor.

In claim 7, column 65, line 49, please delete "the protein of claim 6" and insert -- the protein of claim 3 -- therefor.

Signed and Sealed this

Fifteenth Day of May, 2001

Attest:

NICHOLAS P. GODICI

Attesting Officer

Acting Director of the United States Patent and Trademark Office